(12) United States Patent
Lee et al.

(10) Patent No.: US 8,927,512 B2
(45) Date of Patent: Jan. 6, 2015

(54) RNA APTAMER SPECIFICALLY BINDING TO CARCINOEMBRYONIC ANTIGEN AND USE THEREOF

(75) Inventors: Seong-Wook Lee, Seoul (KR); Young-Ju Lee, Seoul (KR); Jin-Sook Jeong, Busan (KR)

(73) Assignees: Postech Academy-Industry Foundation, Pohang (KR); Posco, Pohang (KR)

( * ) Notice: Subject to any disclaimer, the term of this patent is extended or adjusted under 35 U.S.C. 154(b) by 61 days.

(21) Appl. No.: 13/241,259

(22) Filed: Sep. 23, 2011

(65) Prior Publication Data
US 2014/0235698 A1    Aug. 21, 2014

Related U.S. Application Data

(63) Continuation-in-part of application No. 12/725,529, filed on Mar. 17, 2010, now abandoned.

(60) Provisional application No. 61/160,912, filed on Mar. 17, 2009.

(51) Int. Cl.
| | | |
|---|---|---|
| A61K 48/00 | (2006.01) | |
| C12Q 1/68 | (2006.01) | |
| C12N 15/115 | (2010.01) | |
| A61K 47/48 | (2006.01) | |
| A61K 31/7105 | (2006.01) | |

(52) U.S. Cl.
CPC ........ *C12N 15/115* (2013.01); *A61K 47/48215* (2013.01); *A61K 47/48046* (2013.01); *A61K 31/7105* (2013.01); *C12Q 1/6886* (2013.01); *C12N 2310/16* (2013.01); *C12Q 2600/118* (2013.01); *C12N 2310/3515* (2013.01)
USPC ....................................... 514/44 R; 435/6.14

(58) Field of Classification Search
None
See application file for complete search history.

(56) References Cited

FOREIGN PATENT DOCUMENTS

KR          100667009 B1 *   1/2007

OTHER PUBLICATIONS

Machine translation of KR 100667009 B1 (above): Lee et al, RNA aptamer Specifically Binding to Metastasis-related CEA Domain, Jan. 2007, pp. 1-10.*

* cited by examiner

*Primary Examiner* — Tracy Vivlemore
*Assistant Examiner* — Kate Poliakova
(74) *Attorney, Agent, or Firm* — Lexyoume IP Meister, PLLC

(57) ABSTRACT

Provided are RNA aptamer specifically binding to cancer metastasis-inducing domain of CEA (Carcinoembryonic antigen), a composition for prevention and/or inhibition and/or diagnosis of cancer metastasis containing the same as an active ingredient, and a method of prevention and/or inhibition and/or diagnosis of cancer metastasis using the same.

12 Claims, 40 Drawing Sheets

Overview of SELEX procedure

Fig. 2A

GROUP II 2ND STRUCTURE
SEQ ID NO: 33

GROUP III 2ND STRUCTURE
(SEQ ID NO: 34)

Fig. 3A
Truncated series sequence and 2$^{ND}$ structure

Trunc. GROUP1-1 (49mer):   GCGGAAGCGUGCUGGGCUAGAAUAAUAAUAAGAAAACCAGUACUUUCGU
SEQ ID NO: 13

Mut. GROUP1-1 (49mer):   GCGGAAGCGUGCUGGGCUAGGGCGGCGGCGGGAAAACCAGUACUUUCGU
SEQ ID NO: 15

Trunc. GROUP1-2 (36mer):   GUGCUGGGCUAGAAUAAUAAUAAGAAAACCAGUAC
SEQ ID NO: 14

Mut. GROUP1-2 (36mer):   GUGCUGGGCUAGGGCGGCGGCGGGAAAACCAGUAC
SEQ ID NO: 16

Loop only (23mer):   GGCUAGAAUAAUAAUAAGAAAAC
SEQ ID NO: 17

Truncated GROUP I-1
SEQ ID NO: 13

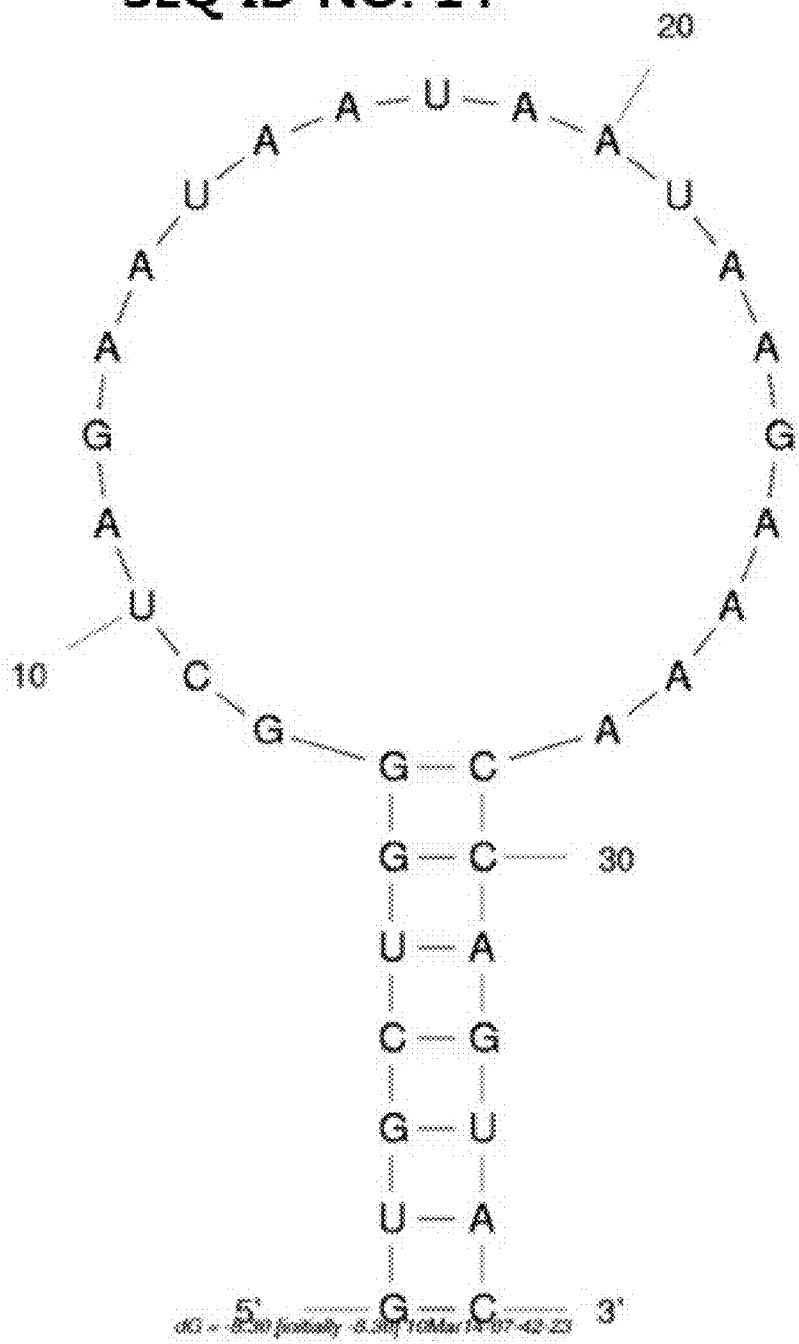

Mut. GROUP I-2
SEQ ID NO: 16

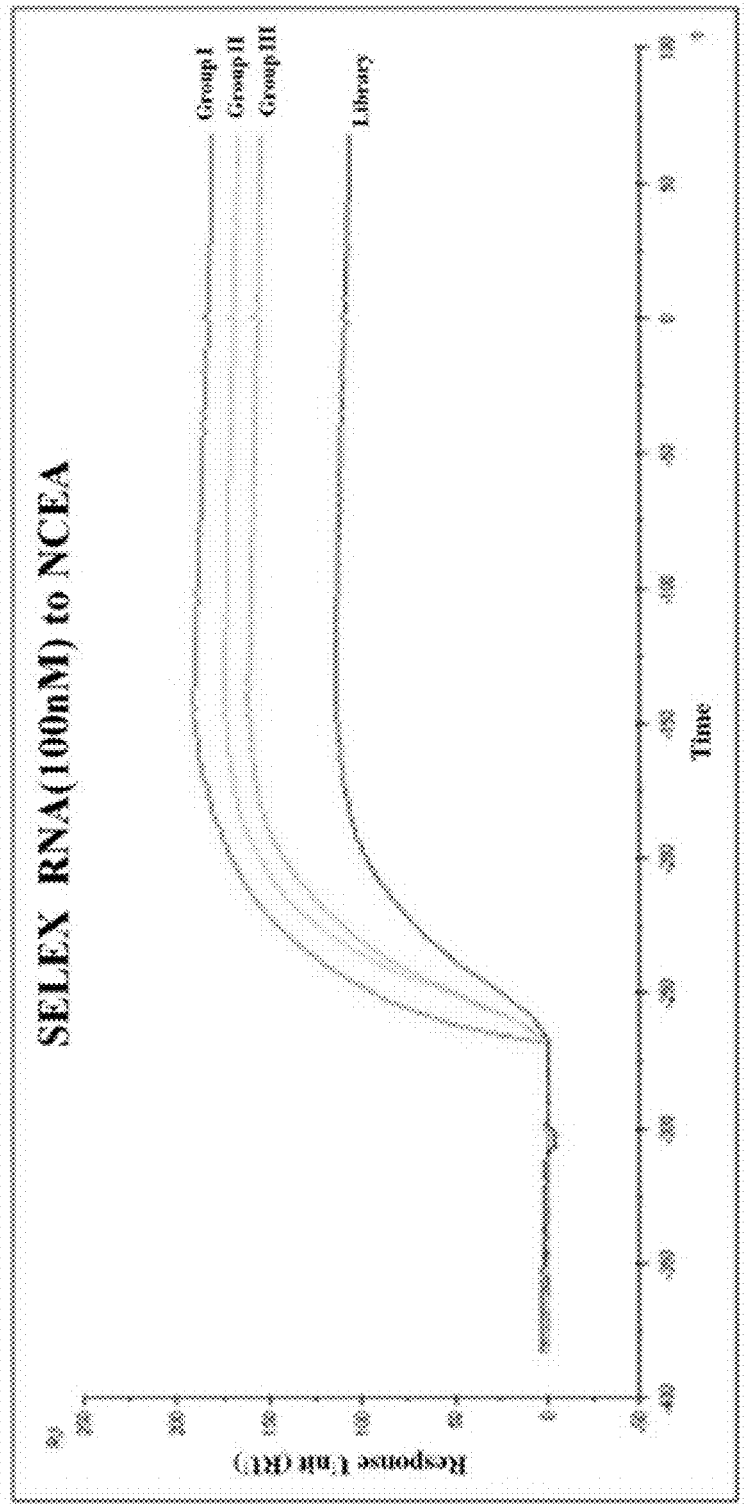

Fig. 5

YJ-1  SEQ ID NO: 13

(cholesteryl-TEG phosphoramidite)-5'-GCGGAAGCGUGCUGGGCUGAGCUUAGAAAUAAUAAUAAGAAAUAAGAAAUAAGAAAUACCAGUACUUUCGU-3'-(inverted 3'-3' Dt)
                                    F  F F FF    FF     FF      F  F  F       FF  F FFFFF  F

Homotypic cell Aggregation inhibition assay

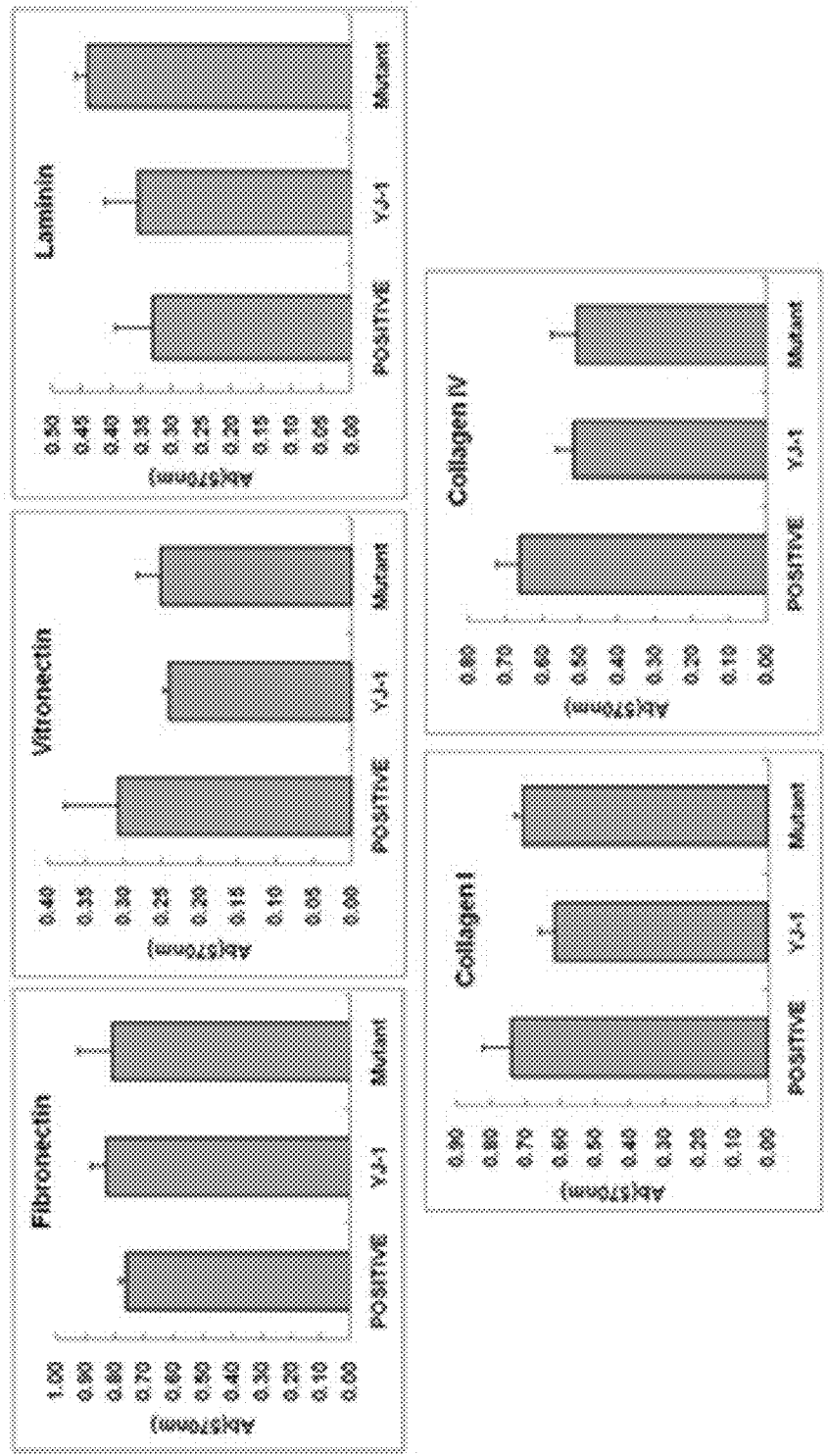

LS174T (human colon adenocarcinoma cell line)

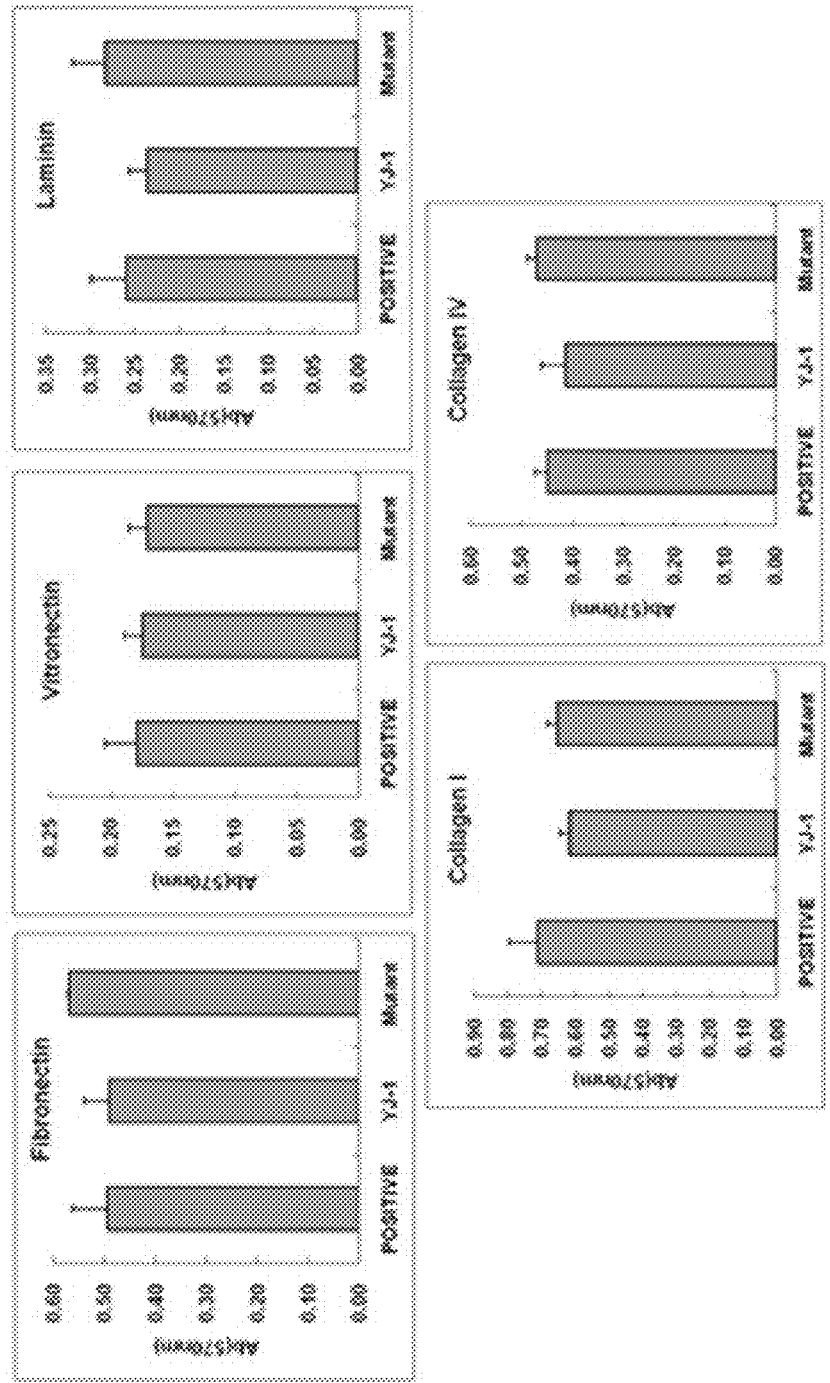

Capan-1 (Human pancreatic adenocarcinoma cell line)

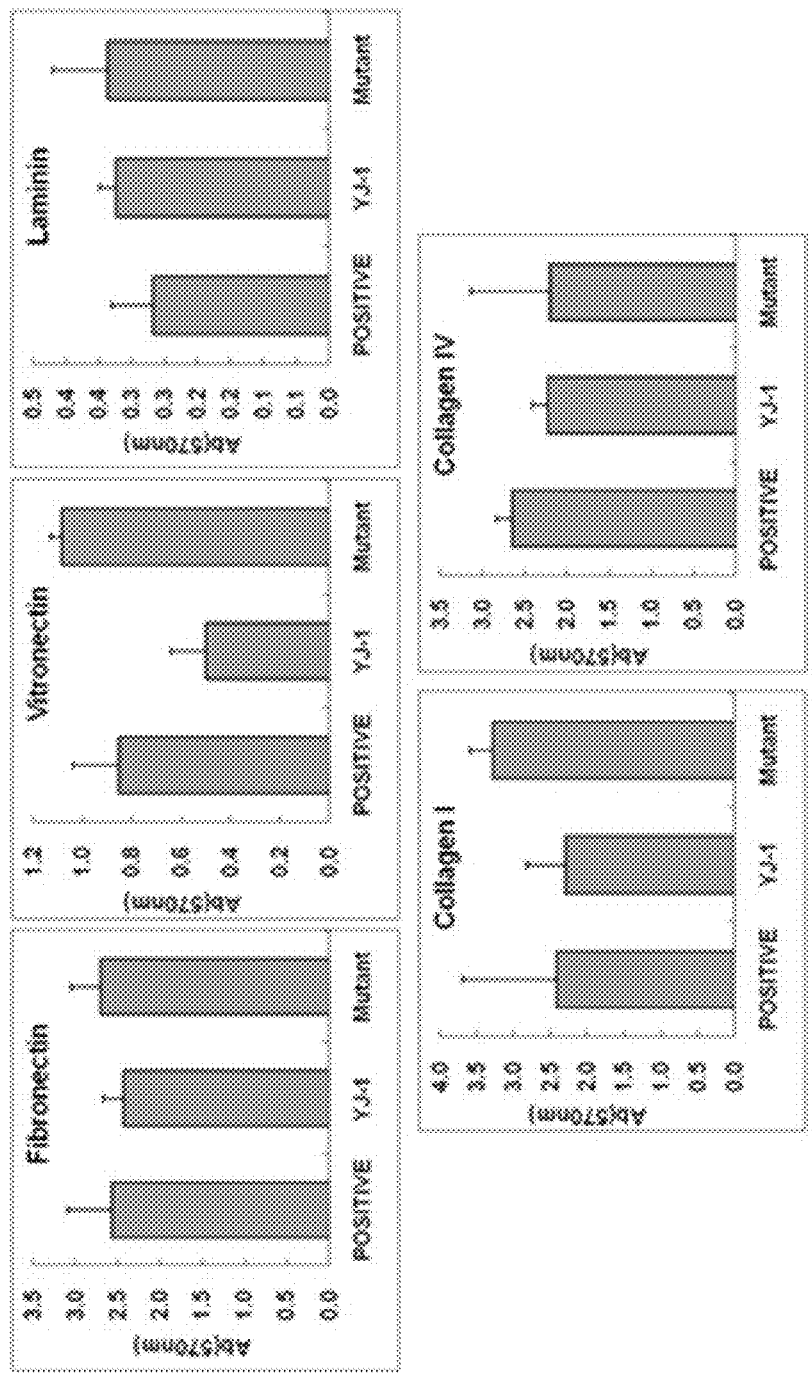

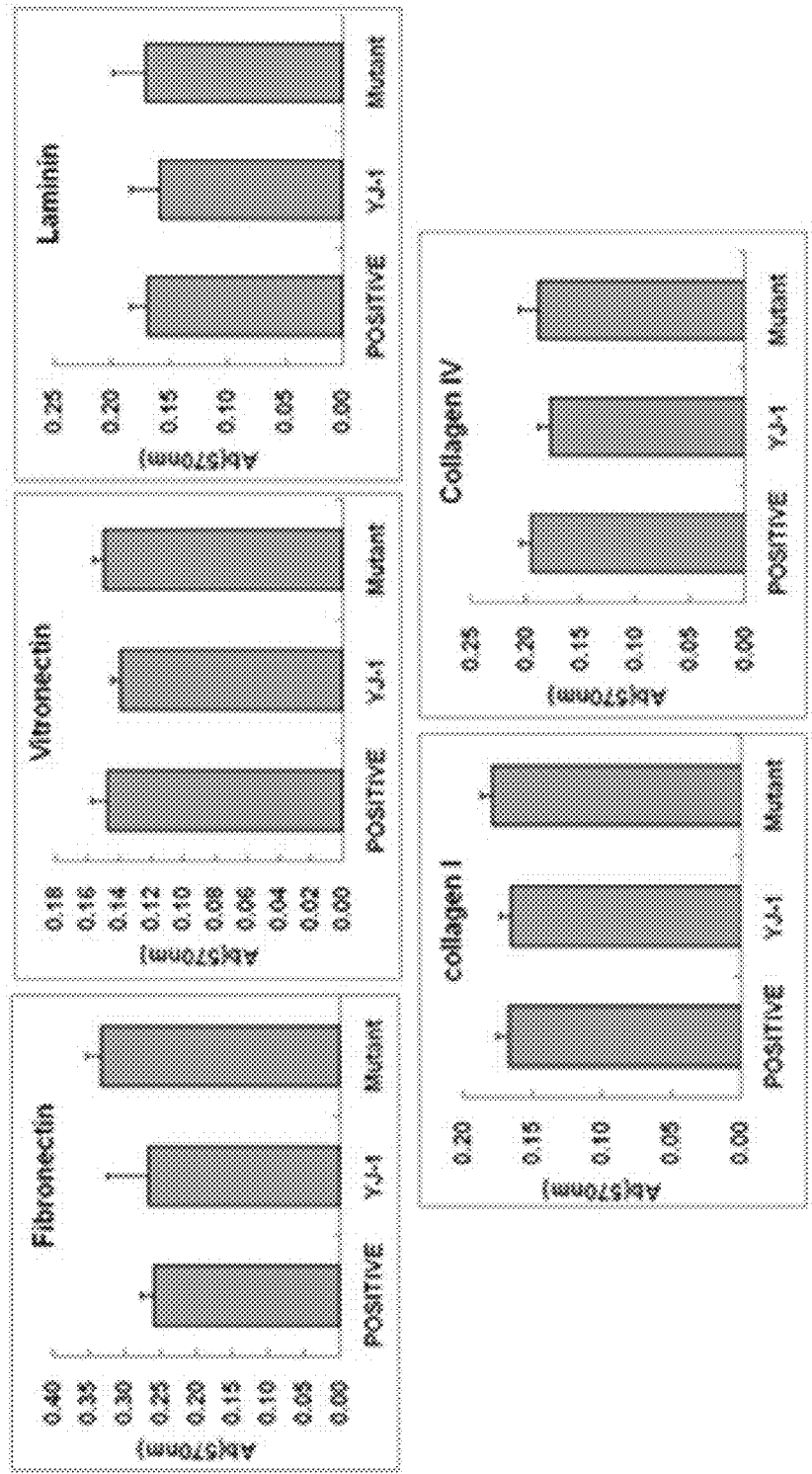

Fig. 13
CEA positive cell line
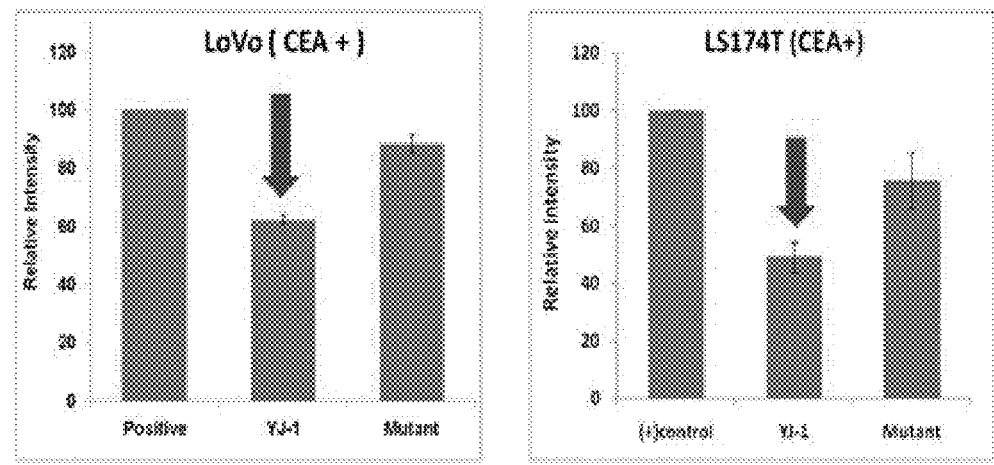
CEA negative cell line
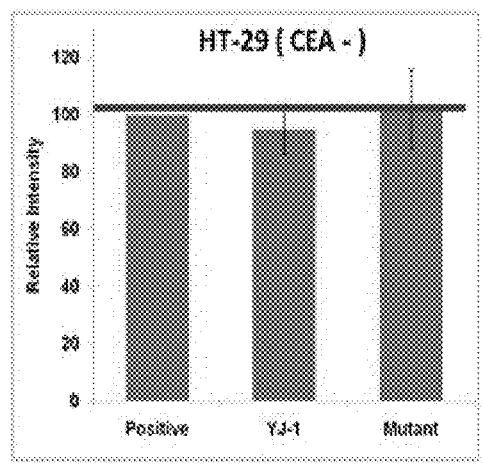

RNA APTAMER SPECIFICALLY BINDING TO CARCINOEMBRYONIC ANTIGEN AND USE THEREOF

CROSS-REFERENCE TO RELATED APPLICATION

This is a continuation in part application Ser. No. 12/725,529, filed on Mar. 17, 2010, now abandoned, which claims priorities to and the benefits of U.S. Provisional Application No. 61/160,912 filed on Mar. 17, 2009, and the entire contents of which are incorporated herein by reference.

BACKGROUND OF THE INVENTION (a) Field of the Invention

This disclosure relates to RNA aptamer specifically binding to a cancer metastasis-inducing domain of CEA (Carcinoembryonic antigen), a composition for prevention and/or inhibition and/or diagnosis of metastasis containing the RNA aptamer as an active ingredient, and a method of prevention and/or inhibition and/or diagnosis of metastasis using the RNA aptamer.

(b) Description of the Related Art

CEA (Carcinoembryonic antigen: CEACAM5, NCBI accession number: NP_004354), which is 180 KDa glycophosphatidylinositol (GPI)-anchored membrane glycoprotein, is heavily glycosylated. The CEA is consisted of N domain consisting of 107 amino acids at N-terminal, and 6 domains (A1, B1, A2, B2, A3, B3) repeated similarly to Ig (Immunoglobulin), each consisting of 178 amino acids, and the C-terminal is consisted of glycosylphosphatidylinositol membrane anchor. CEA has been studied as a cancer marker, and expressed in 70% of lung cancer and 50% of breast cancer, and colon cancer, stomach cancer and pancreatic cancer. Due to such characteristic, it is widely used clinically to diagnose cancer. CEA expression is known to be related to cell adhesion, inhibition of apoptosis and promotion of metastasis to liver. The level of CEA in blood is mainly used as a basis for determining prognosis after colon cancer surgery.

N domain of CEA is known to increase cell aggregation through the process of inducing interaction between CEA-positive (CEA-expressing) cells, thereby playing an important role to induce metastasis. In particular, 5 amino acids TELPK' existing between N domain and A1 domain of CEA is known to be responsible for binding to kupffer cell that is associated with metastasis. It has been known that the TELPK' is recognized by 80 kDa cell surface receptor on kupffer cell and greatly activate the next receptors by signal transduction, whereby CEA-expressing cells are brought into liver to induce metastasis.

In addition, since CEA is a $Ca^{2+}$ independent intercellular adhesion molecule between homotypic cells, a possibility that a metastasis of CEA-expressing cells may occur by permeation through cell membrane to develop into cancer is suggested. As the result of analyzing CEA amino acid sequence of patients who have a large amount of CEA in blood stream but do not have metastasis to liver, among the patients with CEA-induced diseases, it is confirmed that PELPK region of CEA is mutated, This result suggests a possibility that mutation in PELPK may inhibit binding affinity of CEA to the receptor on the kupffer cell of liver, thereby inhibiting metastasis to liver, suggesting that a ligand to a cancer specific marker may be used as a strong means for cancer diagnosis and development of an effective anticancer therapeutic agent.

SUMMARY OF THE INVENTION

The present inventors developed a novel RNA molecule specifically binding to a linkage region between N domain and A1 domain of a cancer-specific marker CEA (Carcinoembryonic antigen), thereby being useful for inhibition and diagnosis of metastasis, to complete the invention.

One embodiment of the present invention provides an RNA molecule consisting essentially of a specific region within a polynucleotide of SEQ ID NO: 18. The RNA molecule may comprise a nucleotide sequence selected from the group consisting of SEQ ID NO: 1 to 14.

Another embodiment provides an RNA aptamer specifically binding to a linkage region between N domain and A1 domain of CEA, and essentially comprising a specific region within a polynucleotide of SEQ ID NO: 18. The RNA aptamer may comprise a nucleotide sequence selected from the group consisting of SEQ ID NO: 1 to 14.

Another embodiment provides a composition for inhibition and/or prevention of cancer metastasis, containing an RNA aptamer that specifically binds to a linkage region between N domain and A1 domain of CEA, and essentially comprises a specific region within a polynucleotide of SEQ ID NO: 18, and a method of inhibition and/or prevention of cancer metastasis comprising administering said RNA aptamer to a patient in need of inhibition and/or prevention of cancer metastasis. The RNA aptamer may comprise a nucleotide sequence selected from the group consisting of SEQ ID NO: 1 to 14.

Another embodiment provides a composition for diagnosis of cancer metastasis, containing an RNA aptamer that specifically binds to a linkage region between N domain and A1 domain of CEA, and essentially comprises a specific region within a polynucleotide of SEQ ID NO: 18, and a method of diagnosis of cancer metastasis using said RNA aptamer. The RNA aptamer may comprise a nucleotide sequence selected from the group consisting of SEQ ID NO: 1 to 14.

DETAILED DESCRIPTION OF THE EMBODIMENTS

The present invention relates to an RNA molecule specifically binding to a linkage region between N domain and A1 domain of a cancer-specific marker CEA (Carcinoembryonic antigen), use of said RNA molecule as an RNA aptamer for CEA, and inhibition/prevention and diagnosis technologies of metastasis using said RNA aptamer.

RNA aptamer specific to a target protein with high affinity can be separated from an RNA library comprising random polynucleotides through in vitro selection technology using SELEX method. The aptamer can be synthesized chemically, easily resynthesized, and is inexpensive, and can be used for highly specific diagnosis. In particular, the RNA aptamer has several characteristics that it is capable of stabilized structure formation and reversible denaturation, it does not cause immunoreaction that is a main limitation of antibody, and the conditions for binding between the aptamer and a target is controllable. Thus, RNA aptamer can function as a molecule replacing antibody, drug, and the like that can bind to a clinically related target molecule, because it can be easily synthesized, has high affinity and specificity, and does not have immunogenicity, which has been a problem of the use of antibody.

An embodiment provides a novel RNA molecule comprising continuous 35 or more bases essentially comprising the nucleotide sequence from 15$^{th}$ to 50$^{th}$ positions of SEQ ID NO: 18.

<SEQ ID NO: 18>
GGGAGAGCGG AAGCGUGCUG GGCUMGAAUA AUAAUAANRA

AAACCAGWAC UUUCGYGUSC CNRGRVRGDN NCAUAACCCA

GAGGUCGAUG GAUCC wherein,
M is A or C;
N is A or U or G or C or absent (i.e., deleted);
R is G or A;
W is A or U;
Y is U or C;
S is G or C;
V is A or G or C (i.e., not U);
D is A or G or U (i.e., not C); and
each N positioned at 38 and 62 is independently G or C or absent (deleted), and each N positioned at 70 and 71 is independently A or U or G or C.

The minimum number of bases of the nucleotide sequence from 15$^{th}$ to 50$^{th}$ positions of SEQ ID NO: 18 is 35, since N located in the nucleotide sequence from 15$^{th}$ to 50$^{th}$ positions of SEQ ID NO: 18 may be absent (i.e., 'deleted N'); as shown in Example 7, an RNA molecule comprising the 35 bases is capable of specifically binding to CEA; and thus, the nucleotide sequence from 15$^{th}$ to 50$^{th}$ positions of SEQ ID NO: 18 is determined as a minimum functional unit in the present invention.

According to one concrete embodiment, the RNA molecule may comprise a nucleotide sequence selected from the group consisting of SEQ ID NO: 1 to 14. Particularly, the RNA molecule may comprise continuous 35 or more bases essentially comprising the nucleotide sequence from 9$^{th}$ to 43$^{rd}$ positions of SEQ ID NO: 13. The RNA molecule comprising a nucleotide sequence of SEQ ID NO: 13 or 14 has excellent specificity and affinity to CEA, and thus is very useful as RNA aptamer for CEA.

Another embodiment provides a use of the RNA molecule as CEA specific RNA aptamer. Thus, a CEA specific RNA aptamer comprising continuous 35 or more bases essentially comprising the nucleotide sequence from 15$^{th}$ to 50$^{th}$ positions of the SEQ ID NO: 18 is provided. The RNA aptamer specifically binds to a linkage region between N domain and A1 domain of CEA (see Examples 5 to 7). The linkage region between N domain and A1 domain of CEA may comprise 5 amino acids, 'PELPK'.

The RNA aptamer may comprise a polynucleotide selected from the group consisting of SEQ ID NO: 1 to 14. Particularly, the RNA molecule may comprise continuous 35 or more bases comprising a 9 to 43 polynucleotide of SEQ ID NO: 13. The RNA molecule comprising a polynucleotide of SEQ ID NO: 13 or 14 has excellent specificity and affinity to CEA, and thus is very useful as RNA aptamer to CEA.

For allowing resistance to RNase, the RNA aptamer may be modified in several manners. For example, pyrimidine bases C (cytosine) and U (uracil) wherein 2'hydroxyl group is substituted with a fluoro group may be used, and/or a cholesterol or polyethyleneglycol (PEG; weight average molecular weight: 100 to 1,000,000 Da, preferably 1000 to 100,000 Da, more preferably 10,000 to 70,000 Da) molecule may be attached to 5' end of the RNA aptamer and inverted dT (idT) may be attached to 3' end. In particular, when the RNA aptamer is conjugated with polyethyleneglycol at its 5' end, the in vivo availability and resistance to RNase attack of the RNA aptamer is much considerably increased (see Example 17). Therefore, a preferable embodiment may provide a RNA aptamer consists of the nucleotide sequence of SEQ ID NO: 13 or 14, and modified by conjugating with polyethyleneglycol at 5' end and attaching idT (inverted deoxy thymidylate) at 3' end, and C (cytosine) and U (uracil) in the RNA aptamer is modified by substituting 2' hydroxyl group with fluoro group.

As explained, the linkage region (for example, PELPK) between N domain and A1 domain of CEA is recognized by the receptor on other organ's cells, in particular by the receptor on kupffer cell, and plays an important function for metastasis of CEA-expressing cell to other organs, in particular liver. Therefore, the RNA aptamer binding to the region may be useful for inhibition or diagnosis of metastasis of CEA-expressing cell to other organs, particularly liver.

Accordingly, another embodiment provides a composition for inhibition and/or prevention of cancer metastasis containing the RNA aptamer as an active ingredient, and a method of inhibition and/or prevention of cancer metastasis comprising the step of administering the RNA aptamer to a patient in need of inhibition and/or prevention of cnacer metastasis. The method may further comprise the step of identifying a patient in need of inhibition and/or prevention of cnacer metastasis, prior to the step of administering.

The RNA aptamer may comprise a nucleotide sequence selected from the group consisting of SEQ ID NO: 1 to 14, and as explained, it may be modified for resistance to RNase, as described above. That is pyrimidine bases C (cytosine) and U (uracil) wherein 2'hydroxyl group is substituted with a fluoro group may be used, and/or a cholesterol or polyethyleneglycol (PEG; weight average molecular weight: 100 to 1,000,000 Da, preferably 1000 to 100,000 Da, more preferably 10,000 to 70,000 Da) molecule may be attached to 5' end of the RNA aptamer and inverted dT (idT) may be attached to 3' end. As described above, in particular, when the RNA aptamer is conjugated with polyethyleneglycol at its 5' end, the in vivo availability and resistance to RNase attack of the RNA aptamer is much considerably increased (see Example 17). Therefore, a preferable embodiment may provide a method of inhibition and/or prevention of cancer metastasis comprising the step of administering the RNA aptamer to a patient in need of inhibition and/or prevention of cancer metastasis, wherein the RNA aptamer consists of the nucleotide sequence of SEQ ID NO: 13 or 14, and modified by conjugating with polyethyleneglycol at 5' end and attaching idT (inverted deoxy thymidylate) at 3' end, and C (cytosine) and U (uracil) in the RNA aptamer is modified by substituting 2' hydroxyl group with fluoro group.

The cancer on which the RNA aptamer has the effect of metastasis inhibition/prevention may be any CEA-related cancer, and for example, it may be selected from the group consisting of colon cancer, stomach cancer, pancreatic cancer, lung cancer, etc., but not limited thereto. The metastasis, on which the RNA aptamer has the inhibition/prevention effect, may be one to any organ capable of recognizing CEA, for example, liver. Preferably, the RNA aptamer may be useful for inhibition of metastasis of colon cancer to liver.

The RNA aptamer may be administered to any mammals, preferably rodents, livestock, human, etc., and more preferably human. A route of administration is not specifically limited and any administration route may be used. For example, it may be administered orally, intravenously, intramuscularly, subcutaneously, and preferably it may be administered to the affected part by intravenous injection. The RNA aptamer may be administered together with commonly used additives such as pharmaceutically acceptable carrier, excipient, and/or diluents.

A dose of RNA aptamer may be within the range not showing liver toxicity, and it may be commonly administered in the amount of 100 ug/kg (body weight) to 2000 ug/kg (body weight) per a day, preferably 500 ug/kg (body weight) to 1000 ug/kg (body weight) per a day, and more preferably about 800 ug/kg (body weight) per a day, but the dose may be appropriately adjusted depending on the age, body weight and severity of disease of patient.

Another embodiment provides a composition for diagnosis of cancer metastasis containing the RNA aptamer, and a method of diagnosis of cancer metastasis using the RNA aptamer. The RNA aptamer may comprise the nucleotide sequence selected from the group consisting of SEQ ID NO: 1 to 14, and as described, it may be modified for resistance to RNase.

The cancer on which the RNA aptamer has metastasis inhibition effect may be any CEA-related cancer, for example, it may be selected from the group consisting of colon cancer, stomach cancer, pancreatic cancer, lung cancer, etc., but not limited thereto. The metastasis, on which the RNA aptamer has inhibition effect, may be one to any organ capable of recognizing CEA, for example, liver. Preferably, the RNA aptamer may be useful for inhibition of metastasis of colon cancer to liver.

According to one concrete embodiment, the method of diagnosis of metastasis comprises treating a sample or a patient with the RNA aptamer, and detecting binding of the RNA aptamer and CEA (Carcinoembryonic antigen), more particularly a linkage region between N domain and A1 domain, wherein it is determined that metastasis occurs when the binding is detected.

The binding of the RNA aptamer and CEA may be detected by any conventional means, and for example, RNA aptamer may be conventionally labeled and detected. The label may be any conventional fluorescences, radioisotopes, etc., and the fluorescences or radioisotopes may be detected by common detection means (for example, Radio immune guided surgery (RIGS), Radioimmunodetection (RAID), etc.) to determine binding of the RNA aptamer and CEA.

The RNA aptamer may be useful for in vivo diagnosis as well as ex vivo diagnosis, and it may be directly applied to a living body as well as be applied to a tissue or cell separated from mammals, preferably human, to diagnose cancer metastasis.

Another embodiment provides a method of molecular imaging using the RNA aptamer to trace and visualize cancer cell.

More specifically, the molecular imaging method may comprise applying the above RNA aptamer that is labeled with a fluorescence or radioisotope to a living body or an isolated tissue or cell; and detecting the fluorescence or radioisotope.

By labeling the RNA aptamer with conventional fluorescence or radioisotope, applying it to a living body or an isolated tissue or cell of mammals including human (for example, by intravenous administration, etc) and detecting the fluorescence or radioisotope by a conventional method, CEA-expressing cancer cell can be traced and the location and distribution thereof can be visualized (for example, see FIGS. 15 to 17). The CEA-expressing cancer cell may be a cancer cell of caner selected from the group consisting of colon cancer, stomach cancer, pancreatic cancer, lung cancer, etc.

BRIEF DESCRIPTION OF DRAWINGS

FIG. 4 is a sensogram of optimized RNA aptamer.

FIG. 5 shows 5'-cholesterol-modified RNA aptamer for CEA.

FIG. 13 is a graph showing the result of In vitro cell migration assay.

EXAMPLE

Figure 1:
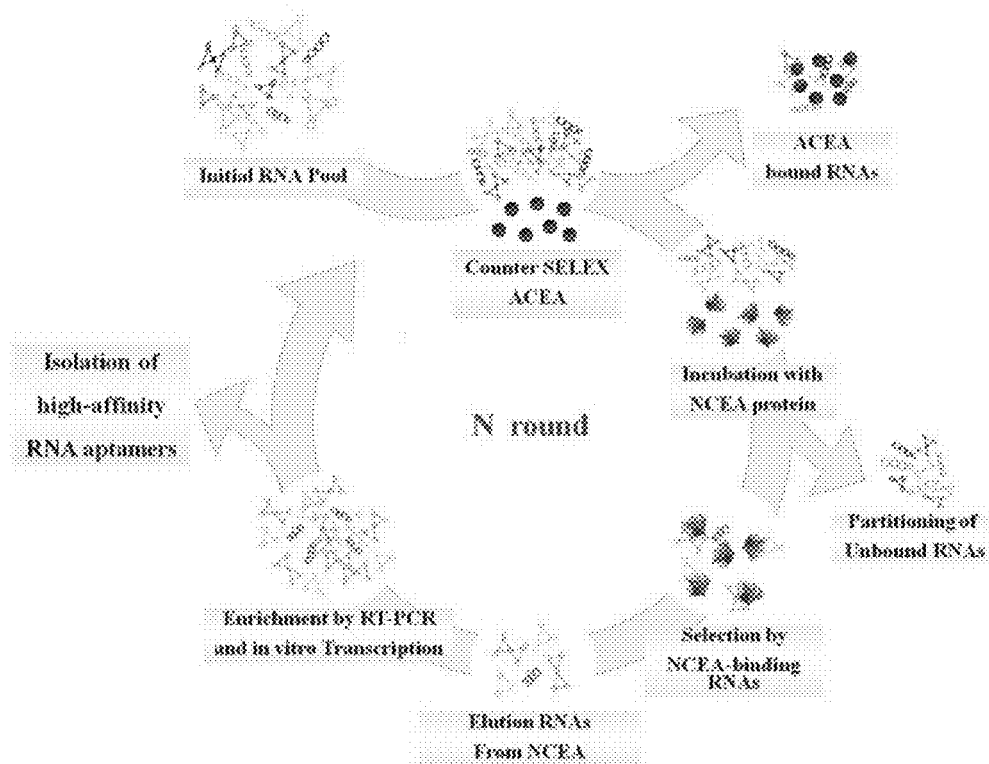
FIG. 1 is an overview of SELEX procedure for CEA.

The present invention is further explained in more detail with reference to the following examples. These examples, however, should not be interpreted as limiting the scope of the present invention in any manner.

Example 1

Preparation of CEA protein 1.1: Construction of Protein

CEA protein was constructed by preparing the following primers based on Full CEACAM5 (CEACAM5 NCBI accession number: NP_004354) and cloning:

Full-CEA-5'-primer:
(SEQ ID NO: 19)
5'-CCCAAGCTTAGACCATGGAGTCTCCCTCGGCC-3'

Full-CEA-3'-primer:
(SEQ ID NO: 20)
5'-GCTCTAGACTATATCAGAGCAACCCCAACCAGCACTCCAATCAT-3'

Vector DNA was purified through Midiprep procedure using Midiprep kit (Promega, PureYield™ Plasmid Midiprep System).

To purify protein (N.CEA) consisting of N domain to B3 domain, N domain-specific primer was used as 5'-primer, and B3 domain-specific primer was used as 3'-primer.

N domain 5'-primer:
(SEQ ID NO: 21)
5'-CGAATTCAAGCTCACTATTGAATCCA-3'

B3 domain 3'-primer:
(SEQ ID NO: 22)
5'-CCCAAGCTTCTAAGATGCAGAGACTGTGAT-3'

To purify protein (A.CEA) consisting of A1 domain to B3 domain, A1 domain-specific primer was used as 5'-primer, and B3 domain-specific primer was used as 3'-primer:

A1 domain 5'-primer:
(SEQ ID NO: 23)
5'-CGAATTCAAGCCCTCCATCTCCAGCAA-3'

B3 domain 3'-primer:
(SEQ ID NO: 22)
5'-CCCAAGCTTCTAAGATGCAGAGACTGTGAT-3'

To purify N domain protein, N domain-specific primer was used as 5'-primer, and N domain-specific primer was used as 3-'primer.

N domain 5'-primer:
(SEQ ID NO: 21)
5'-CGAATTCAAGCTCACTATTGAATCCA-3'

N domain 3'-primer:
(SEQ ID NO: 24)
5'-CCCAAGCTTCTACAGCTCCGGGTATACCCGGA-3'

To purify A1 domain protein, A1 domain-specific primer was used as 5'-primer, and A1 domain-specific primer was used as 3'-primer:

A1 domain 5'-primer:
(SEQ ID NO: 23)
5'-CGAATTCAAGCCCTCCATCTCCAGCAA-3'

A1 domain 3'-primer:
(SEQ ID NO: 25)
5'-CCCAAGCTTCTACGGGCCATAGAGGACATT-3'

To purify protein consisting of N domain and A1 domain, N domain-specific primer was used as 5'-primer, and A1 domain-specific primer was used as 3'-primer:

N domain 5'-primer:
(SEQ ID NO: 21)
5'-CGAATTCAAGCTCACTATTGAATCCA-3'

A1 domain 3'-primer:
(SEQ ID NO: 25)
5'-CCCAAGCTTCTACGGGCCATAGAGGACATT-3'

To construct mutant protein wherein 5 amino acids PELPK of the linkage region between N domain and A1 domain are converted to RELSK, a two-step procedure was conducted (See Tuerk, C., Gold, L. (1990) Systematic evolution of ligands by exponential enrichment:RNA ligands to bacteriophage T4 DNA polymerase. Science, 249, 505-510). As 5'-primer, 5'-TGGCCAGTTCCGGGTATA CCGGGAGCT-GTCCAAGCCCTCCATCTCCAGC-3'(SEQ ID NO: 26) with 2 mutated nucleic acids was used, and as 3'-primer, 5'-GCTGGAGATGGAGGGCTTGGACAGCTC-CCGGTATACCCGGAACTGGCCA-3'(SEQ ID NO: 27) with 2 mutated nucleic acids was used. After conducting PCR, DNA was eluted and it was used as a template to conduct PCR under the following conditions.

Repeat (95° C. 30 seconds, 58° C. 30 seconds, 72° C. 1 minute 30 seconds) 30 times All of the above structures were cloned into pET28a(+) vector (Novagen) using EcoR I and Hind III restriction enzyme (Roche Applied Science), and then, transformed into BL21 *Escherichia coli* (Invitrogen) by heat shock. Base sequence was identified by sequencing analysis.

1.2: Extraction of Protein

A 5 ml LB medium (tryptone 10 g/liter NaCl 10 g/liter yeast extract 5 g/liter (BD biosciences)) was inoculated with each protein stock prepared in Example 1.1, and grown at 37° C. for 16 hours to 18 hours. And then, a 500 ml LB medium was inoculated with the above 5 ml, and incubated at 37° C. until OD value reaches 0.6 to 0.8.

Protein extraction conditions included temperature, culture time, and IPTG (Isopropyl β-D-1-thiogalactopyranoside) concentration as described in TABLE 1. Cell lysis and sonication were conducted, and protein was eluted with controlling imidazole concentration (3-4 eluted proteins were obtained with elution buffer of imidazole concentration of 50 mM, 100 mM, and 250 mM, at each concentration), and concentrated and quantified by Bradford analysis.

TABLE 1

| protein extraction condition | | | |
|---|---|---|---|
|  | Temperature | Culture time | IPTG concentration |
| NCEA(Full length CEA) | 30° C. | 7 hrs | 2.5 mM |
| ACEA(N domain-deleted CEA) | 30° C. | 7 hrs | 2 mM |
| N only | 30° C. | 6 hrs | 1 mM |
| A1 only | 30° C. | 7 hrs | 0.5 mM |
| N + A1 domain | 37° C. | 7 hrs | 1 mM |
| Mut. N + A1 domain | 30° C. | 6 hrs | 1 mM |

Example 2

Construction of DNA Library

To construct a RNA library required for conducting SELEX procedure, according to a commonly known method, using a 76 mer single oligonucleotide randomly including 40 bases as a template, a DNA library was constructed through PCR with 5'-primer(GGTAATACGACTCACTATAGG-GAGAGCGGAAGCGTGCTGGG, SEQ ID NO: 28) and 3'-primer(GGGGGGATCCATCGACCTCTGGGTTATG, SEQ ID NO: 29). The 5'-primer includes T7 RNA region for synthesizing RNA.

0.25 μM 5'-primer, 0.25 μM 3'-primer, 10×PCR buffer (Promega), and 100 μM dNTP mixture (Roche Applied Science) were mixed, and 2.5 unit Taq polymerase (Promega) was added at initial 95° C., 5 minutes. And, as PCR cycles, 10 cycles of 95° C. 30 seconds, 55° C. 30 seconds, and 72° C. 1 minutes were repeated, and then, finally, 72° C. 8 minutes 30 seconds, to construct various DNA libraries.

Example 3

Construction of RNA Library

Using the DNA library with various base sequences constructed though PCR in Example 2 as a template, a RNA library was constructed through in vitro transcription. At this time, in order to prepare RNA resistant to RNase, by transcription of a template synthesized in vitro using 2'-deoxy-2'-fluoro CTP and UTP (Epicentre Technologies), normal GTP and ATP, and T7 RNA polymerase, RNA with each 2 position of pyrimidine nucleotide modified to fluoro group was produced (See Gold, L., Polisky, B., Uhlenbeck, O., Yarus, M. (1995) Diversity of oligonucleotide functions. Annu. Rev. Biochem. 64, 763-797).

The DNA library, 10× transcription buffer, 50 mM DTT, 5 mM ATP, 5 mM GTP, 5 mM 2'-F-CTP, 5 mM 2'-F-UTP, T7 RNA polymerase (Epicentre Technologies), DEPC-H2O (DiethylenePyrocarbonate-H2O) were used to adjust reaction volume to 20λ, and they were reacted at 37° C. for 6 hours. The reactant was treated with 1 MBU DNaseI (Epicentre Technologies) at 37° C. for 15 minutes to remove DNA used as template. An RNA library was eluted using Sephadex G25 column (sigma). RNA obtained through selection procedure was eluted from 7M urea-6% polyacrylamide gel.

Example 4

Selection of N+A1 Domain Specific RNA Aptamer

To detect RNA aptamers specifically binding to a specific CEA domain related to metastasis, which is used as a metastasis inhibitor according to the present invention, a counter selection method of removing ACEA-bound RNAs and then detecting NCEA-binding RNAs was used. FIG. 1 is a schematic drawing of SELEX procedure to CEA.

First, a preclearing step of removing ACEA-bound RNAs was conducted, and then, RNAs capable of specifically binding to NCEA was detected, thereby selecting RNA aptamers that can specifically bind to a specific domain (N+A1 domain) of CEA, which is used for a metastasis inhibitor of the present invention.

The RNA library constructed in Example 3 and ACEA constructed in Example 1 were reacted at room temperature for 20 minutes. And, Ni-NTA agarose beads (QIAGEN) were rapidly spinned and washed with binding buffer (30 mM Tris-HCl (PH 7.5), 150 mM NaCl, 1.5 mM MgCl2, 2 mM DTT, 1% BSA), and then, reacted with the above reactant at room temperature for 20 minutes. After the reaction, only supernatant was taken and reacted with NCEA at room temperature for 20 minutes. Ni-NTA agarose beads (QIAGEN) washed by rapid spinning were taped together and reacted. Ni-NTA agarose beads (QIAGEN) and RNA and protein complex was washed with binding buffer (30 mM Tris-HCl (PH 7.5), 150 mM NaCl, 1.5 mM MgCl2, 2 mM DTT, 1% BSA) 5 times repeatedly. And then, it was dissolved in TE buffer (10 mM Tris-Cl, pH 7.5, 1 mM EDTA (Sigma)), and NCEA-binding RNAs were eluted by phenol extraction and concentrated by ethanol precipitation.

SELEX 1st round was conducted as explained, and from 2nd round, NCEA-binding RNAs were amplified by the following method and used in the next cycle.

Into RNAs obtained through each cycle of SELEX, 500 nM of 3'-primer (5'-GGGGGGATCCATCGACCTCTGGGT-TATG-3, SEQ ID NO: 29) was introduced, and denatured at 65° C. for 5 minutes, and then, left at room temperature for 10 minutes to bind RNA with the primer. 1 mM dNTP, 5×RT buffer (promega), and 25 U AMV RTase(promega) were added and reacted at 37° C. for 30 minutes, and then, heated at 95° C. for 5 minutes, and cooled at 4° C. to inactivate reverse transcriptase. Synthesized cDNA was amplified by PCR. DNA obtained by reverse transcription-PCR was identified by 3% agarose gel, and RNA was synthesized again through in vitro transcription by the same method as constructing RNA library and used in the next selection process.

SELEX was conducted total 17 rounds. $1^{st}$ to $5^{th}$ rounds were conducted with the mole ratio of NCEA:ACEA:RNA of 1:2:2, and $6^{th}$ to $15^{th}$ rounds were conducted with the mole ratio of NCEA:ACEA:RNA of 1:10:2, thereby providing reliability to the counter selection procedure for removing RNAs nonspecifically binding to ACEA. $16^{th}$ to $17^{th}$ rounds were conducted with the mole ratio of NCEA:ACEA:RNA of 1:10:1 to finally remove RNAs capable of binding to ACEA.

TABLE 2

SELEX Condition

| Round | RNA | Protein (ACEA) | Protein (NCEA) |
|---|---|---|---|
| 1st | 5 µg(150 pmole) | 8 µg(138 pmole) | 5 µg(70 pmole) |
| $2^{nd}$ | 5 µg(150 pmole) | 8 µg(138 pmole) | 5 µg(70 pmole) |
| 3rd | 5 µg(150 pmole) | 8 µg(138 pmole) | 5 µg(70 pmole) |
| 4th | 5 µg(150 pmole) | 8 µg(138 pmole) | 5 µg(70 pmole) |
| 5th | 5 µg(150 pmole) | 8 µg(138 pmole) | 5 µg(70 pmole) |
| 6th | 1 µg(30 pmole) | 8 µg(138 pmole) | 1 µg(14 pmole) |
| 7th | 1 µg(30 pmole) | 8 µg(138 pmole) | 1 µg(14 pmole) |
| 8th | 1 µg(30 pmole) | 8 µg(138 pmole) | 1 µg(14 pmole) |
| 9th | 1 µg(30 pmole) | 8 µg(138 pmole) | 1 µg(14 pmole) |
| 10th | 1 µg(30 pmole) | 8 µg(138 pmole) | 1 µg(14 pmole) |
| 11th | 1 µg(30 pmole) | 8 µg(138 pmole) | 1 µg(14 pmole) |
| 12th | 1 µg(30 pmole) | 8 µg(138 pmole) | 1 µg(14 pmole) |
| 13th | 1 µg(30 pmole) | 8 µg(138 pmole) | 1 µg(14 pmole) |
| 14th | 1 µg(30 pmole) | 8 µg(138 pmole) | 1 µg(14 pmole) |
| 15th | 1 µg(30 pmole) | 8 µg(138 pmole) | 1 µg(14 pmole) |
| 16th | 500 ng(15 pmole) | 8 µg(138 pmole) | 1 µg(14 pmole) |
| 17th | 500 ng(15 pmole) | 8 µg(138 pmole) | 1 µg(14 pmole) |

Figure 2A:
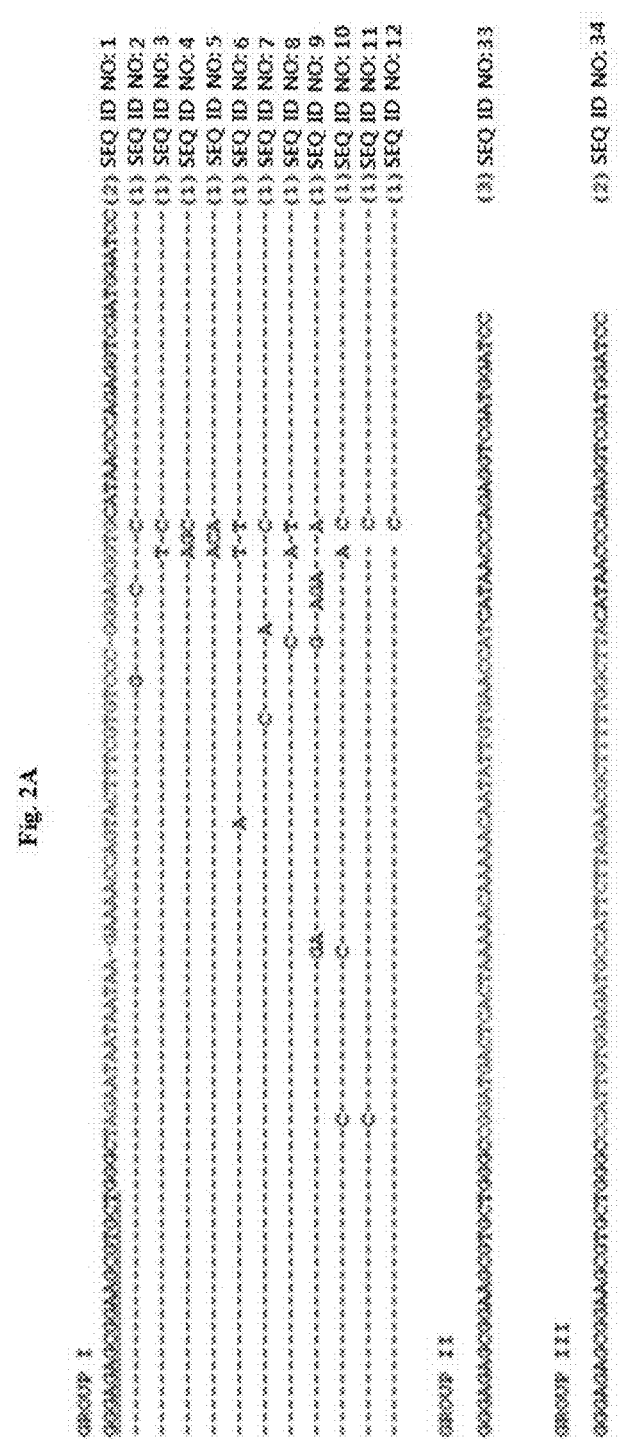
Figure 2B:
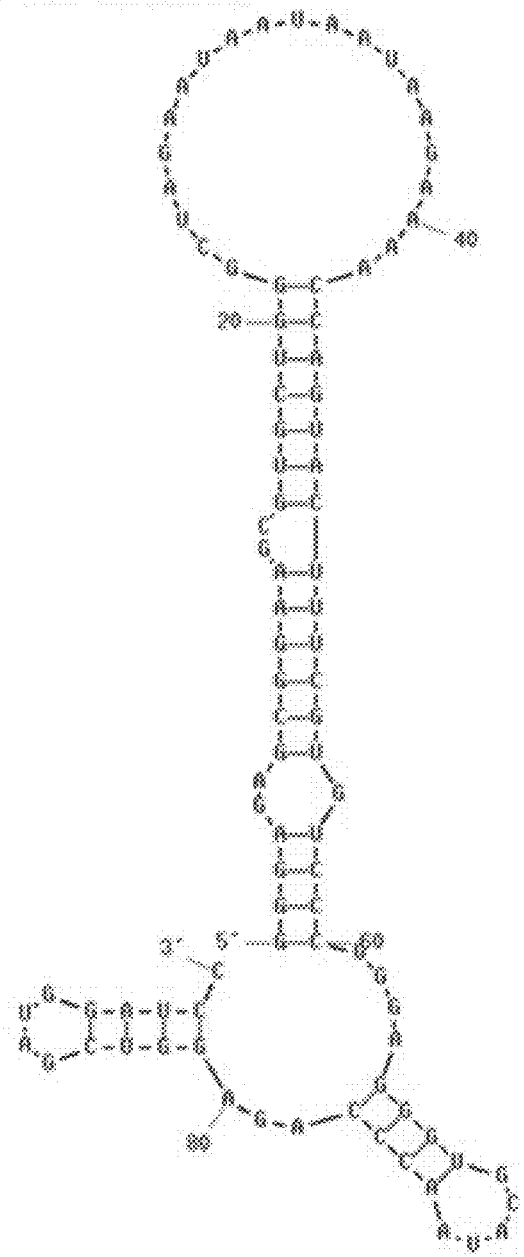
FIG. 2A shows nucleotide sequences of selected RNAs, and 2B-2D show secondary structures thereof.
Figure 2C:
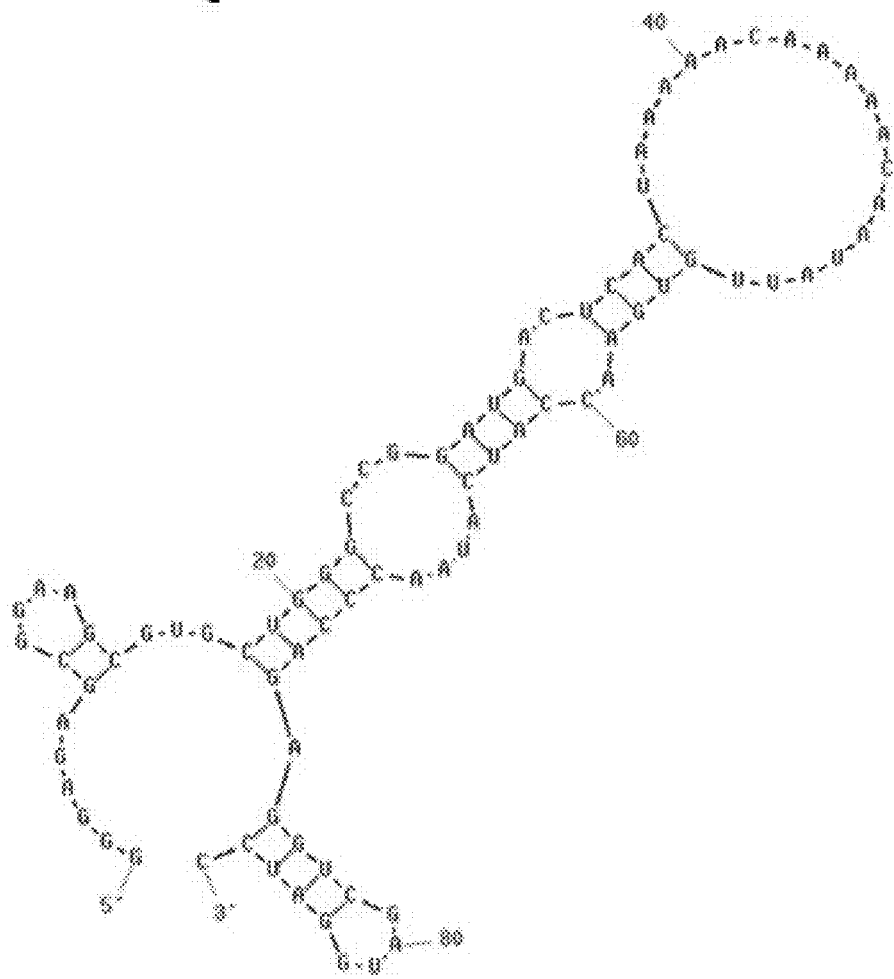
Figure 2D:
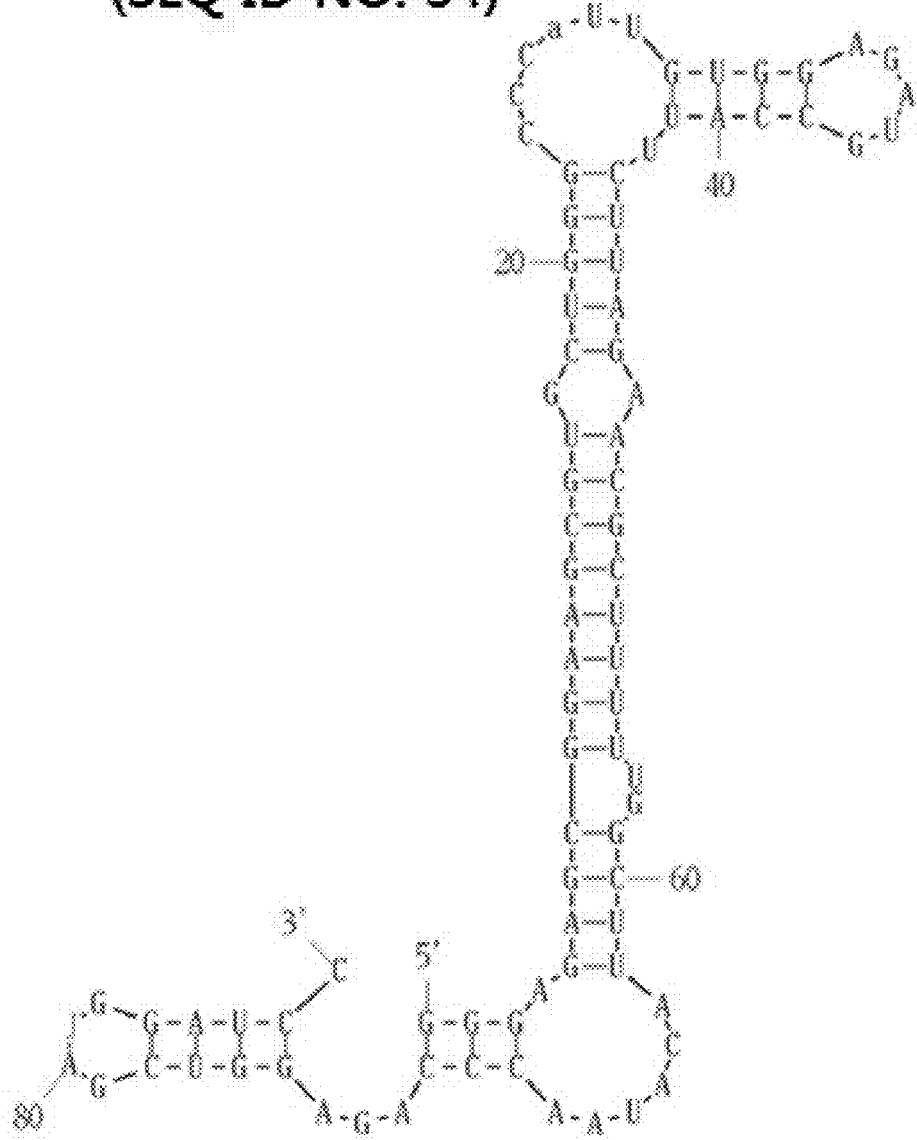
Figure 3B:
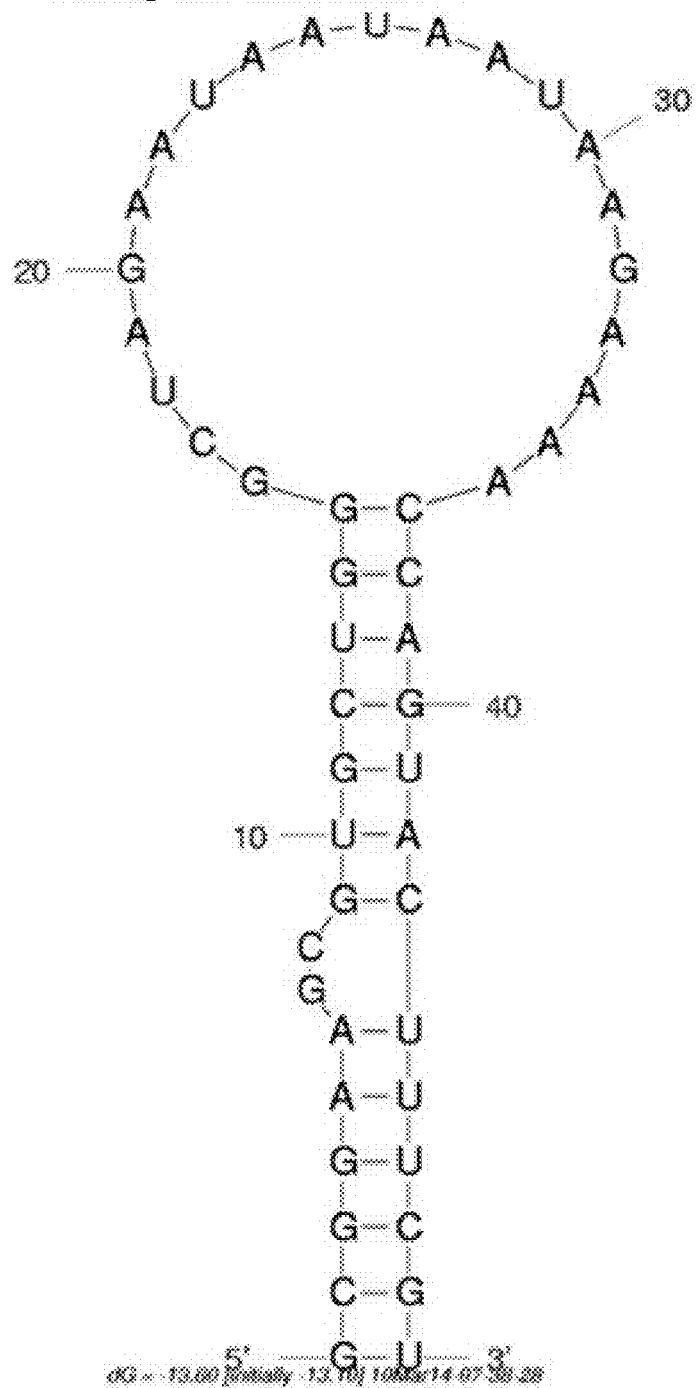
FIG. 3A shows nucleotide sequences of optimized RNA, and 3B-3F show secondary structures thereof.
Figure 3C:
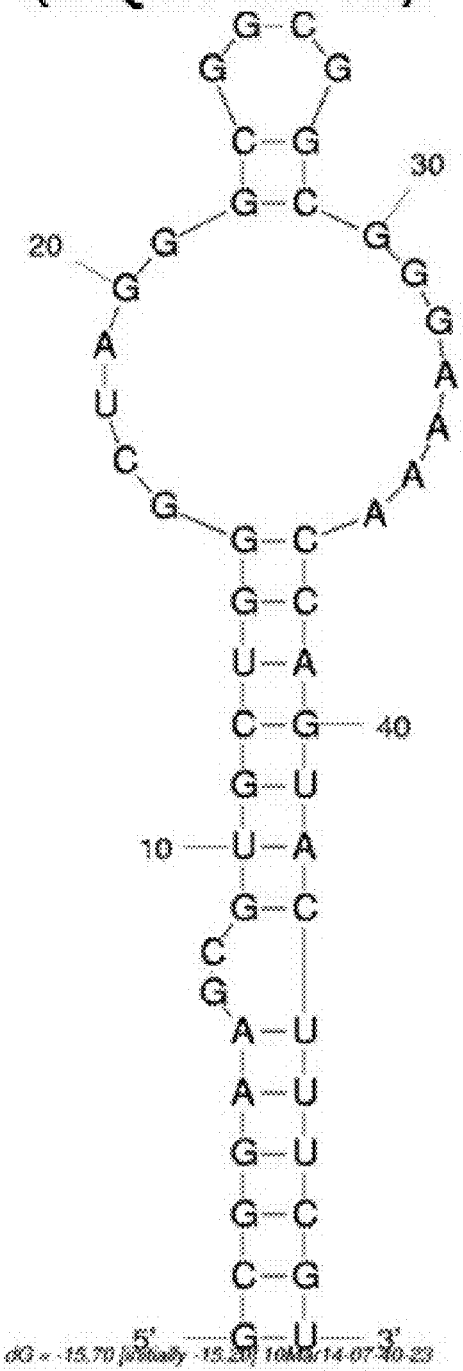
Figure 3E:
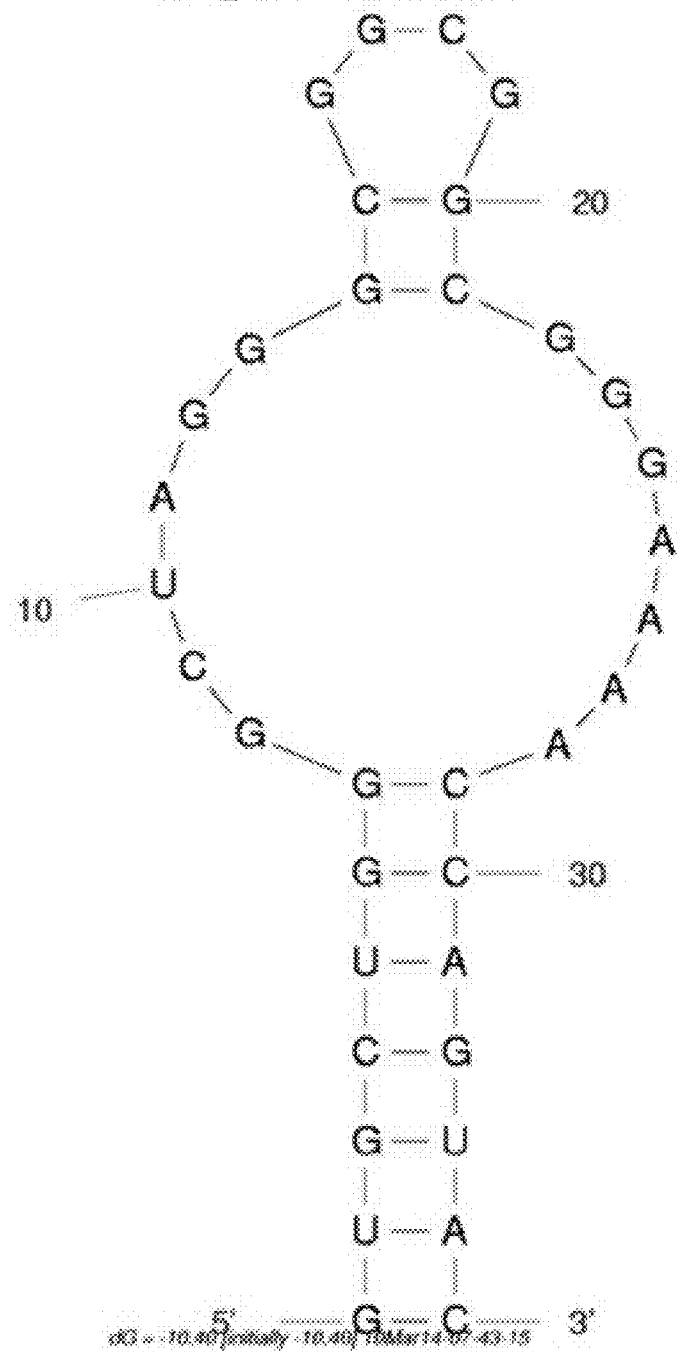
Figure 3F:
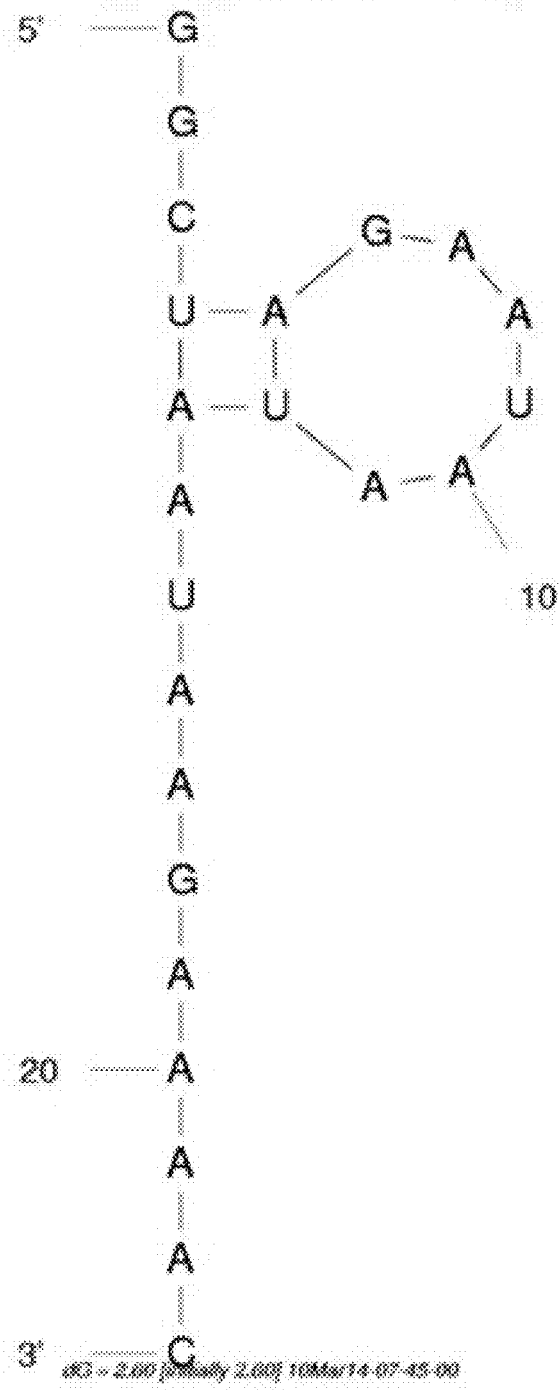

17 rounds SELEX was conducted to obtain 3 groups of RNAs with polynucleotide similarity, and the result was shown in FIG. 2A. It can be seen that the ratio of GROUP 1 RNAs are 70% or more. Secondary structures of the obtained RNAs of each GROUP were expected using mFold (Mfold web server for nucleic acid folding and hybridization prediction. *Nucleic Acids Res.* 31 (13), 3406-15, (2003)), and shown in FIG. 2B-2D.

Example 5

Measurement of Affinity of Selected RNAs to CEA

To measure the affinity of RNA to CEA, SPR analysis was performed with Biacore 2000 (GE healthcare) device. Various concentrations of RNAs (GROUP 1, 2, 3 and library in FIG. 2) were flowed on NCEA and ACEA to measure the binding affinity.

It is confirmed that GROUP 1 has the highest affinity to NCEA and shows 10 times lower KD compared to ACEA, indicating that GROUP 1 is an RNA aptamer specific to NCEA of CEA with high affinity thereto. Meanwhile, it is confirmed that GROUPs 2 and 3 have the affinity to NCEA of about 5 times (GROUP 2) or about 3 times (GROUP 3) compared to ACEA (TABLE 3).

TABLE 3

Affinity of each GROUP to NCEA and ACEA

| | ka (1/Ms) | kd (1/s) | KA (1/M) | KD (M) | Chi2 |
|---|---|---|---|---|---|
| GROUP I to NCEA | 5.27E+05 ± 6.29E+04 | 1.68E−04 ± 6.58E−05 | 3.33E+09 ± 9.26E+08 | 3.13E−10 ± 8.77E−11 | 6.19E+00 ± 1.51E+00 |
| GROUP I to ACEA | 3.90E+05 ± 3.29E+05 | 1.25E−03 ± 1.04E−03 | 3.11E+08 ± 4.95E+06 | 3.22E−09 ± 5.66E−11 | 7.07E+00 ± 5.16E−01 |
| GROUP II to NCEA | 4.09E+05 ± 1.13E+05 | 2.40E−04 ± 4.10E−05 | 1.69E+09 ± 1.84E+08 | 5.96E−10 ± 6.58E−11 | 5.21E+00 ± 2.83E−02 |
| GROUP II to ACEA | 4.22E+05 ± 1.41E+05 | 1.15E−03 ± 1.70E−04 | 3.61E+08 ± 7.07E+07 | 2.82E−09 ± 5.52E−10 | 1.07E+00 ± 7.14E−01 |
| GROUP III to NCEA | 2.71E+05 ± 2.83E+03 | 4.04E−04 ± 1.10E−04 | 6.96E+08 ± 1.82E+08 | 1.49E−09 ± 3.89E−10 | 3.82E+00 ± 4.16E+00 |
| GROUP III to ACEA | 3.39E+05 ± 8.70E+04 | 1.39E−03 ± 1.20E−04 | 2.42E+08 ± 4.24E+07 | 4.19E−09 ± 7.35E−10 | 1.94E+00 ± 1.60E+00 |
| LIBRARY to NCEA | 1.31E+05 ± 2.83E+03 | 1.62E−03 ± 1.34E−04 | 8.13E+07 ± 5.02E+06 | 1.24E−08 ± 7.78E−10 | 4.16E+00 ± 7.99E−01 |
| LIBRARY to ACEA | 9.57E+03 ± 7.83E+03 | 7.04E−04 ± 5.46E−04 | 1.33E+07 ± 8.49E+05 | 7.54E−08 ± 4.95E−09 | 4.15E+00 ± 4.23E+00 |

The above value is measured using BIAevaluation program (which is used to analyze graph obtained from BIAcore device).

ka: concentration of analyte binding to the target per an hour kd: concentration of analyte separating from the target per an hour KD: equilibrium constant showing binding strength chi2: a value showing the difference between the calculation value by the BIAevaluation program and data obtained from actual experiment, which should be 10 or less.

12 RNA aptamers of GROUP 1 shown in FIG. 2A highly specifically bind to a linkage region between N domain and A1 domain of CEA, and it can be used for an active ingredient of metastasis inhibitor of the present invention, of which polynucleotide is as shown in the following SEQ ID NO: 1 to SEQ ID NO: 12 (mutated nucleotide is shown in underline).

SEQ ID NO: 1:
GGGAGAGCGGAAGCGUGCUGGGCUAGAAUAAUAAUAAGAAAACC

AGUACUUUCGU GUCCCGGGAGGGUGCAUAACCCAGAGGUCGAUGGAUCC

SEQ ID NO: 2:
GGGAGAGCGGAAGCGUGCUGGGCUAGAAUAAUAAUAAGAAAACC

AGUACUUUCGUGUGCCGGGCGGGUCCAUAACCCAGAGGUCGAUGGAUCC

SEQ ID NO: 3:
GGGAGAGCGGAAGCGUGCUGGGCUAGAAUAAUAAUAAGAAAACC

AGUACUUUCGUGUCCCGGGAGGUUCCAUAACCCAGAGGUCGAUGGAUCC

SEQ ID NO: 4:
GGGAGAGCGGAAGCGUGCUGGGCUAGAAUAAUAAUAAGAAAACC

AGUACUUUCGUGUCCCGGGAGGAGCCAUAACCCAGAGGUCGAUGGAUCC

SEQ ID NO: 5:
GGGAGAGCGGAAGCGUGCUGGGCUAGAAUAAUAAUAAGAAAACC

AGUACUUUCGUGUCCCGGGAGGACACAUAACCCAGAGGUCGAUGGAUCC

SEQ ID NO: 6:
GGGAGAGCGGAAGCGUGCUGGGCUAGAAUAAUAAUAAGAAAACC

AGAACUUUCGUGUCCCGGGAGGUUUCAUAACCCAGAGGUCGAUGGAUCC

SEQ ID NO: 7:
GGGAGAGCGGAAGCGUGCUGGGCUAGAAUAAUAAUAAGAAAACC

AGUACUUUCGCGUCCCAGGAGGGUCCAUAACCCAGAGGUCGAUGGAUCC

SEQ ID NO: 8:
GGGAGAGCGGAAGCGUGCUGGGCUAGAAUAAUAAUAAGAAAACC

AGUACUUUCGUGUCCCCGGGAGGAUUCAUAACCCAGAGGUCGAUGGAUCC

SEQ ID NO: 9:
GGGAGAGCGGAAGCGUGCUGGGCUAGAAUAAUAAUAAGAAAAC

CAGUACUUUCGUGUCCCGGGAGAGGUACAUAACCCAGAGGUCGAUGGAUCC

SEQ ID NO: 10:
GGGAGAGCGGAAGCGUGCUGGGCUCGAAUAAUAAUAACGAAAACC

AGUACUUUCGUGUCCCGGGAGGACCAUAACCCAGAGGUCGAUGGAUCC

SEQ ID NO: 11:
GGGAGAGCGGAAGCGUGCUGGGCUCGAAUAAUAAUAAGAAAACC

AGUACUUUCGUGUCCCGGGAGGGCCAUAACCCAGAGGUCGAUGGAUCC

SEQ ID NO: 12:
GGGAGAGCGGAAGCGUGCUGGGCUAGAAUAAUAAUAAGAAAACC

AGUACUUUCGUGUCCCGGGAGGGCCAUAACCCAGAGGUCGAUGGAUCC

Example 6

Optimization of RNA Aptamer Specifically Binding to CEA

The length of GROUP1 showing the highest affinity in the above experiment was optimized so as to be suitable for chemical synthesis. And, mutant series wherein a Loop part that is expected to be responsible for binding to a target protein, NCEA, is mutated, were constructed as follows (See FIGS. 3A-3F).

Truncated GROUP 1-1 (49mer):
(SEQ ID NO: 13)
GCGGAAGCGUGCUGGGCUAGAAUAAUAAUAAGAAAACCAGUACUUUCGU -continued Truncated GROUP 1-2 (35mer):
(SEQ ID NO: 14)
GUGCUG*GGCUAGAAUAAUAAUAAGAAAAC*CAGUAC Mutant GROUP 1-1 (49mer):
(SEQ ID NO: 15)
GCGGAAGCGUGCUG*GGCUAGGGCGGCGGCGGG*AAAACCAGUACUUUCGU Mutant GROUP 1-2 (35mer):
(SEQ ID NO: 16)
GUGCUG*GGCUAGGGCGGCGGCGGG*AAAACCAGUAC Loop only (23mer):
(SEQ ID NO: 17)
*GGCUAGAAUAAUAAUAAGAAAAC*
(Nucleotide in italic: loop part corresponding to SEQ ID NO: 17
Nucleotide in underline: mutated part)

Example 7

Measurement of Affinity of RNA Aptamer to CEA

To measure the affinity of RNA aptamer to CEA, SPR analysis was performed with Biacore 2000 (GE healthcare) device. Various concentrations of RNAs (Trunc. GROUP 1-1 & 1-2 and Mutant GROUP 1-1 & 1-2, Loop-only, Library) were flowed on NCEA and ACEA to measure the binding affinity, which is shown in the following TABLE 4 and FIG. 4.

TABLE 4

Affinity of RNA aptamer to NCEA and ACEA

| | ka (1/Ms) | kd (1/s) | KA (1/M) | KD (M) | Chi2 |
|---|---|---|---|---|---|
| 19-1 NCEA | 7.0E+05 ± 1.2E+05 | 5.4E−04 ± 6.5E−05 | 1.3E+09 ± 5.7E+07 | 7.7E−10 ± 3.3E−11 | 5.5E+00 ± 3.1E+00 |
| m19-1 NCEA | 7.6E+00 ± 1.6E−01 | 1.0E−05 ± 0.0E+00 | 7.6E+05 ± 1.6E+04 | 1.3E−06 ± 2.8E−08 | 2.3E+00 ± 3.1E+01 |
| 19-2 NCEA | 3.2E+05 ± 2.4E+05 | 1.3E−03 ± 9.8E−04 | 2.5E+08 ± 5.7E+06 | 4.0E−09 ± 9.2E−11 | 2.3E+00 ± 1.9E+00 |
| m19-2 NCEA | 4.5E+01 ± 3.4E+01 | 1.8E−05 ± 1.1E−05 | 2.4E+06 ± 3.7E+05 | 4.2E−07 ± 6.6E−08 | 5.1E−01 ± 5.6E−02 |
| library NCEA | 4.8E+00 ± 1.4E+00 | 1.0E−05 ± 0.0E+00 | 4.8E+05 ± 1.4E+05 | 2.2E−06 ± 6.3E−07 | 1.2E+00 ± 8.9E−01 |
| loop-only NCEA | 4.2E+00 ± 1.3E+00 | 1.0E−05 ± 0.0E+00 | 4.1E+05 ± 1.3E+05 | 2.5E−06 ± 7.8E−07 | 3.2E+00 ± 2.8E+00 |
| 19-1 ACEA | 7.6E+03 ± 2.1E+03 | 4.6E−03 ± 1.7E−03 | 1.7E+06 ± 1.7E+05 | 6.0E−07 ± 6.0E−08 | 7.6E+00 ± 4.0E−01 |
| m19-1 ACEA | 3.6E+02 ± 5.0E+02 | 2.7E−04 ± 3.6E−04 | 1.3E+06 ± 1.3E+05 | 7.9E−07 ± 8.0E−08 | 4.6E−01 ± 2.3E−01 |
| 19-2 ACEA | 1.9E+03 ± 9.7E+02 | 1.1E−03 ± 5.0E−04 | 1.7E+06 ± 9.2E+04 | 5.9E−07 ± 3.3E−08 | 8.3E+00 ± 9.8E−01 |
| m19-2 ACEA | 1.6E+01 ± 2.1E+00 | 1.0E−05 ± 0.0E+00 | 1.6E+06 ± 2.1E+05 | 6.3E−07 ± 8.1E−08 | 1.6E−01 ± 1.2E−01 |
| library ACEA | 2.3E+00 ± 3.7E−01 | 1.0E−05 ± 0.0E+00 | 2.3E+05 ± 3.6E+04 | 4.5E−06 ± 7.1E−07 | 7.1E−01 ± 2.5E−01 |
| loop-only ACEA | 9.3E+00 ± 4.0E−01 | 1.0E−05 ± 0.0E+00 | 9.2E+05 ± 4.0E+04 | 1.1E−06 ± 4.9E−08 | 5.1E−01 ± 3.4E−01 |

As shown in TABLE 4, it is confirmed that GROUP 1-1 has the highest affinity to NCEA, and shows 780 times lower KD compared to ACEA, indicating that the optimized GROUP 1-1 is specific to NCEA of CEA with strong affinity and can be used as RNA aptamer of the present invention. GROUP 1-2 of smaller size, although has rather decreased affinity to NCEA, has superior affinity to library RNA pool or loop-only. Meanwhile, it is confirmed that library RNA pool or loop-only does not bind to NCEA. It is also confirmed that mutant GROUPs 1-1 & 1-2 with mutated loop parts show weakened binding to NCEA or do not bind thereto. The results mean that a loop part of RNA aptamer is responsible for binding to NCEA.

In conclusion, RNA aptamers of the optimized GROUP 1-1 (SEQ ID NO: 13) and GROUP 1-2 (SEQ ID NO: 14) specifically bind to a linkage region between N domain and A1 domain of CEA, and thus can be used as an active ingredient of the metastasis inhibitor of the present invention.

Example 8

Mass Production of RNA Aptamer Specific to Metastatic Domain of CEA

To prove that the CEA-specific RNA aptamer is a CEA-mediated metastasis inhibitor, the optimized Truncated GROUP 1-1 (SEQ ID NO: 13, 2' of each pyrimidine nucleotide was substituted with fluoro group; hereinafter designated as YJ-1) and its mutant (SEQ ID NO: 15, 2' of each pyrimidine nucleotide was substituted with fluoro group; hereinafter designated as mutant YJ-1) were mass-produced through chemical synthesis.

At this time, to increase in vivo aptamer availability and prevent RNase attack, cholesterol was attached to 5' end of the RNA aptamer and inverted dT (idT) was attached to 3' end. And, 2' of each pyrimidine nucleotide was substituted with fluoro group (see FIG. 5). The synthesized and modified RNA aptamers are designated as cholesterol conjugated YJ-1 (corresponding to SEQ ID NO: 13) and cholesterol conjugated mutant YJ-1 (corresponding to SEQ ID NO: 15), respectively.

To synthesize the modified aptamer, cholesterol conjugated RNA aptamer (cholesterol conjugated YJ-1) and its mutant RNA aptamer(cholesterol conjugated mutant YJ-1) were synthesized with 1 mmol scale using idT CPG (solid support, SAMCHULLY PHARM. CO., LTD.). At this time, cholesterol group was attached to 5' end using Cholesteryl TEG amidite (1-dimethoxytrityloxy-3-O-(N-cholesteryl-3-aminopropyl)-triethyleneglycol-glyceryl-2-O-(2-cyanoethyl)-(N,Ndiisopropyl)-phosphoramidite). The synthesis of cholesterol-attached aptamer conjugate was examined with polyacrylamide gel electrophoresis, HPLC (Agilent 1100, Agilent technologies) and MALDI-TOF (Autoflex MALDI-TOF Mass Spectrometer, Bruker Daltonics), and it was precipitated and desalted with CentriSep (ABI applied biosystems), and finally dissolved in water.

Example 9

Inhibition of CEA-Dependent Cancer Cell Aggregation by RNA Aptamer

CEA-mediated cell aggregation assay was performed to measure aggregation index to see if RNA aptamer (YJ-1, prepared in Example 8) inhibits CEA-mediated cell aggregation between CEA-positive cells (See FIG. 6).

CEA-positive cell lines, i.e., LS174T (CL-188 ATCC (American Type Culture Collection)), LoVo (CCL-229 ATCC), and CAPAN-1 (HTB-79 ATCC) cell lines, and CEA-negative cell lines, i.e., HT29 (HTB-38 ATCC) and MCF7 (HTB-22 ATCC) cell lines, were incubated with each suitable medium (LS174T, MCF7: MEM (Minimum Essential Medium)/10% FBS/1% Antibiotic/Antimycotic Solution; CAPAN-1: RPMI 1640/MEM/20% FBS/1% Antibiotic/Antimycotic Solution; LoVo, HT29: DMEM (Dulbecco's Modified Eagle's Media)/10% FBS/1% Antibiotic/Antimycotic Solution, Thermo Fisher Scientific Inc. (HyClone)) at 37° C., 5% $CO_2$ ($2.5×10^6$ cells/24 hrs).

To confirm the inhibition of CEA-dependent cancer cell aggregation, the above-obtained cells were subcultured once, and separated from the culture dish with Non-enzymatic cell dissociation buffer (sigma), and then, the number of cells was determined with Hemocytometer ($1 \times 10^6$ cells/nil). The obtained cells were treated with each 10 μg/ml of the above-selected RNA aptamers of SEQ ID NO: 13 and SEQ ID NO: 15, and each cell was suspended in 0.4 mM $Ca^{2+}$ treated PBS and non-treated PBS, and then, introduced in a 24 well plate and shaken at 37° C. for 30 minutes at 80 rpm, and then, fixed with 5% glutaraldehyde, and the degree of aggregation was indicated by aggregation index (N30/N0; N0: the number of single cell to total number of aggregated cells at 0 minute, N30: the number of single cell to total number of aggregated cells after 30 minutes of reaction).

Figure 6A:
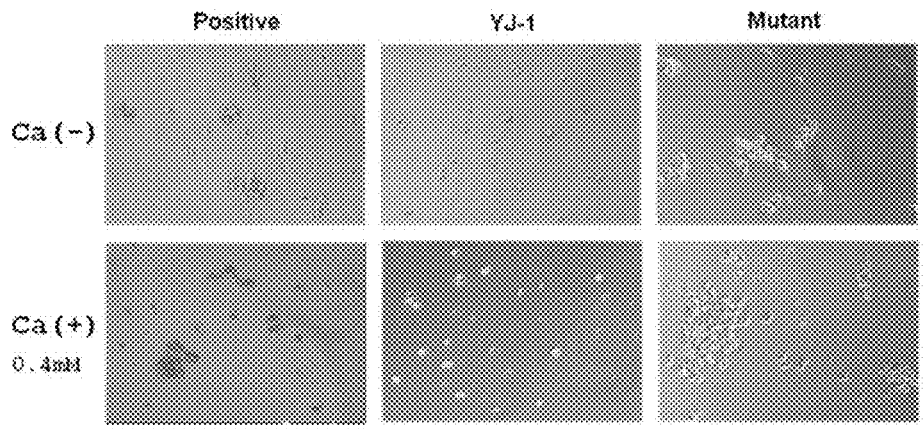
FIGS. 6A-6F show results of homotypic cell aggregation inhibition assay, indicating $Ca^{2+}$-independent inhibition of homotypic cell aggregation by RNA aptamer for CEA.
Figure 6B:
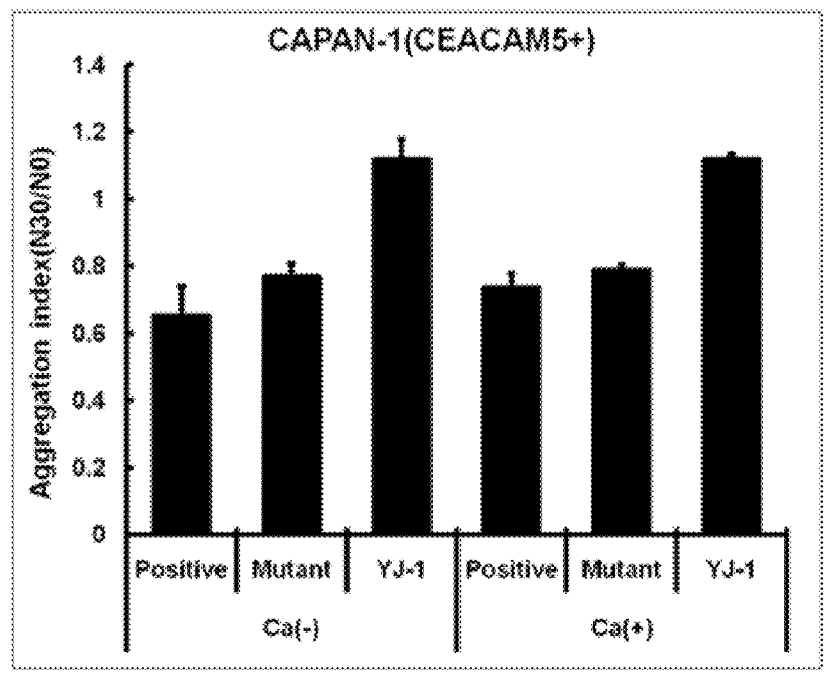
Figure 6C:
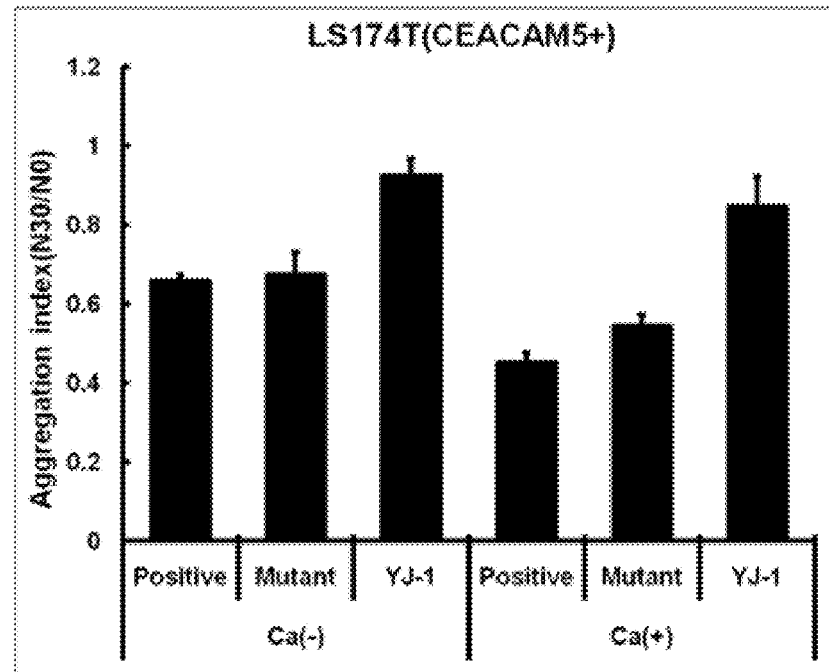
Figure 6D:
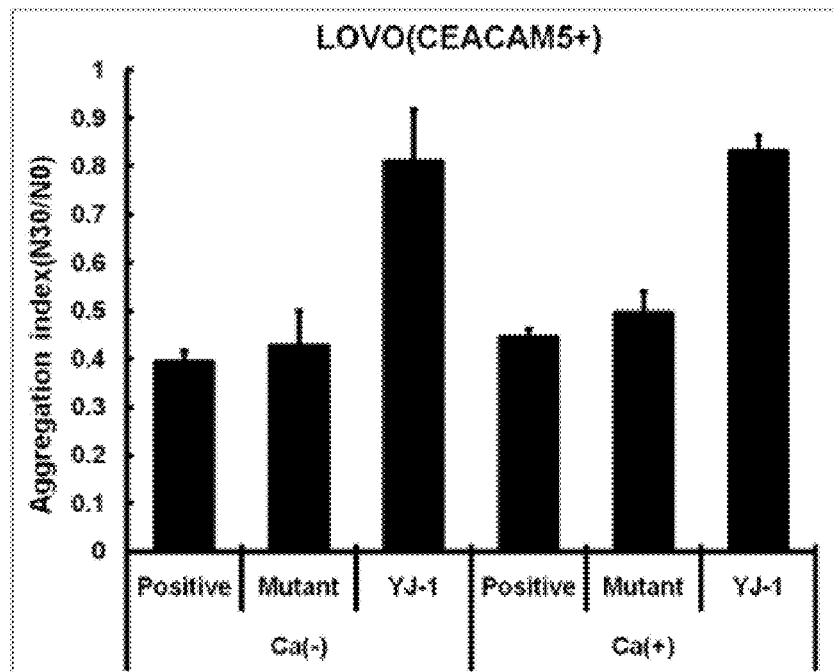
Figure 6E:
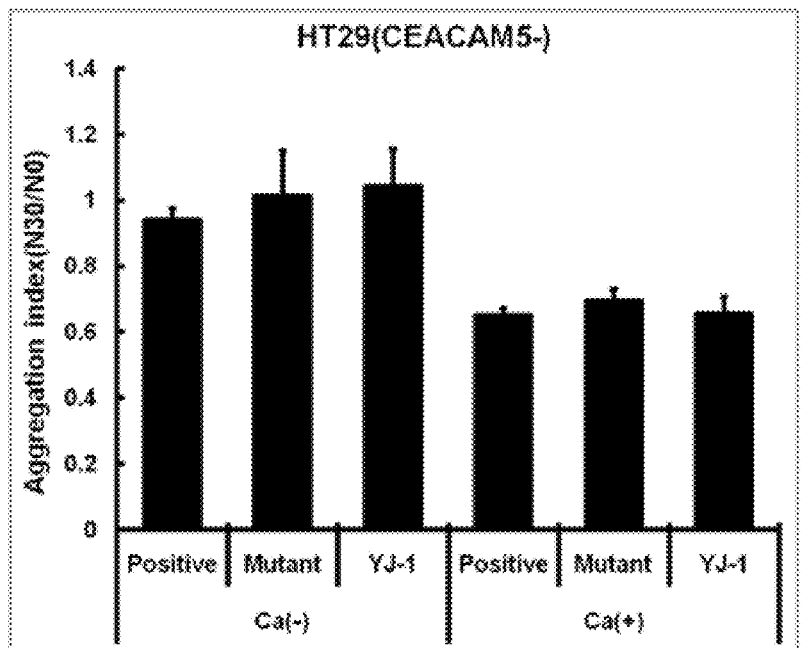
Figure 6F:
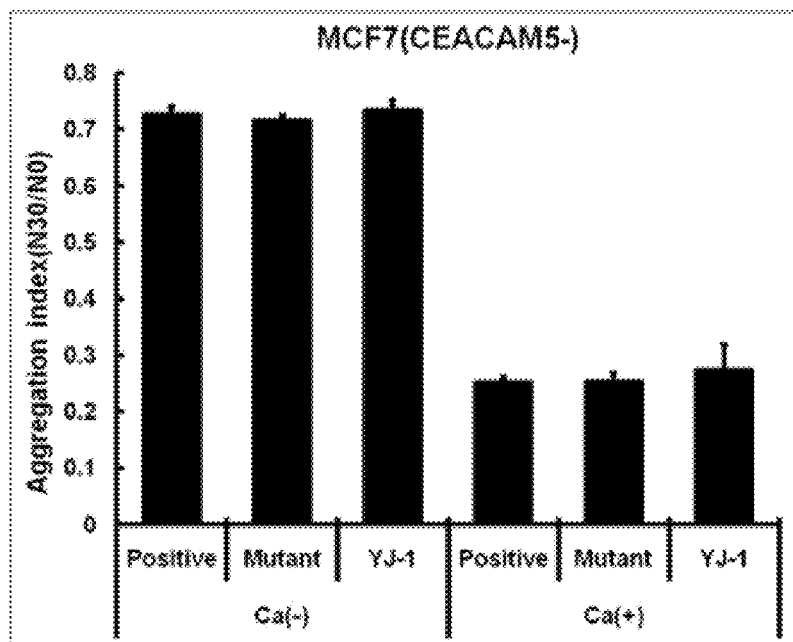

The results were shown in FIGS. 6A-F. FIG. 6A is a photo representatively showing whether or not cell aggregation degree is inhibited depending on the presence of RNA aptamer (YJ-1 or Mutant), and 6B-6F are graphs showing aggregation index (N30/N0) derived by counting 10 photos as the above for each treatment group.

As shown in FIG. 6, in CEA-positive cells, i.e., LS174T, Lovo, and CAPAN cells, cell aggregation is effectively inhibited by RNA aptamer (YJ-1, SEQ ID NO: 13) in a calcium-independent manner, while in CEA-negative cells, i.e., MCF7 and HT-29 cells, cell aggregation increased in a calcium-dependent manner, irrespective of the presence of RNA aptamer (YJ-1, SEQ ID NO: 13, prepared in Example 8).

Example 10

Inhibition of CEA-Dependent In Vitro ECM Adhesion by RNA Aptmaer

To examine whether the selected RNA aptamer can inhibit the adhesion of CEA to extracellular matrix (ECM) component protein, the degree of adhesion to 5 ECM (extracellular matrix) proteins (fibronectin, vitronectin, laminin, collagen I, and collagen IV) were measured. At adhesion reaction of CEACAM5 expressing cancer cell and non-expressing cancer cell with ECM protein, RNA aptamer (300 nM, prepared in Example 8) was incubated together, and then, cancer cells adhered to ECM protein were dyed with a staining solution (0.2% crystal violet in 10% ethanol) and measured to examine the adhesion degree.

More specifically, CEA-positive or negative cells were bound to a plate (Chemicon International Inc. (CytoMatrix™ (5) SCREEN KIT)) coated with the 5 ECM protein (fibronectin, vitronectin, laminin, collagen I and collagen IV). For binding reaction, CEA-positive cell lines, i.e., LS174T, LoVo, SW480 (CCL-228 ATCC) and CAPAN-1 cells lines, and CEA-negative cell lines, i.e., HT29, MCF7, and NIH-3T3 (CRL-1658 ATCC) cell lines were incubated with each appropriate medium (LS174T, MCF7:MEM/10% FBS/1%, Antibiotic/Antimycotic Solution, CAPAN-1: RPMI 1640/MEM/20% FBS/1% Antibiotic/Antimycotic Solution, SW480, LoVo, HT29, NIH-3T3: DMEM/10% FBS/1% Antibiotic Antimycotic Solution) at 37° C. 5% $CO_2$ ($2.5 \times 10^6$ cells/24 hrs), separated from the culture dish using Non-enzymatic cell dissociation buffer, and then, the number ($1 \times 10^6$ cells/ml) of cells was determined with Hemocytometer.

The obtained cells were not treated with RNA aptamer, or treated with RNA aptamer (YJ-1, prepared in Example 8: 10 μg/ml) of SEQ ID NO: 13 or Mutant Aptamer (10 μg/ml, prepared in Example 8) of SEQ ID NO: 15, and introduced into a well coated with each ECM protein, and then, incubated at 37° C. 5% $CO_2$ for 30 minutes, and non-bound cells were washed with PBS containing $Ca^{2+}$ and $Mg^{2+}$ 3 times. And then, remaining cells were stained with 0.2% crystal violet (included in CytoMatrix™ (5) SCREEN KIT), and eluted by Solubilization Buffer (included in CytoMatrix™ (5) SCREEN KIT) and measured at 570 nm (microplate reader 550 Biorad).

Figure 7:
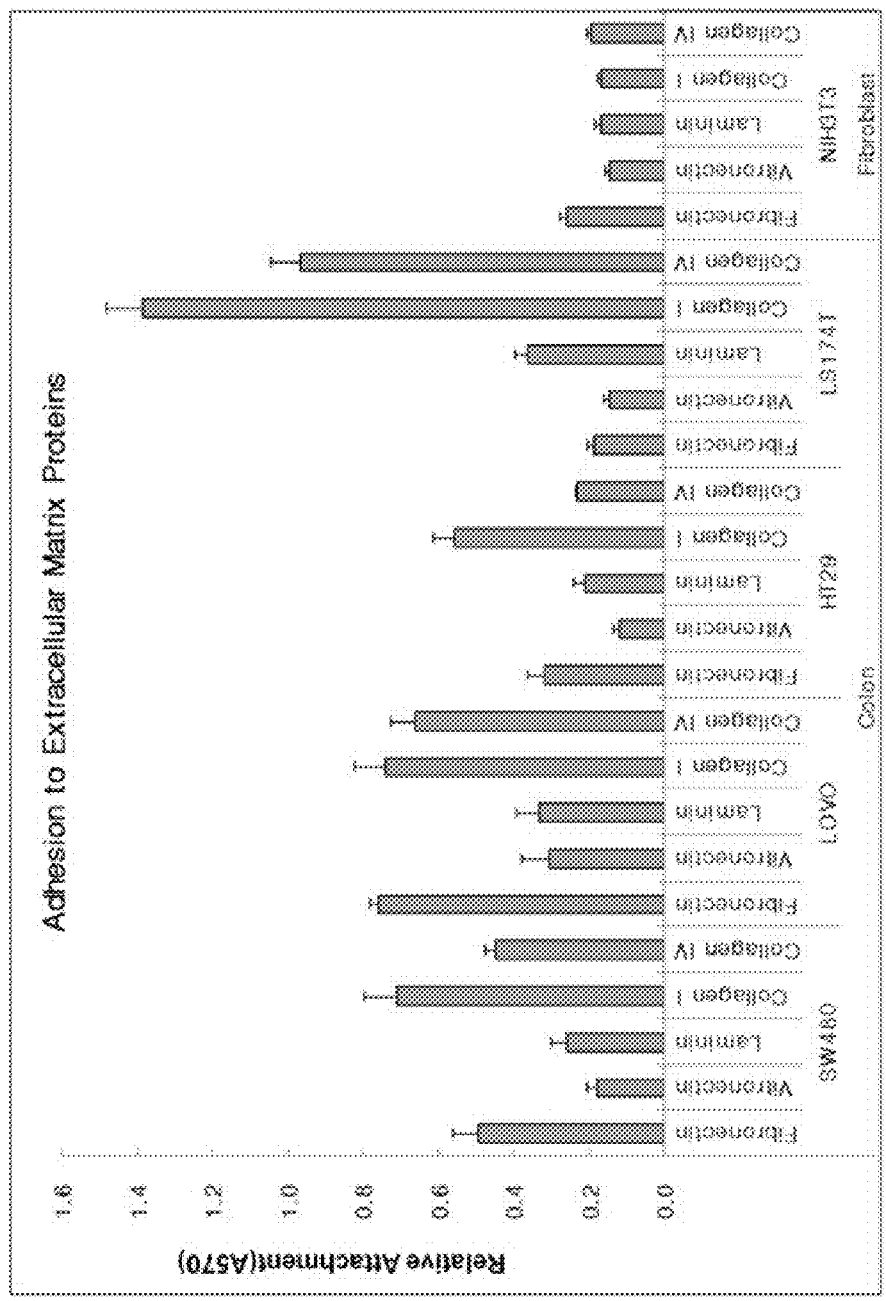
FIG. 7 is a graph showing the result of in vitro ECM adhesion assay.
Figure 8B:
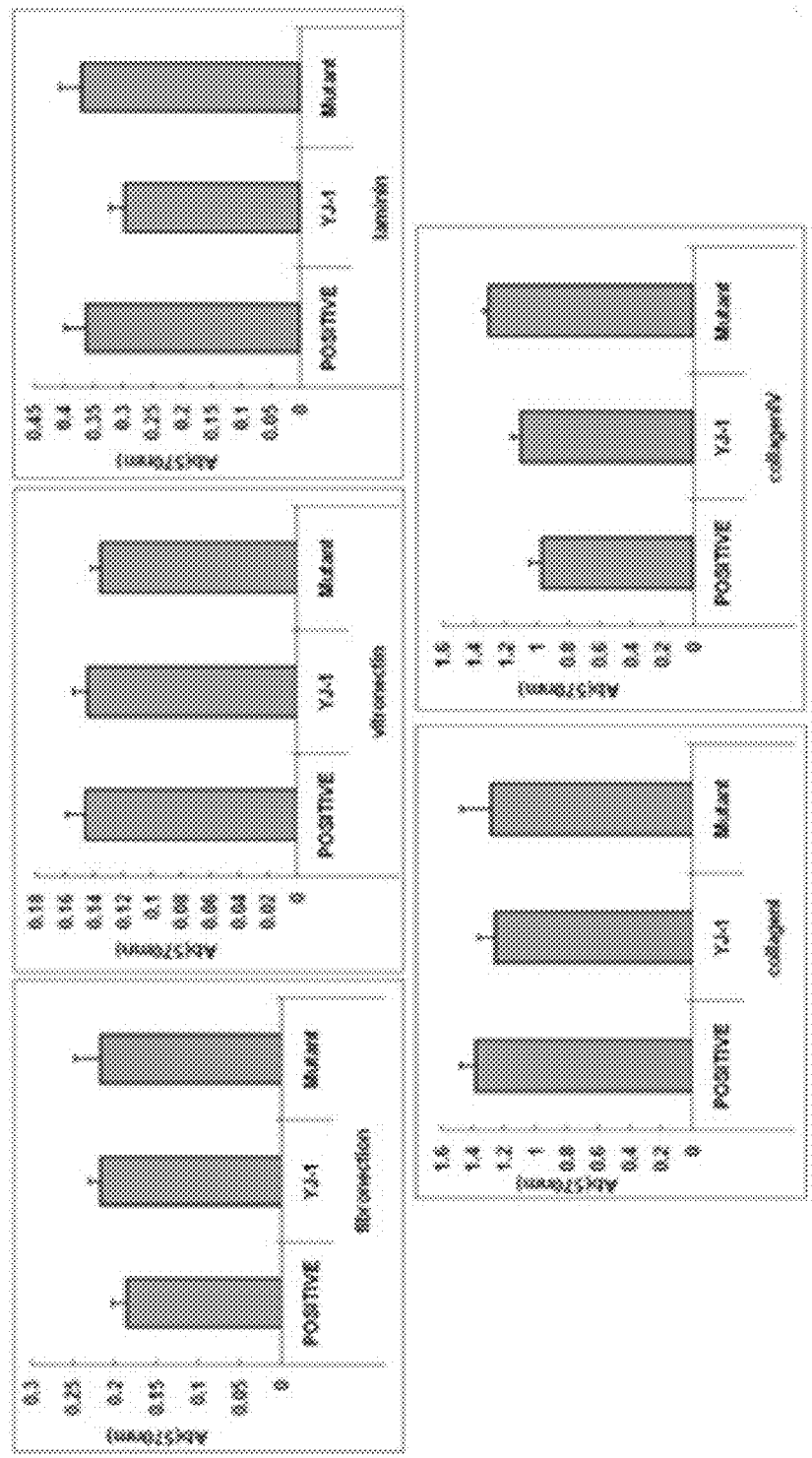
FIG. 8 is a graph showing the result of in vitro ECM adhesion inhibition assay by YJ-1 and mutant aptamer treatment.
Figure 8D:
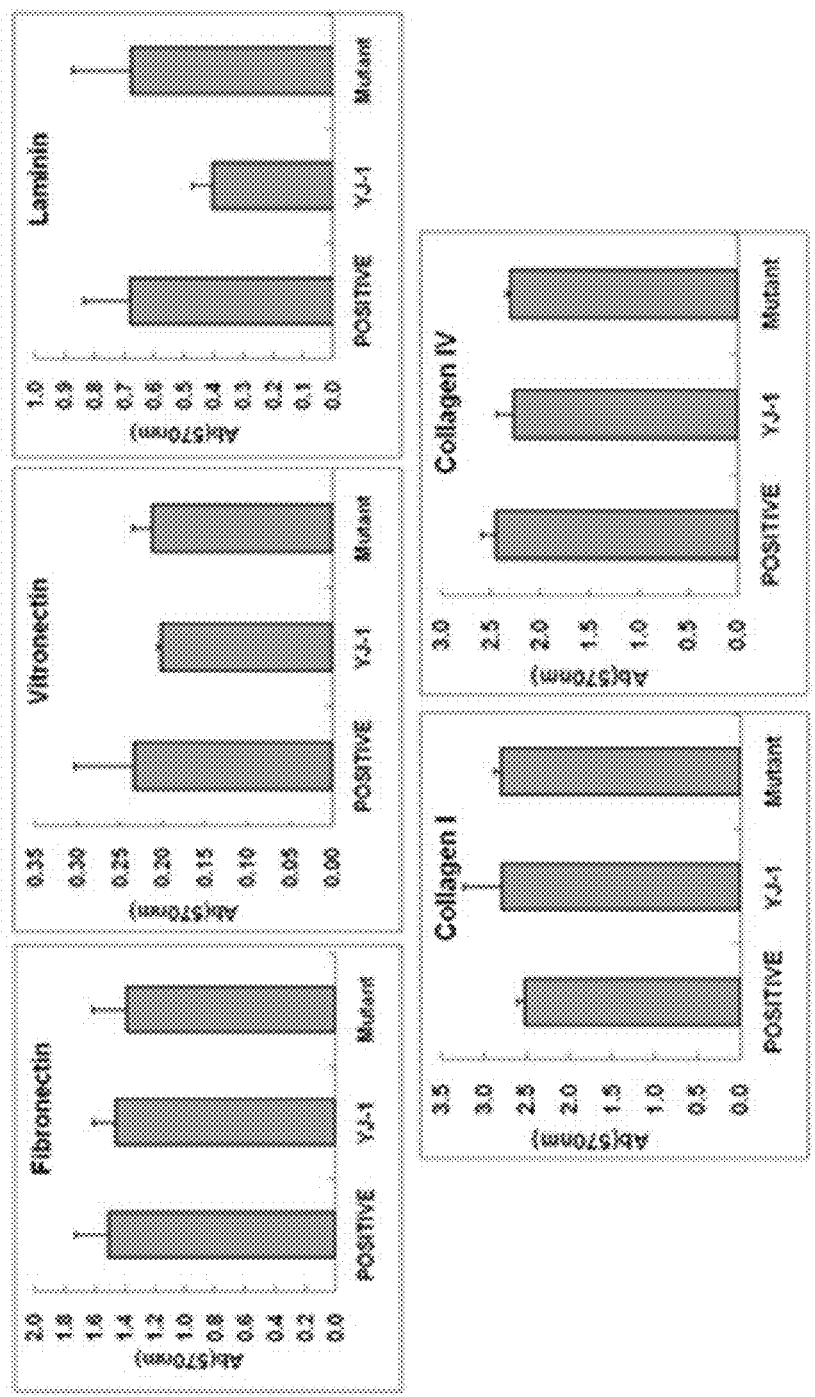
Figure 8F:
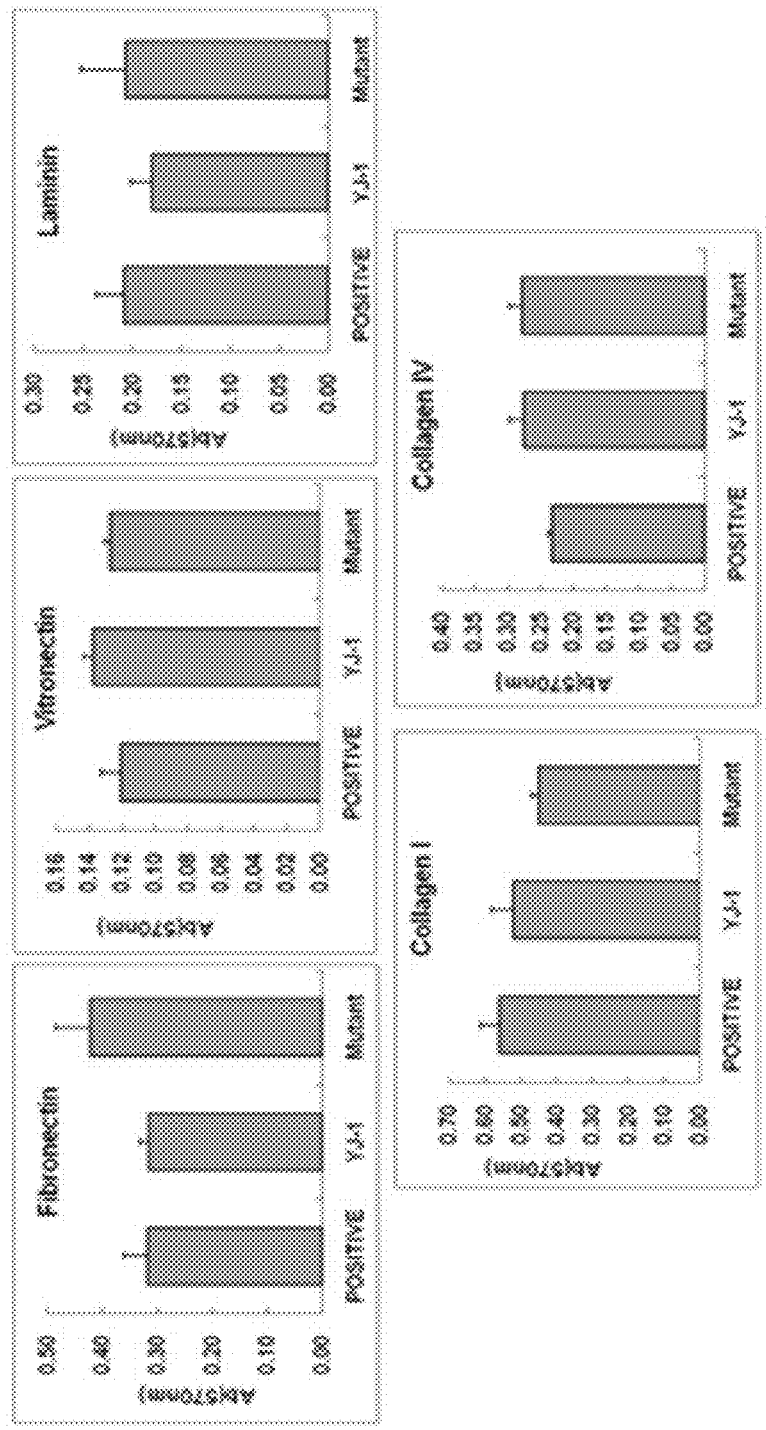
Figure 9A:
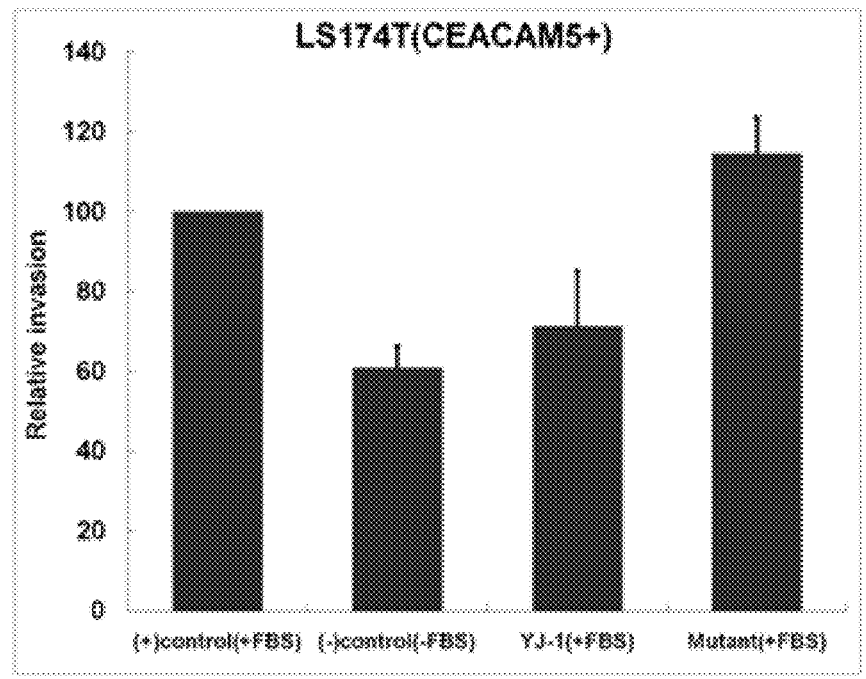
FIG. 9 is a graph showing the result of Collagen-Based cancer cell invasion inhibition Assay.
Figure 9B:
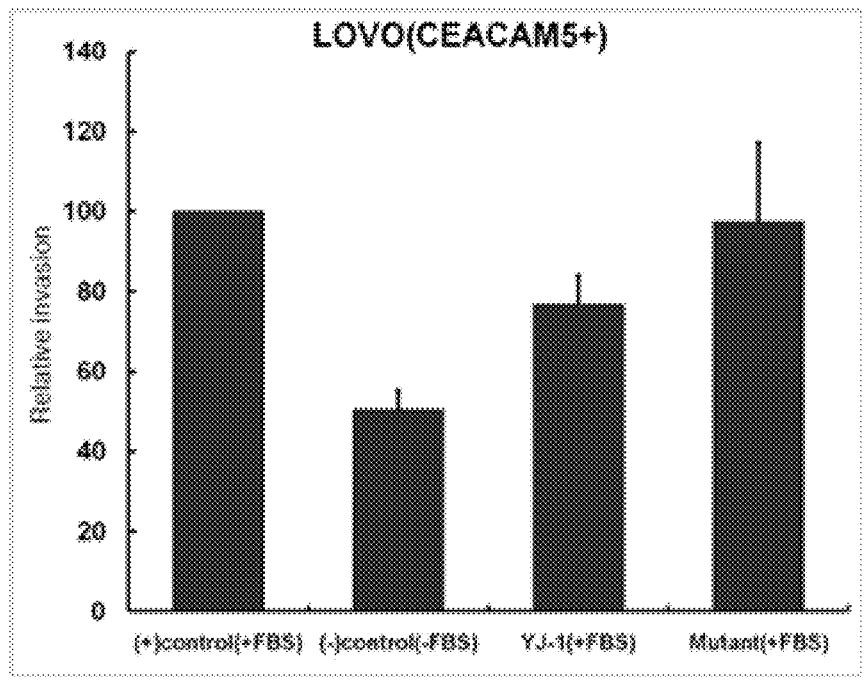
Figure 9C:
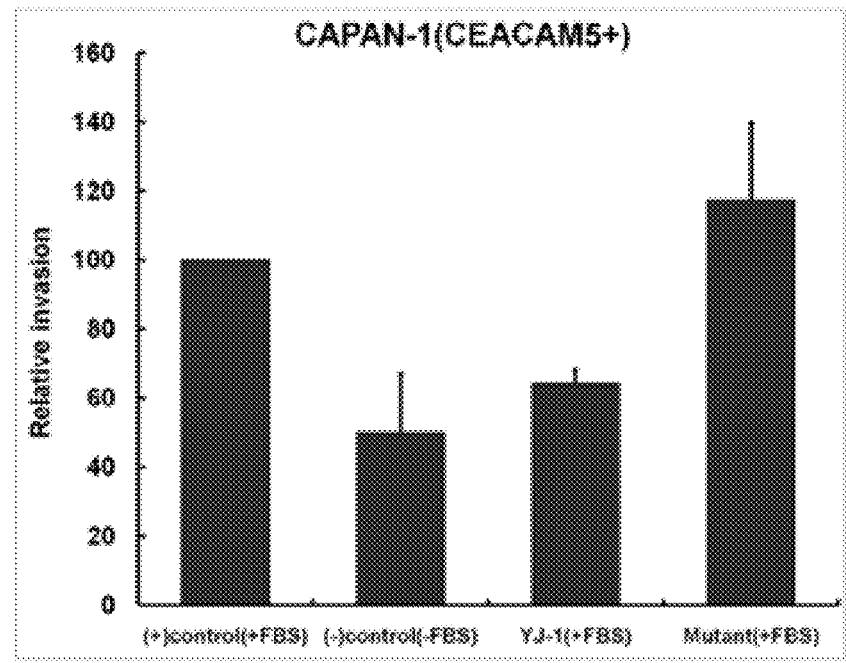
Figure 9D:
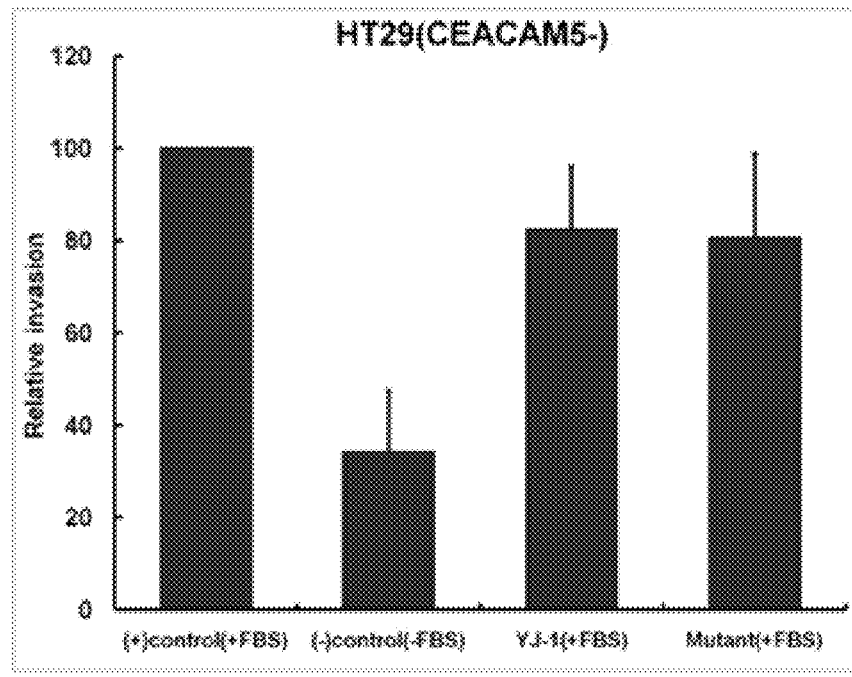
Figure 9E:
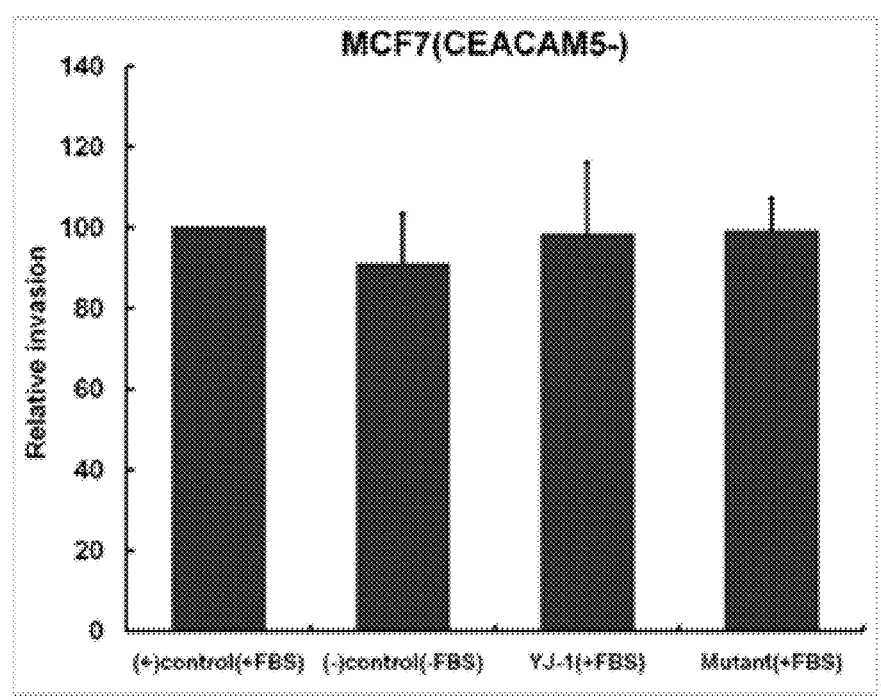

Relative adhesion degree of RNA aptamer non-treated cells is shown in FIG. 7, and the adhesion degrees of RNA aptamer treated cells are shown in FIG. 8A-8G (A-D: CEA-positive cell lines, E-G: CEA-negative cell lines). As shown in FIGS. 7 and 8, it is confirmed that the adhesion of most cancer cells to ECM proteins is not inhibited by RNA aptamer (YJ-1, SEQ ID NO: 13, prepared in Example 8), while the adhesion of some CEA-positive cancer cells, CAPAN-1 and LS174T, to one of ECM proteins, Laminin is inhibited.

Example 11

Inhibition of CEA Dependent In Vitro Invasion by RNA Aptamer

To confirm the inhibition function of RNA aptamer in the process of invasion in the steps of metastasis, Collagen-Based Cell Invasion inhibition Assay was performed (See FIG. 9).

To confirm inhibition of CEA dependent in vitro invasion by selected RNA aptamer, the cells incubated under the incubation conditions described in Example 10 were starved for 24 hours, and separated from culture dish using Non-enzymatic cell dissociation buffer, and then, washed with quenching medium (serum-free DMEM containing 5% BSA, Serum-free DMEM (HyClone), BSA (sigma)), and the number of cells was determined with Hemocytometer ($1 \times 10^6$ cells/ml).

And then, the cells were treated with RNA aptamer (SEQ ID NO: 13, prepared in Example 8; 10 μg/ml) or Mutant aptamer (SEQ ID NO: 15, prepared in Example 8; 10 μg/ml), introduced into collagen (BD biosciences) coated inserts, and incubated in a 37° C. 5% $CO_2$ incubator for 48 hours, and then, invaded cells were dyed and measured at 490 nm (microplate reader 550 Biorad).

The results are shown in FIGS. 9A-9E. As shown in FIGS. 9A-9E, it is confirmed that in CEA-positive cells, i.e., LS174T, CAPAN-1 and LoVo cells, RNA aptamer (YJ-1, SEQ ID NO: 13, prepared in Example 8) specifically inhibits invasion of cancer cell, while in CEA-negative cells, i.e., HT29 and MCF7 cells, RNA aptamer (YJ-1, SEQ ID NO: 13, prepared in Example 8) does not have influence on invasion of cancer cell.

Example 12

Figure 10A:
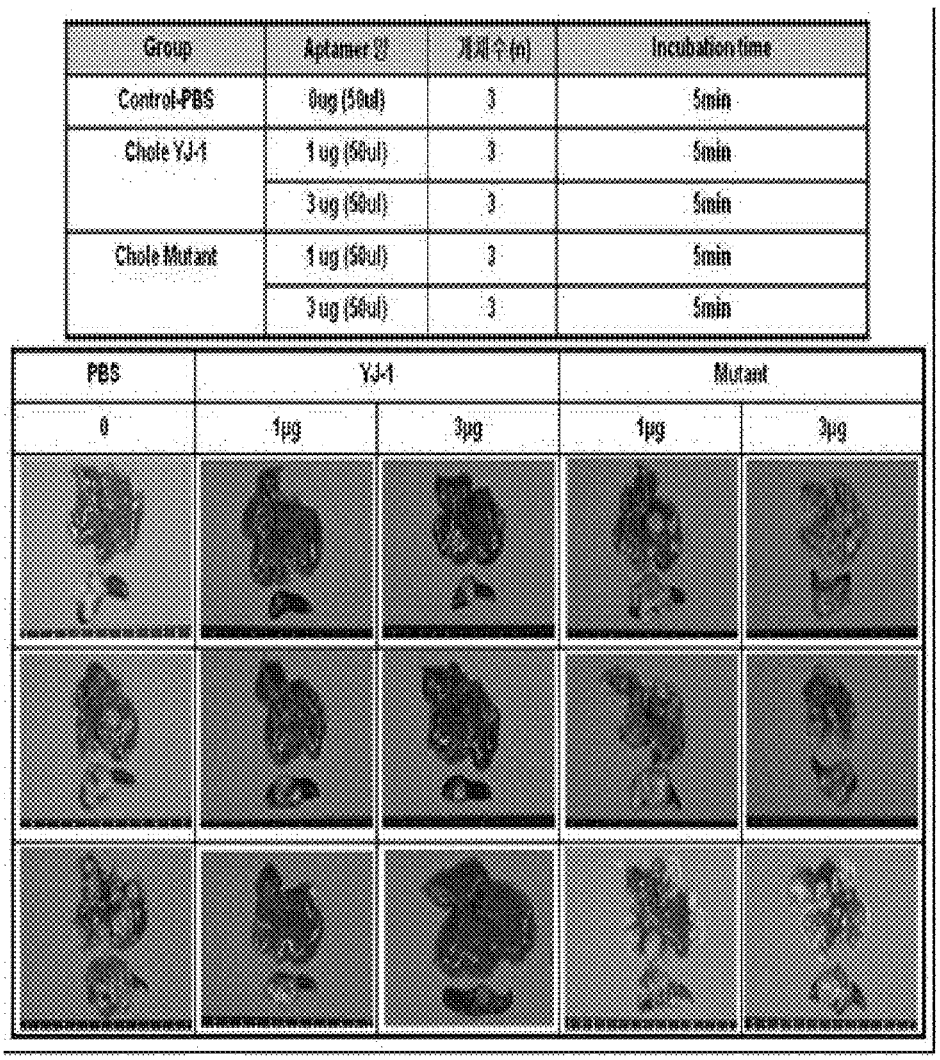
FIGS. 10A and 10B show the result of CEA-induced metastasis protection assay in animal model.
Figure 10B:
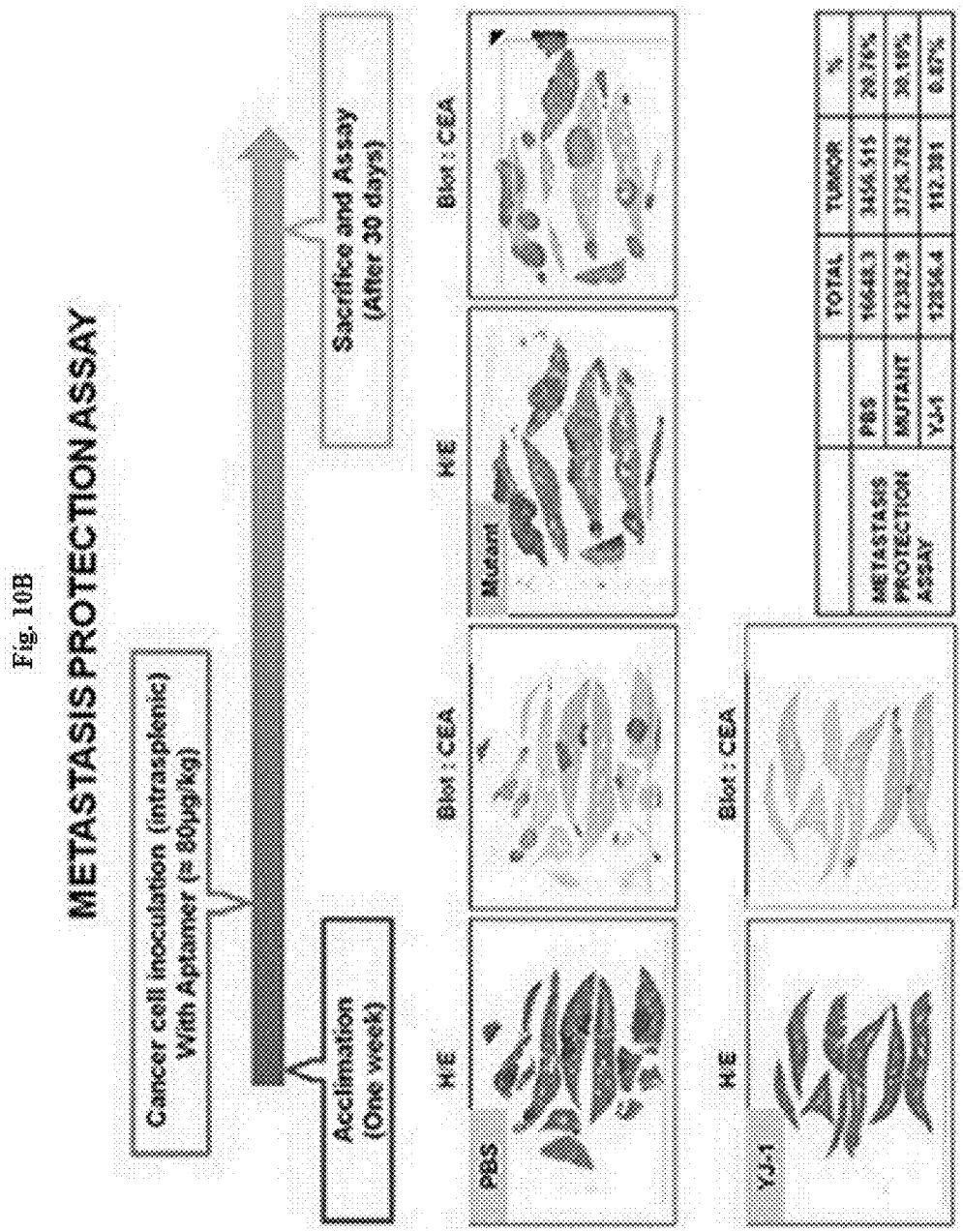

Inhibition of CEA Dependent Liver Metastasis of Colon Cancer by RNA Aptamer in Metastasis Animal Model About 6 week-old male nude mice (Balb/CAnN/CriBg-nu/nu, ORIENT.CO.LTD) received intrasplenic injection of colon cancer cell line, i.e., LS174T cells ($1 \times 10^6$), and used as an animal model of liver metastasis. CEA-positive cell, i.e., LS174T colon cancer cell (CL-188 ATCC) and cholesterol-conjugated RNA aptamer (cholesterol conjugated YJ-1, corresponding to SEQ ID NO: 13, prepared in Example 8) were incubated, and then, the reacted cells were intrasplenically injected into the mice to examine whether the formation of metastatic tumor to the liver is inhibited by RNA aptamer (cholesterol conjugated YJ-1, prepared in Example 8) in the metastasis mouse model (See FIG. 10, and FIG. 11).

For a metastasis inhibition assay, about 6 week-old male nude mouse was acclimated for 1 week, and then, CEA-positive cell, i.e., LS 174T cell line ($2 \times 10^6$ cells), and selected RNA aptamer (cholesterol-conjugated YJ-1, prepared in Example 8; ≈80 μg/kg) or its mutant aptamer (cholesterol-conjugated mutant YJ-1, prepared in Example 8; ≈80 μg/kg) were incubated at 37° C. for 5 minutes, and intrasplenically injected. After 30 days, the mouse was sacrificed, and the degree of metastasis was analyzed and shown in FIGS. 10A and 10B.

For a metastasis prevention assay, about 6 week-old male nude mouse was acclimated for 1 week, and then, CEA-positive cell, i.e., LS174T cell line ($2 \times 10^6$ cells) were intrasplenically injected, and after 10 days, selected RNA aptamer (cholesterol-conjugated YJ-1, ≈80 μg/kg) or its mutant aptamer (cholesterol-conjugated mutant YJ-1, ≈80 μg/kg) was intravenously injected through the tail vein of the mouse, and after 30 days, the mouse was sacrificed, and the degree of metastasis was analyzed by Immunohistochemistry (Ramos-Vara, J A (2005). "Technical Aspects of Immunohistochemistry". *Vet Pathol* 42 (4): 405-426) and shown in FIG. 11.

Figure 11:
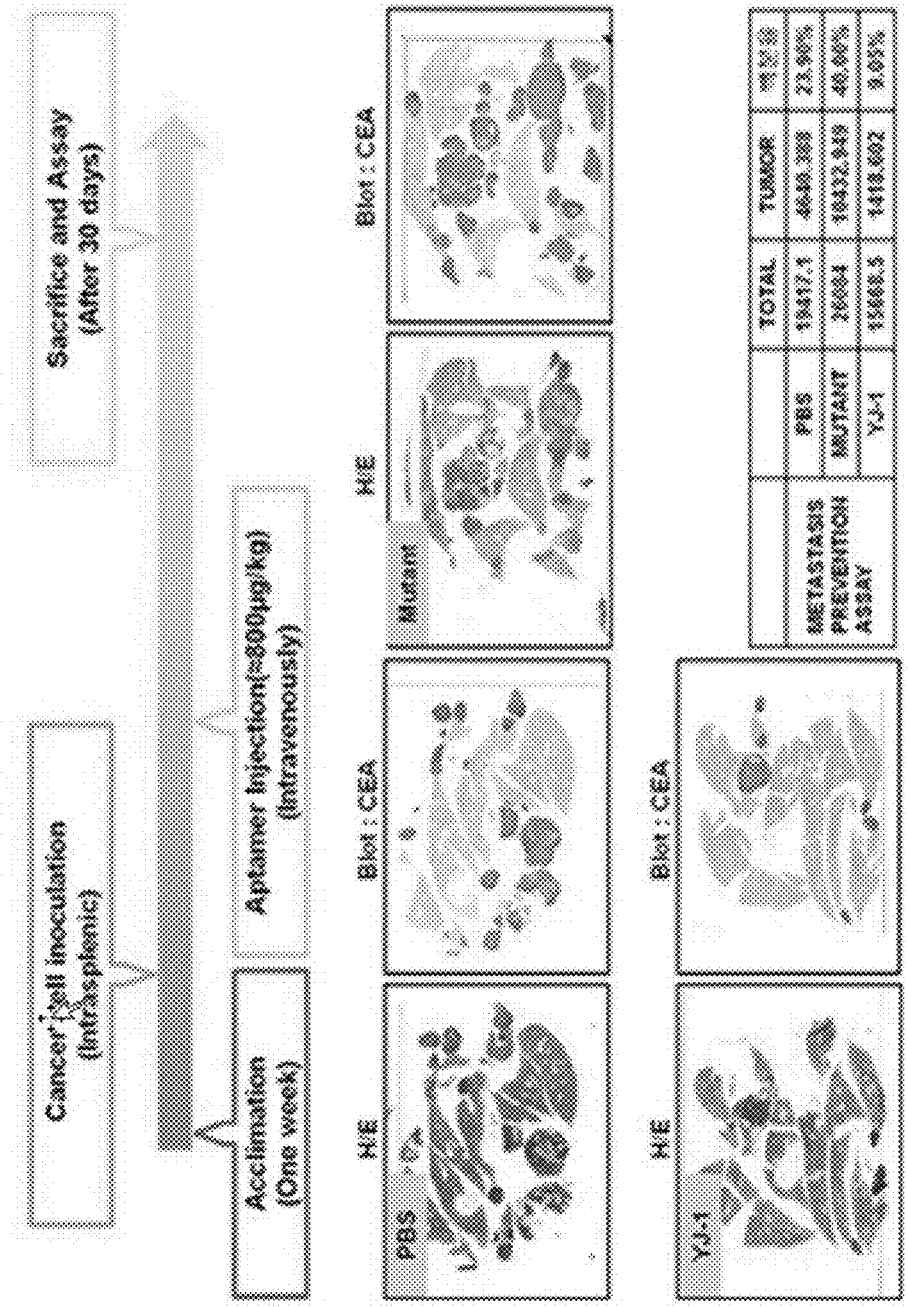
FIG. 11 shows the result of CEA-induced metastasis prevention assay in animal model.

As shown in FIG. 10, it is confirmed that when the CEA aptamer (cholesterol-conjugated YJ-1, corresponding to SEQ ID NO: 13) is incubated, liver metastasis remarkably decreases compared to the mutant aptamer (cholesterol-conjugated YJ-1 mutant, corresponding to SEQ ID NO: 15). And as shown in FIG. 11, it is confirmed by Immunohistochemistry that in a metastasis prevention assay wherein CEA-positive cell, i.e., LS174T colon cancer cells are intravenously injected first, and, after 10 days, the RNA aptamer (cholesterol-conjugated YJ-1) or the mutant (cholesterol-conjugated mutant YJ-1) is intravenously injected, the RNA aptamer (cholesterol-conjugated YJ-1) also specifically inhibits liver metastasis of colon cancer cell, compared to Mutant (cholesterol-conjugated mutant YJ-1).

Figure 12:
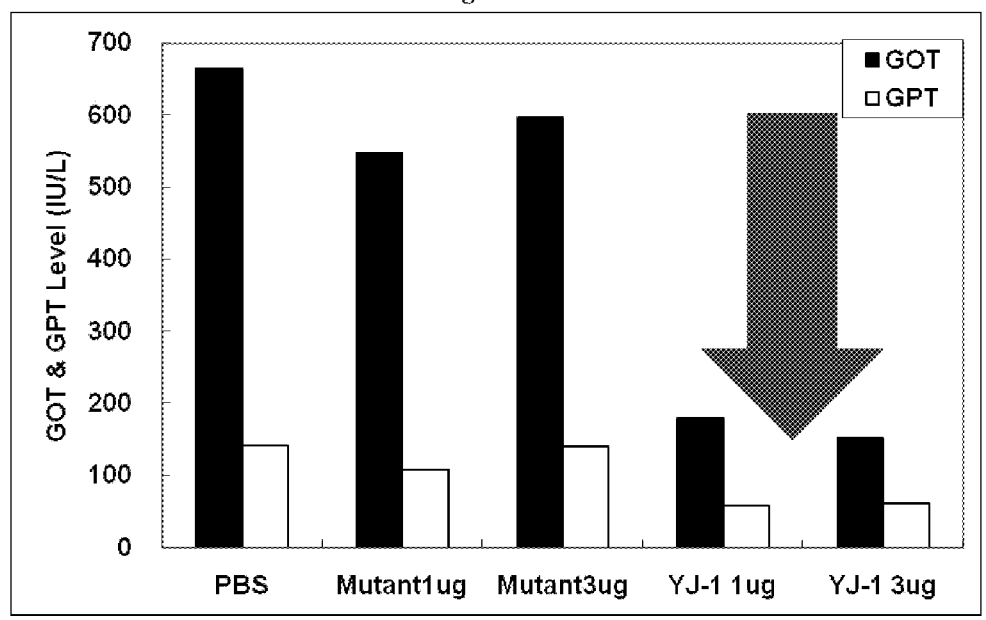
FIG. 12 is a graph showing the result of liver toxicity test.

It is also confirmed with an automation device, Toshiba TBA-200FR, that in vivo the RNA aptamer (cholesterol-conjugated YJ-1) treatment does not cause toxicity in liver tissue of mice (FIG. 12).

Example 13

Inhibition of CEA Dependent In Vitro Migration by RNA Aptamer

To confirm the inhibition function of RNA aptamer (YJ-1, prepared in Example 8) in the process of migration in the steps of metastasis, Cancer cell migration inhibition Assay was performed. Migration assay kit (Oris™ Cell Migration Assay kit, Platypus Technologies) was used, and the method was as follows. After determining the number of incubated cells with Hemocytometer ($5 \times 10^4$ cells/ml), they were seeded into a well. After incubating confluently, the cells were starved for 16 hours, and the kit insert was removed, and then, the cells were treated with selected RNA aptamer (for example, YJ-1 aptamer: 10 μg/ml) or its Mutant aptamer (for example, Mutant YJ-1 aptamer, prepared in Example 8: 10 μg/ml) and incubated in a 37° C. 5% CO2 incubator for 24 hours, and then, cells which moved to the center were dyed with Calcein AM Fluorescent Dye (4 ug/ml, BD Biosciences) and measured at 490 nm (microplate reader 550, Biorad).

The result is shown in FIG. 13. As shown in FIG. 13, it is confirmed that in CEA-positive cells, i.e., LS174T and LoVo cells, CEA aptamer (YJ-1, prepared in Example 8) specifically inhibits migration of cancer cells, while in CEA-negative cell, i.e., HT29 cell (ATCC, Manassas, Va.), CEA aptamer (YJ-1, prepared in Example 8) does not have influence on the migration of cancer cell.

Example 14

Inhibition of CEA Dependent Anoikis Resistancy by RNA Aptamer

To confirm whether RNA aptamer (YJ-1, prepared in Example 8) inhibits the function of CEA for inhibiting Anoikis in the steps of metastasis, Anoikis inducing Assay was performed. Caspase 8 Colorimetric Assay Kit (Millipore) was used. One day before, a polyHEMA coated plate was manufactured (polyHEMA was loaded on a plate at a concentration of 3 mg/cm$^2$, and O/N incubated in a clean bench). And, selected RNA aptamer (for example, YJ-1 aptamer prepared in Example 8) or its mutant aptamer (for example, Mutant YJ-1 aptamer prepared in Example 8) was transfected into LoVo cell twice (TransIT-TKO® (Mirus Bio LLC); 50 nM aptamer 16 hrs), and then, the transfected $2 \times 10^6$ cells were loaded on the previously manufactured polyHEMA coated plate, and treated with selected RNA aptamer (for example, YJ-1 aptamer prepared in Example 8: 40 μg/ml) or its mutant aptamer (for example, Mutant YJ-1 aptamer prepared in Example 8: 40 μg/ml) in a 37° C. CO2 incubator and suspension incubated for 24 hours. And then, the cells were treated with 100 μL of 1× Cell Lysis Buffer to obtain total protein, which were then treated with Caspase 8 substrate and reacted for 1-2 hours, and measured at 410 nm (microplate reader 550, Biorad).

Figure 14:
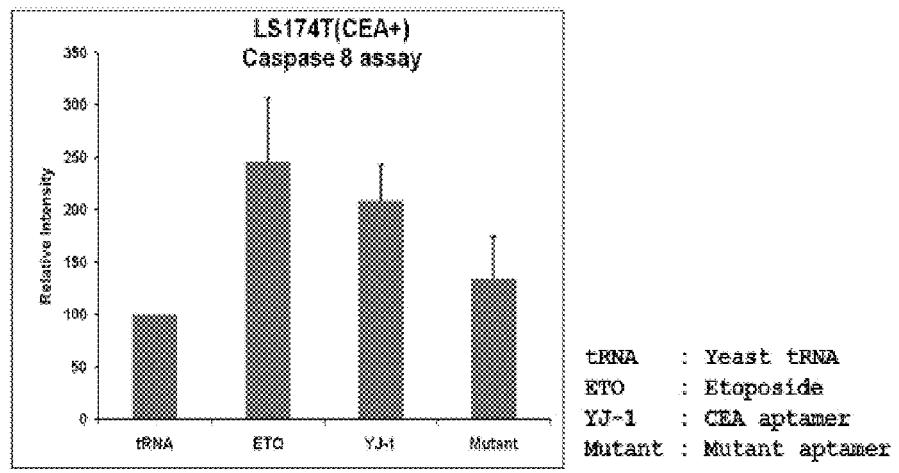
FIG. 14 is a graph showing the result of Anoikis inducing Assay.

The result is shown in FIG. 14. As shown in FIG. 14, it is confirmed that in CEA-positive cell, i.e., LoVo cell, CEA aptamer (YJ-1, prepared in Example 8) specifically induces Anoikis of cancer cell similarly to positive control Etoposide (sigma) treatment, while mutant aptamer does not have influence on inducing of cancer cell Anoikis Example 15

Fluorescence Staining of CEA Positive Cell by RNA Aptamer

To confirm specific binding to CEA-positive cell using selected RNA aptamer, Fluorescence aptamer cell staining assay was performed. One day before, a cover slip was fixed to a 100 mm dish using 0.1% Gelatin. Next day, the number of incubated cells were determined with Hemocytometer ($1 \times 10^6$ cells/10 ml), and then, they were seeded into the cover slip-fixed 100 mm dish. After incubating in a 37° C. 5% CO2 incubator for 24 hours, the cover slip was moved to a 12 well plate and fixed with 4% paraform aldehyde solution (sigma). And then, the cells were treated with primary Blocking buffer (TNB buffer) at room temperature for 1 hour, and then treated with secondary Blocking buffer (PBS-MgCl2 with tRNA (10 ug/ul), poly IC (1 ug/ul)) for 40 minutes. After washing with PBS Mg buffer (PBS with 1.5 mM MgCl2) once, they were treated with selected Biotin-tagged RNA aptamer (for example, YJ-1 aptamer 500 nM) or its mutant aptamer (for example, Mutant YJ-1 aptamer 500 nM) at room temperature for 30 minutes. After washing with PBS Mg buffer 3 times, they were treated with fluorescence-tagged Streptavidin (BD bioscience.) at a concentration of 1:100 at room temperature for 1 hour. After washing with PBS-T Mg buffer (PBS with 1.5 mM MgCl2, 0.05% tween20) 3 times, they were mounted with a mounting solution (Slowfade Gold antifade reagent with DAPI, invitrogen), and observed by fluorescent microscope (Carl Zeiss, Inc.).

Figure 15:
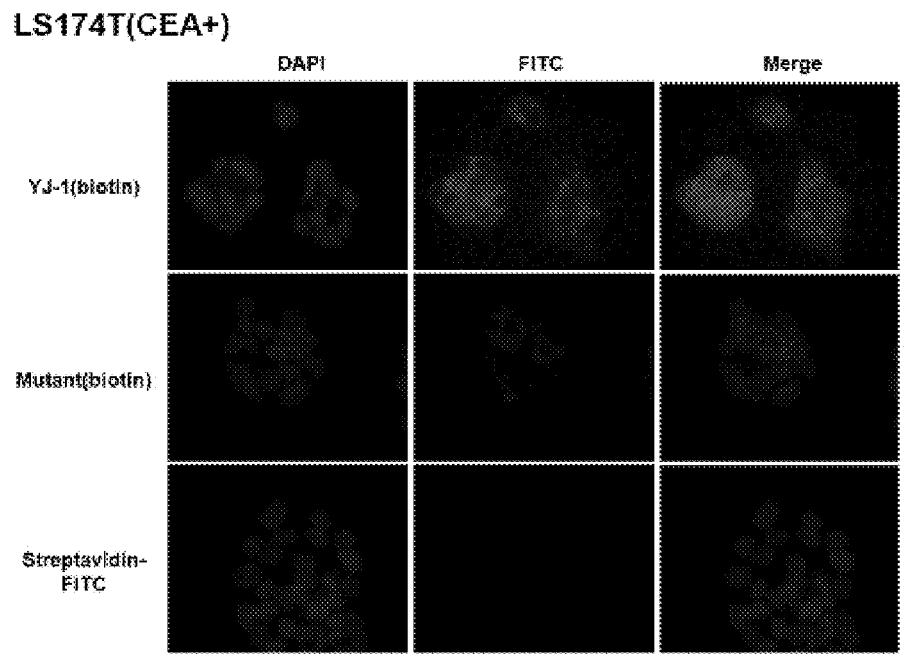
FIGS. 15 to 17 show staining images of CEA-positive (CEA-expressing) cancer cell when being treated with CEA Aptamer.
Figure 16:
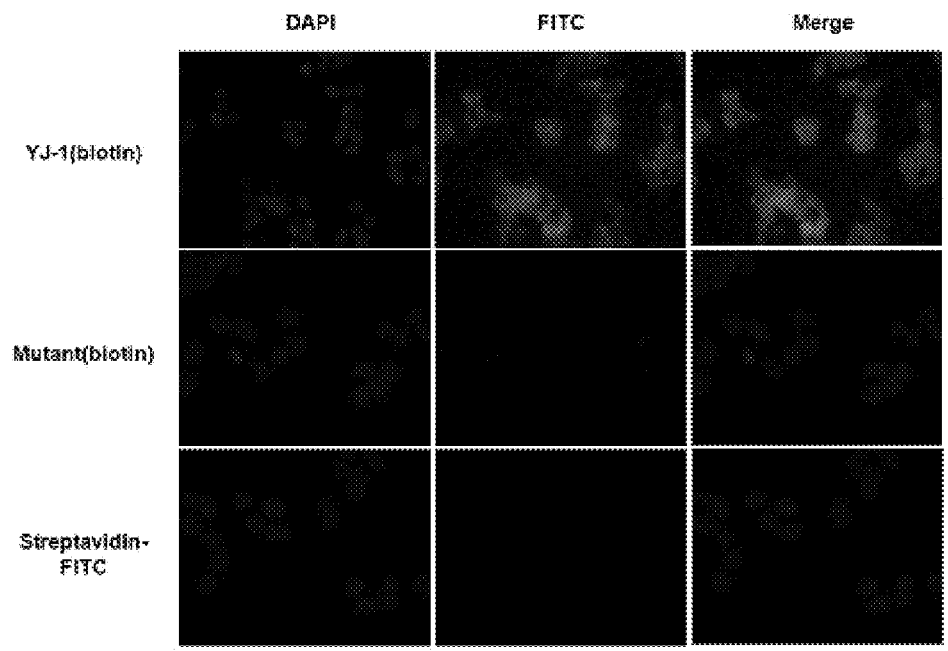
Figure 17:
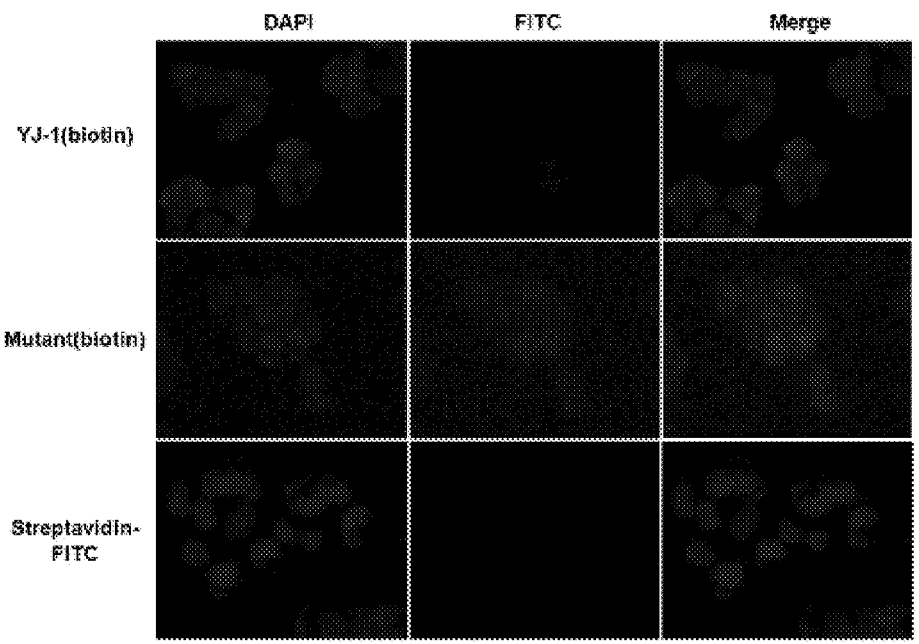

The results are shown in FIG. 15, FIG. 16, and FIG. 17, respectively. It is confirmed through flurescence staining that CEA aptamer (YJ-1) specifically binds to CEA-positive cancer cells, i.e., LS174T and LoVo cells (FIG. 15, FIG. 16). And, it is confirmed that CEA aptamer (YJ-1) does not bind to CEA-negative cell, i.e., HT29 cell (FIG. 17). It is also confirmed that control mutant aptamer fails to bind to the surface of cancer cell irrespectively of CEA expression (FIG. 15, FIG. 16, FIG. 17).

In conclusion, RNA aptamers of SEQ ID NO: 1 to SEQ ID NO: 14 including optimized YJ-1 RNA aptamer specifically bind to N domain of CEA, and thus, inhibits aggregation of CEA-positive cancer cells, inhibits ECM adhesion of some CEA-positive cancer cells, and inhibits specifically to CEA-positive cells in vitro invasion or in vitro migration, which is an important process of metastasis. And, it is confirmed that Anoikis resistance induced by CEA that is characteristic of metastatic cancer cell is aptamer specifically inhibited, and the RNA aptamer effectively inhibits liver metastasis in an animal model of liver metastasis of colon cancer, indicating that it may be useful for inhibiting liver metastasis induced by CEA. Finally, it is confirmed by flurosecence staining of CEA-positive cells using RNA aptamer that CEA aptamer (YJ-1) specifically binds to CEA-positive cancer cell, indicating that it may be useful for specific diagnosis of CEA-overexpressing cancer cell.

Example 16

Measurement of Inhibition of CEA Dependent Anoikis Resistancy by RNA Aptamer

CEA-dependent anoikis resistancy was analyzed by caspase 8. Caspase 8 activity was assessed with Caspase 8 Colorimetric Assay Kit (Millipore). Briefly, one day before the assay, a Poly(2-hydroxyethyl methacrylate) (polyHEMA, Sigma, St. Louis, Mo.) coated plate was manufactured at a concentration of 3 mg/cm$^2$. LS174T cells (CL-188 ATCC) were cultured at 40-50% confluence for 24 h at 37° C., and treated with YJ-1 aptamer prepared in Example 8 (50 nM) or mutant aptamer (mutant YJ-1) prepared in Example 8 (50 nM) twice. The treated cells ($2\times10^6$) were then cultured on the previously prepared polyHEMA coated plate with suspension condition for 24 h, and lysed. Same amount of total protein samples, wherein each sample was obtained from the YJ-1 aptamer treated cells, mutant aptamer treated cells, or control cells, were treated with caspase 8 substrate contained in the Caspase 8 Colorimetric Assay Kit, reacted for 1-2 h, and measured at 410 nm (microplate reader 550, Bio-Rad). Etoposide (10 µg/ml)-treated sample was used as a positive control.

Figure 18A:
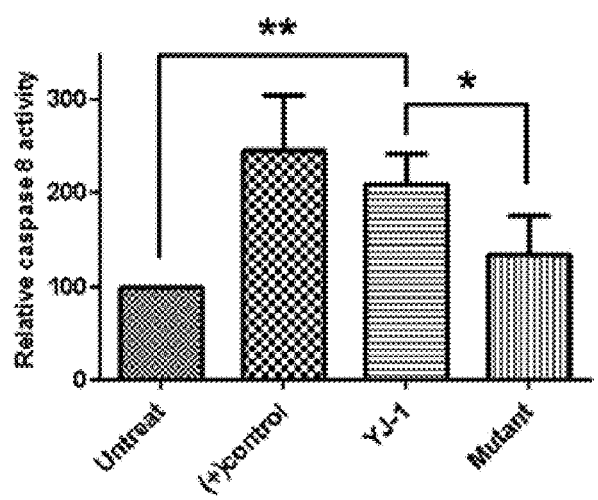
FIG. 18A shows results of Caspase 8 activity assay, 18B shows results of SEAP activity measured in mammalian two-hybrid system, and 18C shows the expression level of YJ-1 aptamer and mutant aptamer.

The obtained results are shown in FIG. 18A. FIG. 18A shows relative caspase 8 activity depending on the treatment of aptamer, wherein in suspension culture, LS174T cell line was treated with YJ-1 or mutant aptamer, or etopo side (positive control). Caspase activity in each treated cell was represented as a percentage of untreated cells. As shown in FIG. 18A, in suspension culture condition of LS174T cells, treatment of YJ-1 aptamer specifically induced caspase 8 activity that is a main mediator of anoikis in colon cancers, up to similar level to positive control (Etoposide).

To observe whether the induction of caspase 8 activity by YJ-1 aptamer was due to directly blocking CEA and DR5 interaction, a mammalian two-hybrid system was performed.

For mammalian two-hybrid system, Matchmaker™ Mammalian Two-Hybrid Assay Kits (Clontech, Mountain View, Calif.) was used. NCEA or ACEA and DR5 were cloned in the pM and pVP16 vectors, respectively. The pM vector contains the GAL4 DNA-BD, and pVP16 vector contains the GAL4 AD, wherein the vectors are included in the Matchmaker™ Mammalian Two-Hybrid Assay Kits. The secreted human alkaline phosphatase (SEAP) vector contains GAL4 binding sites upstream of the SEAP gene (reporter), wherein the vector is also included in the Matchmaker™ Mammalian Two-Hybrid Assay Kits. Here, 293T cell lines which stably express YJ-1 or mutant aptamers using zeocin (600 µg/ml, Invitrogen, Carlsbad, Calif.) were established as follows. 293T cells (ATCC, Manassas, Va.) were transfected with 1 g of 7SL promoter-based vector encoding the YJ-1 aptamer YJ-1 or mutant aptamer, wherein the original vector was donated from Dr. David R. Engelke from U. Michigan. The cells which harbor the expression vector and stably express the aptamer were then selected using zeocin.

Expression levels of YJ-1 or mutant aptamer were measured by quantitative RT-PCR assay in each stable cell line (RT with reverse primer (5'-ACGAAAGTACTGGTTTT-3'; SEQ ID NO: 30) then quantitative PCR by real-time PCR with forward primer (5'-GCGGAAGCGTGCTGG-3'; SEQ ID NO: 31) and above reverse primer (SEQ ID NO: 30)). The 293T cells stably expressing aptamers were transfected with the indicated three vectors for 48 h using TransIT-1® (Minis Bio LLC, Madison, Wis.). Protein-protein interactions were then assessed by measuring SEAP activity in the medium of transfected cells and represented as relative a control co-transfected with basal vectors and reporter construct (Basal). Values represent averages of three independent experiments.

Figure 18B:
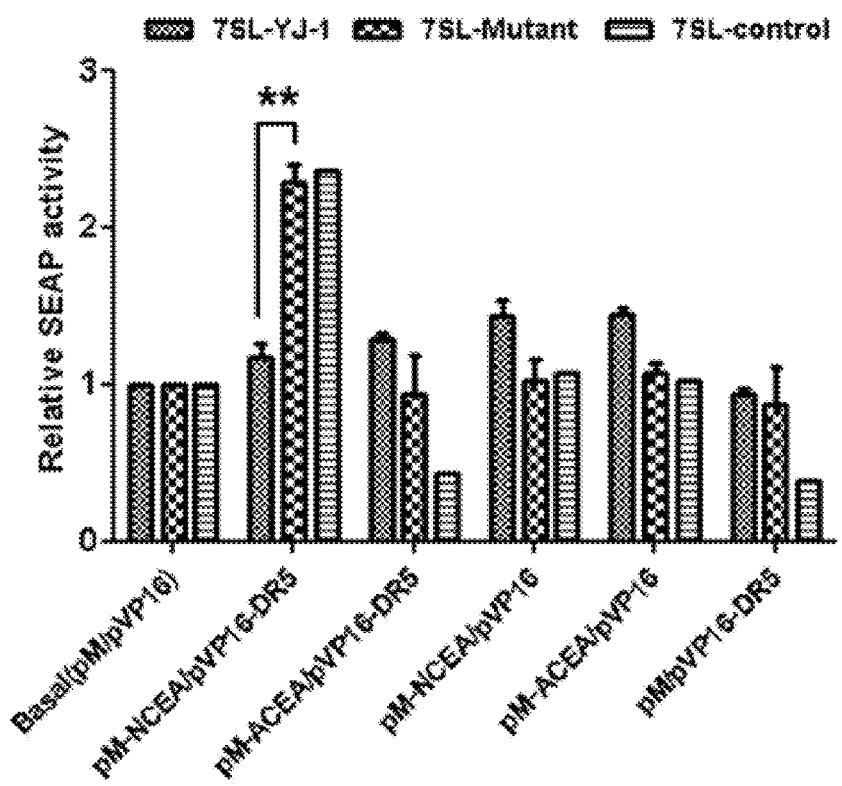

The obtained results are shown in FIG. 18B, showing that CEA and DR5 interaction was directly inhibited by YJ-1 aptamer. As shown in FIG. 18B, when the YJ-1 expressing cells were co-transfected with the pM/NCEA, pVP16/DR5, and SEAP vectors, the level of SEAP was not increased. On the other hand, in mutant aptamer expressing cells and control stable cell lines, the level of SEAP was increased 2.5-fold ($P<0.005$) compared with all negative controls.

Figure 18C:
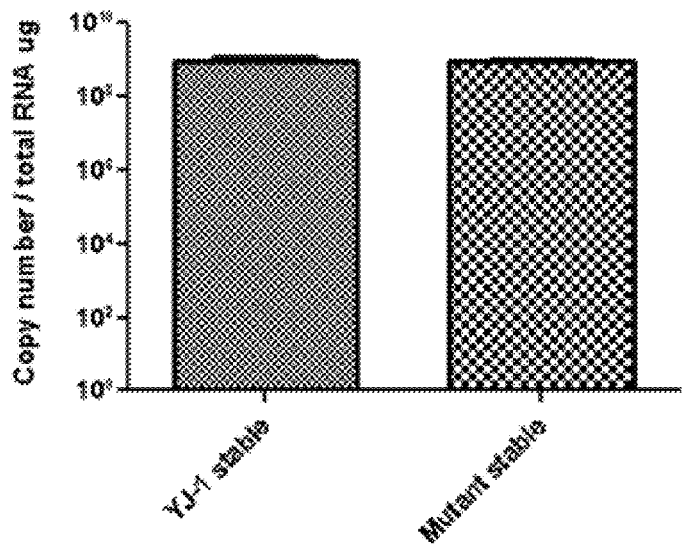

The expression levels of YJ-1 aptamer and mutant aptamer in the 293T cells, which were measured by the quantitative RT-PCR assay as above, were shown in FIG. 18C. Aptamer copy number is inferred from the standard curve. Values represent five independently prepared total RNA samples. **=$p<0.005$, *=$p<0.05$. Error bars, ±SD. As shown in FIG. 18C, no significant difference in the expression level of YJ-1 and mutant aptamer was observed in each stable cell line. Thus, YJ-1 aptamer specifically inhibited the interaction of NCEA and DR5 in cells.

In conclusion, 18A-18C shows that CEA-related anoikis resistancy is decreased by the RNA aptamer through direct blocking of CEA and DR5 interaction.

Example 17

Figure 19:
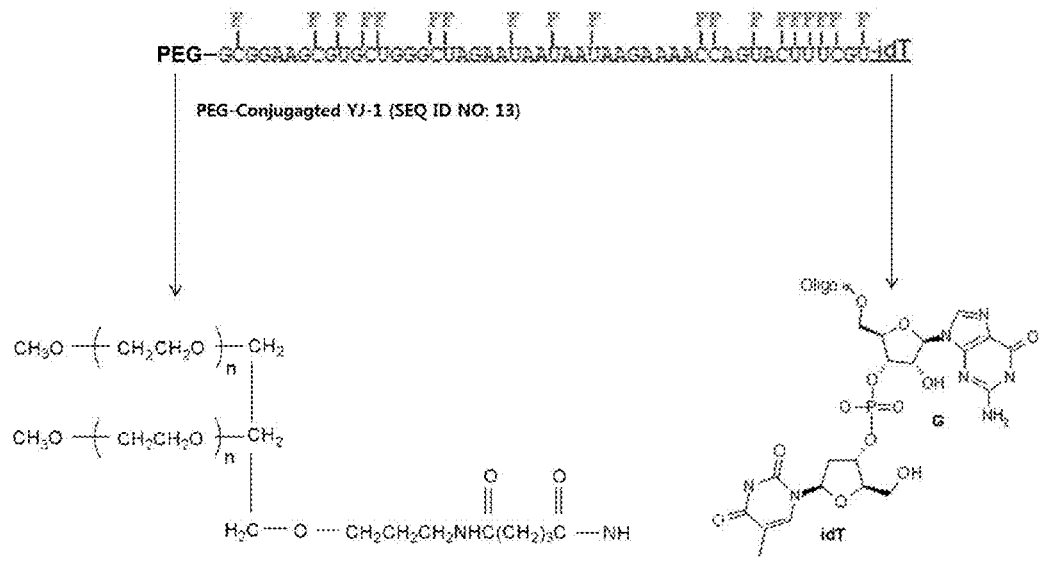
FIG. 19 shows the structure of PEG conjugated aptamer.

Inhibition of CEA Dependent Liver Metastasis of Colon Cancer by RNA Aptamer In Vivo <17-1> Preparation of PEG Conjugated Aptamer To increase in vivo aptamer availability and to prevent RNase attack, 40 kDa polyethyleneglycol (PEG) was attached to 5' end of the YJ-1 aptamer and inverted dT was added to 3' end, to generate PEG conjugated YJ-1 aptamer (PEG-YJ-1 aptamer). The preparation of the PEG-YJ-1 aptamer was performed as follows. Chemically synthesized YJ-1 or mutant aptamer described in Example 8 was dissolved in 50 mM sodium borate (pH9.0) in a concentration of 10 mg/ml. Ten fold more amount of 40 kDa polyethyleneglycol (mPEG40K-NHS, NOF, Japan) was then added to the solution and incubated for 1 h at 20° C. The PEG-conjugated aptamer was purified using Q-sepharose column with 0-500 mM NaCl gradient equilibrated in 10 mM Sodium Phophate (pH7.0). Purified PEG-conjugated aptamer was concentrated and desalted using VIVASPIN (Satorius, MWCO 10K, Cat# VS2001), and finally dissolved in water. The structure of the obtained PEG conjugated YJ-1 aptamer was shown in FIG. 19.

<17-2> Pharmacokinetics Measurements

BALB/C mice (BALB/cAnNCrI, NARA Bio, Seoul, Korea, 6 week-old male nude mice average 20 gram; n=5 per each treatment group) were injected IV with various concentration of YJ-1 aptamer tagged with a 40 kDa PEG (PEG-YJ-1 aptamer; 1 mg/kg, 10 mg/kg, 100 mg/kg) prepared in Example <17-1> or unmodified YJ-1 aptamer (10 mg/kg) prepared in Example 8. The mice were injected also IP with YJ-1 aptamer modified with a 40 kDa PEG (PEG-YJ-1 aptamer; 10 mg/kg).

Approximately 100 μl of blood volume was collected from each mouse in EDTA coated tube at 15 min, 30 min, 1 h, 2 h, 4 h, 8 h, 12 h, or 24 h after injection with the aptamer. Plasma was separated from collected blood serum and diluted with desterilizd water (1/15; v/v). Diluted plasma was reverse-transcribed with AMV reverse transcriptase (Finnzymes, Vantaa, Finland) using reverse primer (5'-ACGAAAG-TACTGGTTTTCT-3'; SEQ ID NO: 32). The aptamer concentrations in blood samples were then analyzed with quantitative PCR analysis by real-time PCR using Rotor-Gene (Corbett, Valencia, Calif.) and SYBR Green PCR Core Reagents (PE Biosystems, Carlsbad, Calif.) with forward primer (5'-GCGGAAGCGTGCTGG-3'; SEQ ID NO: 31) and above reverse primer (SEQ ID NO: 32).

Figure 20A:
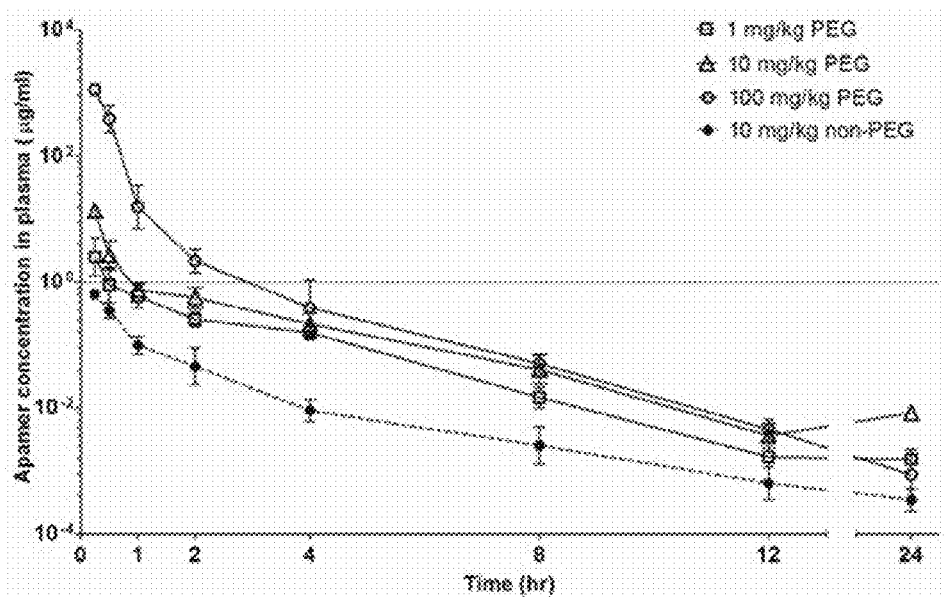
FIGS. 20A to 20C show time courses of plasma aptamer concentrations in normal mice.
Figure 20B:
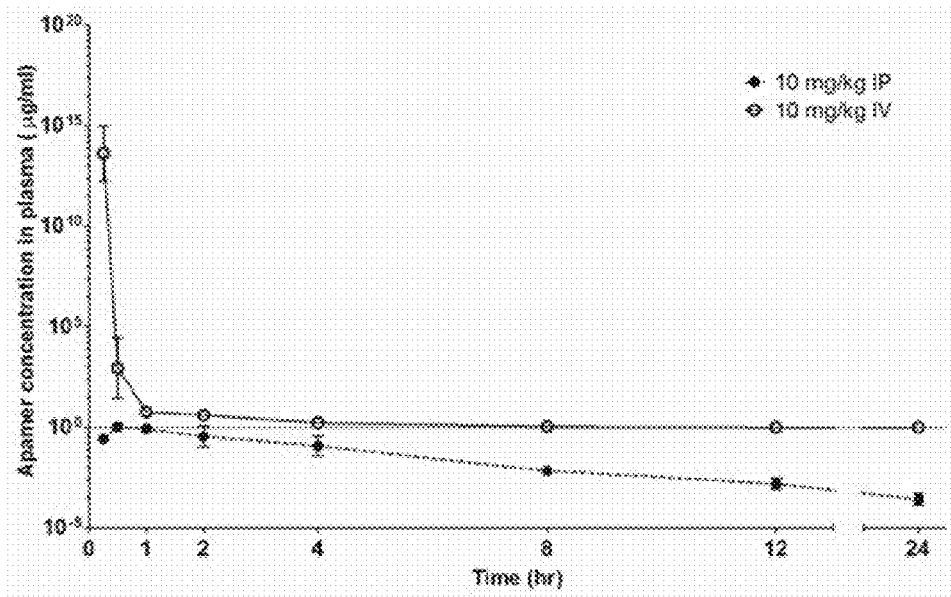
Figure 20C:
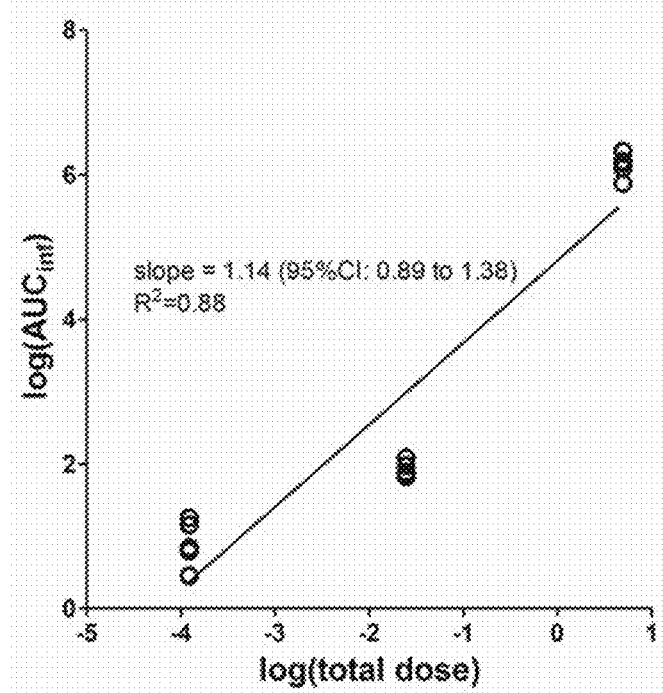

The obtained results are shown in FIG. 20A-20C and Table 1.

FIG. 20A shows the plasma aptamer concentrations with intravenous (IV) administration of PEG-YJ-1 aptamer at the dose of 1 mg/kg, 10 mg/kg, and 100 mg/k and YJ-1 aptamer (non-PEG) at the dose of 10 mg/kg. Data are presented as mean±SD (n=5 for each administrations).

FIG. 20B shows the plasma aptamer concentrations with intravenous (IV) administration and intraperitoneal (IP) administration of PEG-YJ-1 aptamer at the dose of 10 mg/kg. Data are presented as mean±SD (n=5 for each administrations)

FIG. 20C shows the relation between area under the curve from administration to infinity (AUCinf; (mg·mL/hr) and the total dose (milligrams) of PEG aptamer after log transformation. The 95% CIs of the slopes contained 1, which suggests dose proportionality. CI=confidence interval.

Table 1 shows non-compartmental pharmacokinetic parameters of PEG and non-PEG aptamer following IV or IP administration in mouse:

Data are expressed as mean±SD (n=5 for each administrations).

$\lambda_z$, terminal elimination rate constant; $t_{max}$, time at maximal concentration; Cmax, maximal concentration; $AUC_{last}$, area under the curve from administration to the last measured concentration; $AUC_{inf}$, area under the curve from administration to infinity; $AUC_{\%Extrap}$, percentage of the extrapolated area under the curve at the total area under the curve; $V_z$, volume of distribution; $MRT_{last}$, Mean residence time to the last measured concentration; $V_{ss}$, volume of distribution at steady state.)

As shown in FIGS. 20A-20C and table 1, in same dosing condition (10 mg/kg), $C_{max}$ value was almost 4 fold increased by PEG modification versus nonmodified YJ-1 aptamer and the AUG value of PEG-YJ-1 was 10 fold higher than nonmodified YJ-1. Furthermore, the CL value is nearly 13 fold lower than nonmodified YJ-1. This pharmacokinetic value shows PEG modification is very valuable to aptamer administration.

Example 18

In Vivo Metastasis Inhibition Assay

The inhibition of CEA dependent liver metastasis of colon cancer by RNA aptamer in vivo (in metastasis animal model) was examined by a metastasis inhibition assay. For a metastasis inhibition assay, about 6 week-old male nude mice (BALB/cAnNCrI, NARA Bio, Seoul, Korea) were acclimated for 1 week. A mouse model of liver metastasis was established by intrasplenic injection of CEA-positive colon cancer cells, LS174T cell line ($2 \times 10^6$ cells), as described in 'Jeong J S, Lee S W, Hong S H, et al. Antitumor effects of systemically delivered adenovirus harboring trans-splicing ribozyme in intrahepatic colon cancer mouse model. Clin Cancer Res 2008; 14:281-290', the entire contents of which are incorporated herein by reference. The cells were pre-incubated with PEG-YJ-1 or PEG-mutant aptamer (80 μg/kg) prepared in Example 17-1 at 37° C. for 5 min before injection into the mouse.

The mice were killed, and the degree of metastasis was analyzed 35 days after splenic injection of colorectal carcinoma cells treated with PEG aptamer as follows. The whole liver lobes and spleen were removed, measured, and photographed. After serially sectioning of the liver tissue in 2 mm thickness, entire liver slices from each mouse were fixed in 10% neutralized buffered formalin and processed for paraffin

TABLE 1

| Parameter | PEG aptamer | | | | Non-PEG aptamer |
|---|---|---|---|---|---|
| | 1 mg · kg⁻¹ (IV) | 10 mg · kg⁻¹ (IV) | 100 mg · kg⁻¹ (IV) | 10 mg · kg⁻¹ (IP) | 10 mg · kg⁻¹ (IV) |
| $\lambda_Z$ (h⁻¹) | 0.53 ± 0.19 | 0.47 ± 0.16 | 0.31 ± 0.04 | 0.48 ± 0.30 | 0.21 ± 0.09 |
| $t_{max}$ (h) | 0.25 ± 0.00 | 0.25 ± 0.00 | 0.25 ± 0.00 | 0.5 ± 0.00 | 0.25 ± 0.00 |
| $C_{max}$ (μg · ml⁻¹) | 2.93 ± 1.61 | 13.63 ± 1.39 | 1140.55 ± 221.11 | 1.08 ± 0.18 | 3.20 ± 0.19 |
| $AUC_{last}$ (μg · ml⁻¹ · h) | 2.56 ± 0.78 | 6.88 ± 0.76 | 463.44 ± 73.10 | 2.40 ± 0.75 | 0.51 ± 0.07 |
| $AUC_{inf}$ (μg · ml⁻¹ · h) | 2.56 ± 0.78 | 6.90 ± 0.76 | 463.45 ± 73.10 | 2.40 ± 0.75 | 0.51 ± 0.06 |
| $AUC_{\%Extrap}$ (%) | 0.23 ± 0.27 | 0.19 ± 0.23 | 0.00 ± 0.00 | 0.06 ± 0.04 | 0.46 ± 0.28 |
| $V_z$ (l · kg⁻¹) | 1.01 ± 0.78 | 3.64 ± 1.94 | 0.73 ± 0.14 | 14.01 ± 12.00* | 120.16 ± 66.94 |
| CL (l · h⁻¹ · kg⁻¹) | 0.42 ± 0.14 | 1.46 ± 0.15 | 0.22 ± 0.04 | 4.63 ± 1.99* | 20.00 ± 2.51 |
| $MRT_{last}$ (h) | 1.79 ± 0.52 | 1.27 ± 0.22 | 0.39 ± 0.05 | 1.90 ± 0.30 | 1.48 ± 0.20 |
| $V_{ss}$ (·kg⁻¹) | 0.81 ± 0.52 | 1.86 ± 0.37 | 0.09 ± 0.01 | — | 29.49 ± 4.78 |

(Volume and clearance for IP administration are actually Volume/F or Clearance/F where F is the fraction of dose absorbed.

embedding. Tissue sections of 4- to 6-μm thickness were stained with hematoxylin and eosin (H&E) or immunoblotted with mouse monoclonal anti-human CEA (1:5000, DAKO, Glostrup, Denmark). The microscopic images were scanned under the virtual microscope (Aperio Technologica, Vista, Calif.). The tumor 11 fraction was calculated from the program of Aperio Imagescope v10.2.2.2319, and then the tumor weight was estimated by multiplication of liver weight and tumor fraction. For hepatotoxicity, serum level of AST/ALT (1 U/ml) was measured through enzyme activity assay (n=7 each) using a biochemical autoanalyzer (Toshiba TBA-200FR; Toshiba medical systems, Tustin, Calif.).

Figure 21A:
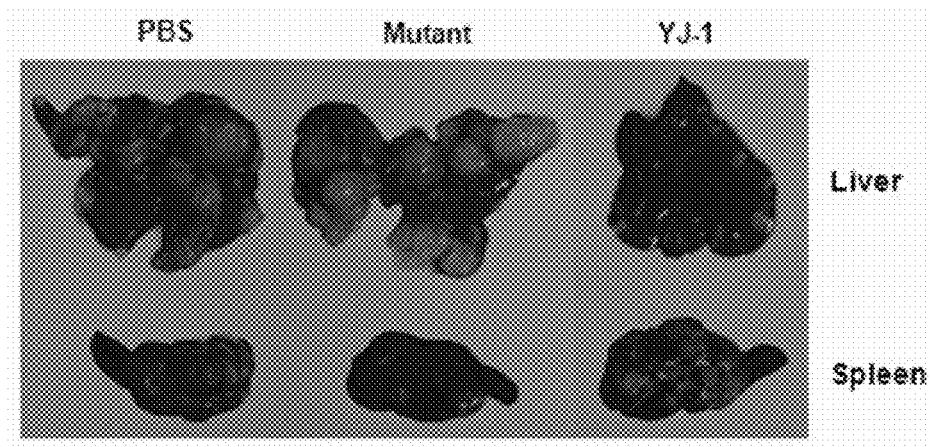
FIG. 21A shows metastasized liver and spleen depending on aptamer treatment, 21B shows tumor mass depending on aptamer treatment, and 21C shows Serum AST/ALT level depending on aptamer treatment.
Figure 21B:
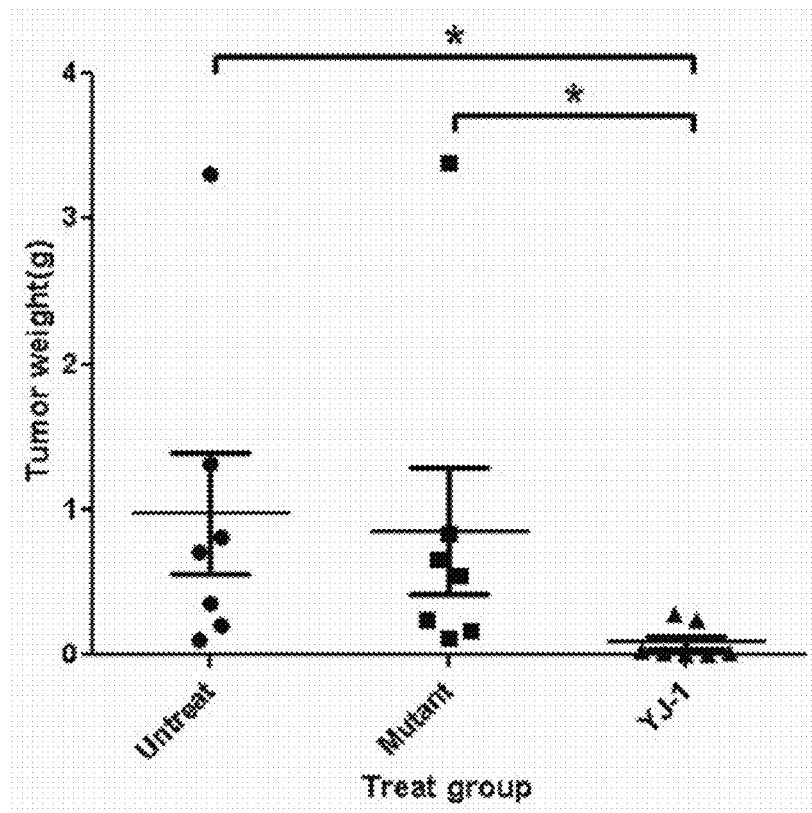
Figure 21C:
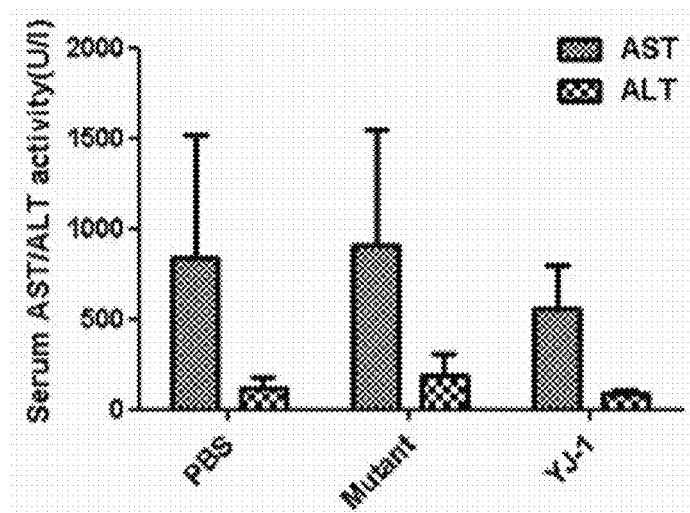

The results of inhibition of CEA-mediated liver metastasis of colon cancer by RNA aptamer in metastasis animal model were shown in FIGS. 21A-21C. FIG. 21A shows representative metastasized liver and spleen in mice after splenic injection of LS 174T cells treated with PEG-YJ-1 aptamer or PEG-mutant aptamer, wherein Mice injected with untreated cells (PBS) were used as controls. FIG. 21B shows plotted tumor masses of PEG-YJ-1 or PEG-mutant aptamer-treated group and untreated group (n=7 each) determined as above. Average tumor mass was presented with standard deviation. *=p<0.02.

As shown in FIGS. 21A and 21B, significant difference was observed between the groups treated with PEG-YJ-1 aptamer and control or PEG-mutant aptamer in incidence of hepatic metastasis. The mean values of tumor mass (g) were as follows: 0.97±1.11 for control group, 0.85±1.15 for PEG-mutant aptamer group and 0.08±0.12 for PEG-YJ-1 aptamer group. There was a 91% decrease in total tumor volume of hepatic metastasis in the PEG-YJ-1 aptamer-treated group as compared with the control group (P<0.02) but PEG-mutant aptamer treated group has no significant difference with the control group.

FIG. 21C shows serum AST/ALT level of PEG-YJ-1, PEG-mutant aptamer, or untreated group determined as above. As shown in FIG. 21C, AST/ALT levels in mice serum were not affected in PEG-YJ-1 aptamer group in contrast with significant increase in control or PEG-mutant aptamer group, indicating least hepatotoxicity by the RNA aptamer.

Statistics

For in vivo experiment, the between-group differences were assessed with analysis of variance (ANOVA). In the case of highly skewed distribution of measurements and small sample sizes, we used nonparametric statistical tests (Kruskal-Wallis test for overall comparison and Wilcoxon's rank-sum test for pairwise comparison). All data were expressed as the average±standard deviation. Differences were considered to be statistically significant at p<0.05.

Accordingly, the metastasis inhibitor according to the present invention may effectively inhibit metastasis to other tissues, one of important problems of cancer treatment, and thus, may be used as a therapeutic agent for inhibiting metastasis, and may be used as a cancer therapeutic agent through combined administration with other anticancer agents, and the RNA aptamers may be used for a diagnosis agent capable of measuring and expecting the degree of metastasis to other tissues of colon cancer, etc.

What is claimed is:

1. A method for preventing or inhibiting cancer metastasis, the method comprising administering an RNA aptamer to a patient in need of inhibition of metastasis,
wherein the RNA aptamer is 35 to 49 bases in length and binds to a linkage region between N domain and A1 domain of carcinoembryonic antigen (CEA), and the RNA aptamer comprises continuous 35 or more bases comprising the nucleotide sequence from $9^{th}$ to $43^{rd}$ positions of following SEQ ID NO: 13:
<SEQ ID NO: 13>
GCGGAAGCGUGCUGGGCUA-
GAAUAAUAAUAAGAAAACCAGUACUUUCGU; and
wherein C_(cytosine) and U_(uracil) in the RNA aptamer is modified by substituting 2' hydroxyl group with fluoro group.

2. The method according to claim 1, wherein the RNA aptamer comprises the nucleotide sequence of SEQ ID NO: 14.

3. The method according to claim 1, wherein the cancer is selected from the group consisting of colon cancer, stomach cancer, pancreatic cancer, and lung cancer.

4. The method according to claim 1, wherein the cancer metastasis is a cancer metastasis to liver.

5. The method according to claim 1, wherein the RNA aptamer is modified by at least one method selected from
conjugating with polyethyleneglycol or cholesterol at 5' end; and
attaching idT (inverted deoxy thymidylate) at 3' end.

6. The method according to claim 5, wherein the RNA aptamer comprises the nucleotide sequence of SEQ ID NO: 13 or 14.

7. The method according to claim 5, wherein the cancer is selected from the group consisting of colon cancer, stomach cancer, pancreatic cancer, and lung cancer.

8. The method according to claim 5, wherein the cancer metastasis is a cancer metastasis to liver.

9. The method according to claim 5, wherein
the RNA aptamer consists of the nucleotide sequence of SEQ ID NO: 13;
the RNA aptamer is modified by conjugating with polyethyleneglycol at 5' end and attaching idT (inverted deoxy thymidylate) at 3' end.

10. The method according to claim 1, wherein the RNA aptamer consists of the nucleotide sequence of SEQ ID NO: 13 in which C (cytosine) and U (uracil) are modified by substituting 2' hydroxyl group with fluoro group.

11. The method according to claim 1, wherein the RNA aptamer consists of the nucleotide sequence of SEQ ID NO: 14 in which C (cytosine) and U (uracil) are modified by substituting 2' hydroxyl group with fluoro group.

12. A method for preventing or inhibiting cancer metastasis, comprising administering an RNA aptamer to a patient in need of inhibition of metastasis,
wherein:
the RNA aptamer binds to a linkage region between N domain and A1 domain of carcinoembryonic antigen (CEA) and comprises continuous 35 or more bases comprising the nucleotide sequence from $9^{th}$ to $43^{rd}$ positions of following SEQ ID NO: 13:
<SEQ ID NO: 13>
GCGGAAGCGUGCUGGGCUA-
GAAUAAUAAUAAGAAAACCAGUACUUUCGU;
the RNA aptamer is modified by at least one method selected from conjugating with polyethyleneglycol or cholesterol at 5' end; and attaching idT (inverted deoxy thymidylate) at 3' end;
the RNA aptamer consists of the nucleotide sequence of SEQ ID NO: 13; and
C (cytosine) and U (uracil) in the RNA aptamer is modified by substituting 2' hydroxyl group with fluoro group.

* * * * *

```
                             SEQUENCE LISTING

<160> NUMBER OF SEQ ID NOS: 34

<210> SEQ ID NO 1
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 1
gggagagcgg aagcgugcug ggcuagaaua auaauaagaa aaccaguacu uucguguccc      60
gggagggugc auaacccaga ggucgaugga ucc                                  93

<210> SEQ ID NO 2
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 2
gggagagcgg aagcgugcug ggcuagaaua auaauaagaa aaccaguacu uucgugugcc      60
gggcgggucc auaacccaga ggucgaugga ucc                                  93

<210> SEQ ID NO 3
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 3
gggagagcgg aagcgugcug ggcuagaaua auaauaagaa aaccaguacu uucguguccc      60
gggagguucc auaacccaga ggucgaugga ucc                                  93
```

```
<210> SEQ ID NO 4
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 4
gggagagcgg aagcgugcug ggcuagaaua auaauaagaa aaccaguacu uucguguccc      60
gggaggagcc auaacccaga ggucgaugga ucc                                  93

<210> SEQ ID NO 5
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 5
gggagagcgg aagcgugcug ggcuagaaua auaauaagaa aaccaguacu uucguguccc      60
gggaggacac auaacccaga ggucgaugga ucc                                  93

<210> SEQ ID NO 6
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 6
gggagagcgg aagcgugcug ggcuagaaua auaauaagaa aaccagaacu uucguguccc      60
gggagguuuc auaacccaga ggucgaugga ucc                                  93

<210> SEQ ID NO 7
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 7
gggagagcgg aagcgugcug ggcuagaaua auaauaagaa aaccaguacu uucgcguccc      60
aggagggucc auaacccaga ggucgaugga ucc                                  93

<210> SEQ ID NO 8
<211> LENGTH: 94
<212> TYPE: RNA
<213> ORGANISM: Artificial Sequence
<220> FEATURE:
<223> OTHER INFORMATION: RNA aptamer for CEA

<400> SEQUENCE: 8
gggagagcgg aagcgugcug ggcuagaaua auaauaagaa aaccaguacu uucgugucccc     60 cgggaggauu cauaacccag aggucgaugg aucc                                 94

<210> SEQ ID NO 9
<211> LENGTH: 95
<212> TYPE: RNA
<213> ORGANISM: Artificial Sequence
<220> FEATURE:
<223> OTHER INFORMATION: RNA aptamer for CEA
```

-continued

<400> SEQUENCE: 9
gggagagcgg aagcgugcug ggcuagaaua auaauaagaa aaaccaguac uuucgugucc    60
cgggagaggu acauaaccca gaggucgaug gaucc                              95

<210> SEQ ID NO 10
<211> LENGTH: 93
<212> TYPE: RNA
<213> ORGANISM: Artificial Sequence
<220> FEATURE:
<223> OTHER INFORMATION: RNA aptamer for CEA

<400> SEQUENCE: 10
gggagagcgg aagcgugcug ggcucgaaua auaauaacga aaaccaguac uuucgugucc    60
cgggaggacc auaacccaga ggucgaugga ucc                                93

<210> SEQ ID NO 11
<211> LENGTH: 92
<212> TYPE: RNA
<213> ORGANISM: Artificial Sequence
<220> FEATURE:
<223> OTHER INFORMATION: RNA aptamer for CEA

<400> SEQUENCE: 11
gggagagcgg aagcgugcug ggcucgaaua auaauaagaa aaccaguacu uucguguccc    60
gggagggcca uacccagag gucgauggau cc                                  92

<210> SEQ ID NO 12
<211> LENGTH: 92
<212> TYPE: RNA
<213> ORGANISM: Artificial Sequence
<220> FEATURE:
<223> OTHER INFORMATION: RNA aptamer for CEA

<400> SEQUENCE: 12
gggagagcgg aagcgugcug ggcuagaaua auaauaagaa aaccaguacu uucguguccc    60
gggagggcca uaacccagag gucgauggau cc                                 92

<210> SEQ ID NO 13
<211> LENGTH: 49
<212> TYPE: RNA
<213> ORGANISM: Artificial Sequence
<220> FEATURE:
<223> OTHER INFORMATION: RNA aptamer for CEA

<400> SEQUENCE: 13
gcggaagcgu gcugggcuag aauaauaaua agaaaaccag uacuuucgu               49

<210> SEQ ID NO 14
<211> LENGTH: 35
<212> TYPE: RNA
<213> ORGANISM: Artificial Sequence
<220> FEATURE:
<223> OTHER INFORMATION: RNA aptamer for CEA

<400> SEQUENCE: 14
gugcugggcu agaauaauaa uaagaaaacc aguac                              35

<210> SEQ ID NO 15
<211> LENGTH: 49
<212> TYPE: RNA
<213> ORGANISM: Artificial Sequence
<220> FEATURE:
<223> OTHER INFORMATION: Mutant RNA aptamer for CEA

```
<400> SEQUENCE: 15
gcggaagcgu gcugggcuag ggcggcggcg ggaaaaccag uacuuucgu                    49

<210> SEQ ID NO 16
<211> LENGTH: 35
<212> TYPE: RNA
<213> ORGANISM: Artificial Sequence
<220> FEATURE:
<223> OTHER INFORMATION: Mutant RNA aptamer for CEA

<400> SEQUENCE: 16
gugcugggcu agggcggcgg cgggaaaacc aguac                                  35

<210> SEQ ID NO 17
<211> LENGTH: 23
<212> TYPE: RNA
<213> ORGANISM: Artificial Sequence
<220> FEATURE:
<223> OTHER INFORMATION: Loop region

<400> SEQUENCE: 17
ggcuagaaua auaauaagaa aac                                               23

<210> SEQ ID NO 18
<211> LENGTH: 95
<212> TYPE: RNA
<213> ORGANISM: Artificial Sequence
<220> FEATURE:
<223> OTHER INFORMATION: RNA aptamer for CEA
<220> FEATURE:
<221> NAME/KEY: conflict
<222> LOCATION: (38)
<223> OTHER INFORMATION: n is G or C or absent.
<220> FEATURE:
<221> NAME/KEY: conflict
<222> LOCATION: (62)
<223> OTHER INFORMATION: n is G or C or absent
<220> FEATURE:
<221> NAME/KEY: conflict
<222> LOCATION: (70)..(71)
<223> OTHER INFORMATION: n is independently A or U or G or C

<400> SEQUENCE: 18
gggagagcgg aagcgugcug ggcumgaaua auaauaanra aaaccagwac uuucgygusc        60
cnrgrvrgdn ncauaaccca gaggucgaug gaucc                                  95

<210> SEQ ID NO 19
<211> LENGTH: 32
<212> TYPE: DNA
<213> ORGANISM: Artificial Sequence
<220> FEATURE:
<223> OTHER INFORMATION: Full-CEA-5'-primer

<400> SEQUENCE: 19
cccaagctta gaccatggag tctccctcgg cc                                     32

<210> SEQ ID NO 20
<211> LENGTH: 44
<212> TYPE: DNA
<213> ORGANISM: Artificial Sequence
<220> FEATURE:
<223> OTHER INFORMATION: Full-CEA-3'-primer

<400> SEQUENCE: 20
gctctagact atatcagagc aaccccaacc agcactccaa tcat                        44
```

<210> SEQ ID NO 21
<211> LENGTH: 26
<212> TYPE: DNA
<213> ORGANISM: Artificial Sequence
<220> FEATURE:
<223> OTHER INFORMATION: N domain 5'-primer

<400> SEQUENCE: 21
cgaattcaag ctcactattg aatcca                                    26

<210> SEQ ID NO 22
<211> LENGTH: 30
<212> TYPE: DNA
<213> ORGANISM: Artificial Sequence
<220> FEATURE:
<223> OTHER INFORMATION: B3 domain 3'-primer

<400> SEQUENCE: 22
cccaagcttc taagatgcag agactgtgat                                30

<210> SEQ ID NO 23
<211> LENGTH: 27
<212> TYPE: DNA
<213> ORGANISM: Artificial Sequence
<220> FEATURE:
<223> OTHER INFORMATION: A1 domain 5'-primer

<400> SEQUENCE: 23
cgaattcaag ccctccatct ccagcaa                                   27

<210> SEQ ID NO 24
<211> LENGTH: 32
<212> TYPE: DNA
<213> ORGANISM: Artificial Sequence
<220> FEATURE:
<223> OTHER INFORMATION: N domain 3'-primer

<400> SEQUENCE: 24
cccaagcttc tacagctccg ggtatacccg ga                             32

<210> SEQ ID NO 25
<211> LENGTH: 30
<212> TYPE: DNA
<213> ORGANISM: Artificial Sequence
<220> FEATURE:
<223> OTHER INFORMATION: A1 domain 3'-primer

<400> SEQUENCE: 25
cccaagcttc tacgggccat agaggacatt                                30

<210> SEQ ID NO 26
<211> LENGTH: 49
<212> TYPE: DNA
<213> ORGANISM: Artificial Sequence
<220> FEATURE:
<223> OTHER INFORMATION: 5'-primer for linking site between N and A1
     domains

<400> SEQUENCE: 26
tggccagttc cgggtatacc gggagctgtc caagccctcc atctccagc           49

<210> SEQ ID NO 27
<211> LENGTH: 49
<212> TYPE: DNA
<213> ORGANISM: Artificial Sequence
<220> FEATURE:

<223> OTHER INFORMATION: 3'-primer for linking site between N and A1
       domains

<400> SEQUENCE: 27
gctggagatg gagggcttgg acagctcccg gtatacccgg aactggcca                49

<210> SEQ ID NO 28
<211> LENGTH: 41
<212> TYPE: DNA
<213> ORGANISM: Artificial Sequence
<220> FEATURE:
<223> OTHER INFORMATION: 5'-primer for RNA library

<400> SEQUENCE: 28
ggtaatacga ctcactatag ggagagcgga agcgtgctgg g                        41

<210> SEQ ID NO 29
<211> LENGTH: 28
<212> TYPE: DNA
<213> ORGANISM: Artificial Sequence
<220> FEATURE:
<223> OTHER INFORMATION: 3'-primer for RNA library

<400> SEQUENCE: 29 gggggggatcc atcgacctct gggttatg                                      28

<210> SEQ ID NO 30
<211> LENGTH: 17
<212> TYPE: DNA
<213> ORGANISM: Artificial Sequence
<220> FEATURE:
<223> OTHER INFORMATION: reverse primer for reverse trancription and PCR

<400> SEQUENCE: 30
acgaaagtac tggtttt                                                   17

<210> SEQ ID NO 31
<211> LENGTH: 15
<212> TYPE: DNA
<213> ORGANISM: Artificial Sequence
<220> FEATURE:
<223> OTHER INFORMATION: forward primer for PCR

<400> SEQUENCE: 31
gcggaagcgt gctgg                                                     15

<210> SEQ ID NO 32
<211> LENGTH: 19
<212> TYPE: DNA
<213> ORGANISM: Artificial Sequence
<220> FEATURE:
<223> OTHER INFORMATION: reverse primer for reverse trancription and PCR

<400> SEQUENCE: 32
acgaaagtac tggttttct                                                 19

<210> SEQ ID NO 33
<211> LENGTH: 87
<212> TYPE: DNA
<213> ORGANISM: Artificial Sequence
<220> FEATURE:
<223> OTHER INFORMATION: GROUP II sequence

<400> SEQUENCE: 33
gggagagcgg aagcgtgctg ggccggatga ctcactaaaa acaaaaacaa tattgtgaac    60

```
catcataacc cagaggtcga tggatcc                                              87

<210> SEQ ID NO 34
<211> LENGTH: 87
<212> TYPE: DNA
<213> ORGANISM: Artificial Sequence
<220> FEATURE:
<223> OTHER INFORMATION: GROUP III sequence

<400> SEQUENCE: 34
gggagagcgg aagcgtgctg ggcccattgt ggagatgcca ttcttagaac gcttttggc     60 ttacataacc cagaggtcga tggatcc                                              87
```